United States Patent
Grillo-López

(10) Patent No.: US 9,296,821 B2
(45) Date of Patent: *Mar. 29, 2016

(54) COMBINATION THERAPIES FOR B-CELL LYMPHOMAS COMPRISING ADMINISTRATION OF ANTI-CD20 ANTIBODIES

(75) Inventor: Antonio J. Grillo-López, Rancho Sante Fe, CA (US)

(73) Assignee: Biogen Inc., Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/524,896

(22) Filed: Jun. 15, 2012

(65) Prior Publication Data

US 2012/0258102 A1  Oct. 11, 2012

Related U.S. Application Data

(60) Division of application No. 11/840,956, filed on Aug. 18, 2007, now Pat. No. 8,329,172, which is a continuation of application No. 10/196,732, filed on Jul. 17, 2002, now abandoned, which is a continuation of application No. 09/372,202, filed on Jun. 11, 1999, now Pat. No. 6,455,043.

(60) Provisional application No. 60/096,180, filed on Aug. 11, 1998.

(51) Int. Cl.
| | |
|---|---|
| A61K 39/395 | (2006.01) |
| C07K 16/28 | (2006.01) |
| A61K 51/10 | (2006.01) |
| C02F 1/00 | (2006.01) |
| C07K 16/30 | (2006.01) |
| A61K 39/00 | (2006.01) |

(52) U.S. Cl.
CPC ....... *C07K 16/2887* (2013.01); *A61K 39/39541* (2013.01); *A61K 39/39558* (2013.01); *A61K 51/1027* (2013.01); *C02F 1/003* (2013.01); *C07K 16/3061* (2013.01); *A61K 2039/505* (2013.01); *C02F 2307/02* (2013.01); *C07K 2317/24* (2013.01); *C07K 2317/77* (2013.01)

(58) Field of Classification Search
None
See application file for complete search history.

(56) References Cited

U.S. PATENT DOCUMENTS

| | | |
|---|---|---|
| 4,816,397 A | 3/1989 | Boss et al. |
| 4,816,567 A | 3/1989 | Cabilly et al. |
| 4,831,175 A | 5/1989 | Gansow et al. |
| 4,975,278 A | 12/1990 | Senter et al. |
| 5,099,069 A | 3/1992 | Gansow et al. |
| 5,124,471 A | 6/1992 | Gansow et al. |
| 5,145,677 A | 9/1992 | Von Eichborn et al. |
| 5,165,922 A | 11/1992 | Hellstrom et al. |
| 5,225,535 A | 7/1993 | De Freitas et al. |
| 5,225,539 A | 7/1993 | Winter |
| 5,246,692 A | 9/1993 | Gansow et al. |
| 5,250,732 A | 10/1993 | Kogan et al. |
| 5,286,850 A | 2/1994 | Gansow et al. |
| 5,439,665 A | 8/1995 | Hansen et al. |
| 5,460,785 A | 10/1995 | Rhodes et al. |
| 5,500,362 A | 3/1996 | Robinson et al. |
| 5,530,101 A | 6/1996 | Queen et al. |
| 5,595,721 A | 1/1997 | Kaminski et al. |
| 5,633,425 A | 5/1997 | Lonberg et al. |
| 5,648,267 A | 7/1997 | Reff |
| 5,677,171 A | 10/1997 | Hudziak et al. |
| 5,677,180 A | 10/1997 | Robinson et al. |
| 5,686,072 A | 11/1997 | Uhr et al. |
| 5,691,135 A | 11/1997 | Braun et al. |
| 5,691,320 A | 11/1997 | Von Borstel et al. |
| 5,693,780 A | 12/1997 | Newman et al. |
| 5,721,108 A | 2/1998 | Robinson et al. |
| 5,726,023 A | 3/1998 | Cheever et al. |
| 5,736,137 A | 4/1998 | Anderson et al. |
| 5,776,456 A | 7/1998 | Anderson et al. |
| 5,843,398 A | 12/1998 | Kaminski et al. |
| 5,843,439 A | 12/1998 | Anderson et al. |
| 6,015,542 A | 1/2000 | Kaminski et al. |
| 6,090,365 A | 7/2000 | Kaminski et al. |
| 6,111,166 A | 8/2000 | Van de Winkel |
| 6,120,767 A | 9/2000 | Robinson et al. |
| 6,183,744 B1 | 2/2001 | Goldenberg |
| 6,287,537 B1 | 9/2001 | Kaminski et al. |

(Continued)

FOREIGN PATENT DOCUMENTS

| | | |
|---|---|---|
| AU | 56032/94 | 6/1994 |
| EP | 0 125 023 A1 | 11/1984 |

(Continued)

OTHER PUBLICATIONS

Declaration of Michael L. Grossbard, M.D., In Support of the Petition for Inter Partes Review of U.S. Pat. No. 8,329,172 (Grillo Lopez et al., "Combination Therapies for B Cell Lymphomas Comprising Administration of Anti CD20 Antibody" published Dec. 11, 2012), dated Dec. 5, 2014, pp. 1-107.*

"Dictionary of Cancer Terms", National Cancer Institute at the National Institutes of Health, http://www.cancergov.dictionary?CdrID=45735, 1 pp, printed May 22, 2012.

"GlaxoSmithKline and Genmab Announce Results from a Study of Arzerra in Rituximab Refractory Follicular NHL," *PharmaLive. corn*, pp. 1-2, Aug. 17, 2009. Obtained online at http://www.pharmalive.com/News/Print.cfm?articleid=645905.

(Continued)

*Primary Examiner* — Ron Schwadron
(74) *Attorney, Agent, or Firm* — Wendy Lee; Ginger R. Dreger; Arnold & Porter LLP

(57) ABSTRACT

New combined therapeutic regimens for treatment of B-cell lymphomas are disclosed which comprise, in particular, administration of anti-CD20 antibodies to patients having low-, intermediate- or high-grade non-Hodgkin's lymphomas.

6 Claims, No Drawings

(56) References Cited

U.S. PATENT DOCUMENTS

| | | | |
|---|---|---|---|
| 6,306,393 | B1 | 10/2001 | Goldenberg |
| 6,399,061 | B1 | 6/2002 | Anderson et al. |
| 6,399,649 | B1 | 6/2002 | Lerner |
| 6,455,043 | B1 | 9/2002 | Grillo-Lopez |
| RE38,008 | E | 2/2003 | Abrams et al. |
| 6,565,827 | B1 | 5/2003 | Kaminski et al. |
| 6,652,852 | B1 | 11/2003 | Robinson et al. |
| 6,682,734 | B1 | 1/2004 | Anderson et al. |
| 6,893,625 | B1 | 5/2005 | Robinson et al. |
| 7,381,560 | B2 | 6/2008 | Anderson et al. |
| 7,422,739 | B2 | 9/2008 | Anderson et al. |
| 7,682,612 | B1 | 3/2010 | White et al. |
| 7,744,877 | B2 | 6/2010 | Anderson et al. |
| 8,206,711 | B2 | 6/2012 | White et al. |
| 8,329,172 | B2 | 12/2012 | Grillo-Lopez |
| 8,557,244 | B1 | 10/2013 | White et al. |
| 8,821,873 | B2 | 9/2014 | White et al. |
| 2002/0009444 | A1 | 1/2002 | Grillo-Lopez |
| 2002/0197255 | A1 | 12/2002 | Anderson et al. |
| 2003/0018014 | A1 | 1/2003 | Lerner |
| 2003/0021781 | A1 | 1/2003 | Anderson et al. |
| 2003/0026804 | A1 | 2/2003 | Grillo-Lopez |
| 2003/0082172 | A1 | 5/2003 | Anderson et al. |
| 2003/0095963 | A1 | 5/2003 | Anderson et al. |
| 2003/0147885 | A1 | 8/2003 | Anderson et al. |
| 2003/0206903 | A1 | 11/2003 | Grillo-Lopez |
| 2004/0167319 | A1 | 8/2004 | Teeling et al. |
| 2004/0213784 | A1 | 10/2004 | Grillo-Lopez |
| 2005/0163708 | A1 | 7/2005 | Robinson et al. |
| 2005/0186205 | A1 | 8/2005 | Anderson et al. |
| 2006/0034835 | A1 | 2/2006 | Adams et al. |
| 2008/0038261 | A1 | 2/2008 | Grillo-Lopez |
| 2009/0074760 | A1 | 3/2009 | Grillo-Lopez et al. |
| 2010/0080769 | A1 | 4/2010 | Grillo-Lopez et al. |
| 2011/0165159 | A1 | 7/2011 | Grillo-Lopez et al. |
| 2012/0251534 | A1 | 10/2012 | Grillo-Lopez |
| 2012/0251535 | A1 | 10/2012 | Grillo-Lopez |
| 2012/0258101 | A1 | 10/2012 | Grillo-Lopez |
| 2012/0258102 | A1 | 10/2012 | Grillo-Lopez |
| 2013/0273039 | A1 | 10/2013 | Grillo-Lopez |
| 2013/0273041 | A1 | 10/2013 | Grillo-Lopez et al. |
| 2014/0030263 | A1 | 1/2014 | White et al. |
| 2014/0056887 | A1 | 2/2014 | Grillo-Lopez |
| 2014/0302018 | A1 | 10/2014 | White et al. |
| 2014/0363424 | A1 | 12/2014 | Grillo-Lopez et al. |
| 2015/0183882 | A1 | 7/2015 | Grillo-Lopez |

FOREIGN PATENT DOCUMENTS

| | | |
|---|---|---|
| EP | 0 173 494 A2 | 5/1986 |
| EP | 0 274 394 A2 | 7/1988 |
| EP | 0 274 394 A3 | 1/1990 |
| EP | 0 125 023 B1 | 6/1991 |
| EP | 0 510 949 A2 | 10/1992 |
| EP | 0 682 040 A1 | 11/1995 |
| EP | 0 669 836 B1 | 3/1996 |
| EP | 0 451 216 B1 | 11/1996 |
| EP | 0 752 248 A1 | 1/1997 |
| EP | 0 682 040 B1 | 8/1999 |
| EP | 0 125 023 B2 | 3/2002 |
| EP | 1 974 747 B1 | 6/2012 |
| JP | 5-508630 | 12/1993 |
| WO | WO 87/02671 A1 | 5/1987 |
| WO | WO 88/04936 A1 | 7/1988 |
| WO | WO 89/00999 A1 | 2/1989 |
| WO | WO 91/04320 A1 | 4/1991 |
| WO | WO 91/17770 | 11/1991 |
| WO | WO 92/07466 A1 | 5/1992 |
| WO | WO 93/02108 A1 | 2/1993 |
| WO | WO 94/08601 | 4/1994 |
| WO | WO 94/11007 | 5/1994 |
| WO | WO 94/11026 A2 | 5/1994 |
| WO | WO 96/18413 | 6/1996 |
| WO | WO 98/42378 | 10/1998 |
| WO | WO 00/09160 A1 | 2/2000 |
| WO | WO 00/27428 A1 | 5/2000 |
| WO | WO 00/27433 A1 | 5/2000 |
| WO | WO 01/10460 A1 | 2/2001 |
| WO | WO 2004/056312 A2 | 7/2004 |

OTHER PUBLICATIONS

[unknown author] "IDEC Pharmaceuticals Announces Positive Preliminary Results for Pivotal Trial of IDEC-C2B8" *The Free Library* May 21, 1996. [retrieved again on Aug. 2, 2010 Retrieved from http://www.thefreelibrary.com/IDEC+PHARMACEUTICALS+ANNOUNCES+POSITIVE+PRELIMINARY+RESULTS+FOR ... -a018307934.

[unknown author} "Non-progressing, low-grade NHL: Risk reduction demonstrated in NCI-sponsored trial using up to 16 doses of RITUXAN following CVP in NHL" [retrieved on Aug. 25, 2010]. Retrieved from http://www.rituxan.com/lymphoma/hcp/indications/E1496/index.m.

Adams R.A. *Cancer Res.* 27: 2479-82, 1967. Formal discussion: the role of transplantation in the experimental investigation of human leukemia and lymphoma.

Adams R.A. et al. *Cancer Res.* 28(6): 1121-25, 1968. Direct implantation and serial transplantation of human acute lymphoblastic leukemia in hamsters, SB-2.

Alas S. et al. *Anticancer Res.* 20(5A): 2961-66, 2000. Potentiation of fludarabine cytotoxicity on non-Hodgkin's lymphoma by pentoxifylline and rituximab.

Alas S. et al. *Clin. Cancer Res.* 7(3): 709-23, 2001 Inhibition of interleukin 10 by rituximab results in down-regulation of bcl-2 and sensitization of B-cell non-Hodgkin's lymphoma to apoptosis.

Alas S. et al. *Clin. Cancer Res.* 8(3): 836-45, 2002. Rituximab modifies the cisplatinmitochondrial signaling pathway, resulting in apoptosis in cisplatin-resistant non-Hodgkin's lymphoma.

Amit A.G. et al., "Three-dimensional structure of an antigen-antibody complex at 2.8 A resolution," *Science* 233(4765): 747-53 (1986).

Anderson D.R. et al. *Biochem. Soc. Trans.* 25(2): 705-08, 1997. Targeted anti-cancer therapy using rituximab, a chimaeric anti-CD20 antibody (IDEC-C2B8) in the treatment of non-Hodgkin's B-cell lymphoma.

Anderson D.R. et al. Second IBC Int'l. Conference on Antibody Engineering, San Diego, Dec. 16-18, 1991. Immunoreactivity and effector function associated with a chimeric anti-CD20 antibody (abstract of presentation).

Anderson K.C. et al. *Blood* 63(6): 1424-33, 1984. Expression of human B cell-associated antigens on leukemias and lymphomas: a model of human B cell differentiation.

Anderson K.C. et al. *Blood* 69(2): 597-604, 1987. Hematologic engraftment and immune reconstitution posttransplantation with anti-B 1 purged autologous bone marrow.

Appelbaum F.R. *Hem. Onc. Clin. N Amer.* 5(5): 1013-25, 1991. Radiolabeled monoclonal antibodies in the treatment of non-Hodgkin's lymphoma.

Armitage J.O. et al. *Cancer* 50: 1695-1702, 1982. Predicting therapeutic outcome in patients with diffuse histiocytic lymphoma treated with cyclophosphamide, adriamycin, vincristine and prednisone (CHOP).

Armitage J.O. et al. *I Clin. Oncol.* 16(8): 2780-95, 1998. New approach to classifying non-Hodgkin's lymphomas: clinical features of the major histologic subtypes. Non-Hodgkin's Lymphoma Classification Project.

Armitage JO, "Treatment Of Non-Hodgkin's Lymphoma." N Engl. J. Med. 328(14): 1023-30 (Apr. 1993).

Arran R. et al. *I Clin. Oncol.* 16(4): 1538-46, 1998. Role of interferon alfa-2b in the induction and maintenance treatment of low-grade non-Hodgkin's lymphoma: results from a prospective, multicenter trial with double randomization.

Azogui 0. et al. *J. Immunol.* 131: 1205-08, 1983 Inhibition of IL-2 production after human allogeneic bone marrow transplantation.

Badger C.C. et al. *Cancer Res.* 46: 6223-28, 1986. Experimental radioimmunotherapy of murine lymphoma with $^{131}$I-labeled anti-T-cell antibodies.

(56) References Cited

OTHER PUBLICATIONS

Belhadj K. et al. *Ann. Oncol.* 15: 504-10, 2004. Efficiency of in vivo purging with rituximab prior to autologous peripheral blood progenitor cell transplantation in B-cell non-Hodgkin's lymphoma: a single institution study.
Berinstein N. et al. *Proc. Amer. Assn. Cancer Res.* 38: 85, abst. No. 567, Mar. 1997. IDEC-C2B8 (rituximab) levels correlate with response in low-grade or follicular non-Hodgkin's lymphoma (LG-F-NHL).
Berinstein N.L. et al. *Ann. Oncol.* 9: 995-1001, 1998. Association of serum rituximab (IDEC-C2B8) concentration and anti-tumor response in the treatment of recurrent low-grade or follicular non-Hodgkin's lymphoma.
Berinstein, "Principles of maintenance therapy," *Leukemia Res.* 30 Suppl. 1: S3-10 (2006).
Berkahn et al., "In vivo purging with rituximab prior to collection of stem cells for autologous transplantation in chronic lymphocytic leukemia," *J. Hematother. Stem Cell Res.* 11(2): 315-20 (2002).
Beychok S. (in) *Cells of Immunoglobulin Synthesis*, B. Pernis et al., eds. New York: Academic Press, 1979, pp. 69-88. Comparative aspects of in vitro and cellular assembly of immunoglobulins.
Bhan A.K. et al. *J. Exp. Med.* 154: 737-49, 1981. Stages of B cell differentiation in human lymphoid tissue.
Bierman et al., "High-dose therapy with autologous hematopoietic rescue for follicular low-grade non-Hodgkin's lymphoma," J. Clin. Oncol. 15(2):445-50 (1997).
Bierman P.J. et al. (in) Hoffman, R., ed., *Hematology*, 2d. ed., Churchill Livingstone, 1995, Chapter 81, pp. 1278-1298. Clinical manifestations and staging of and therapy for non-Hodgkin's lymphomas.
*Biogen Idec Inc. v. Corixa Corp.*, Case No. 01-CV-1637 IEG (RBB), Order Granting Patentees' Motion for Reconsideration, etc. (S.D. Cal., Jan. 22, 2004).
*Biogen Idec Inc. v. Corixa Corp.*, Case No. 01-CV-1637 IEG [Doc. Nos. 635, 552, 486] (S.D. Cal. Jan. 22, 2004).
*Biogen Idec Inc. v. Corixa Corp.*, Case No. 01-CV-1637 TEG (RBB), Stipulation of Dismissal of Claims and Counterclaims with Prejudice and Order (S.D.Cal., May 13, 2004).
Boon, "Toward a genetic analysis of tumor rejection antigens," *Adv. Cancer Res.* 58: 177-210 (1992).
Bosly A. et al. *Nouv. Rev. Fr. Hematol.* 32(1): 13-16, 1990. Interleukin-2 after autologous bone marrow transplantation as consolidative immunotherapy against minimal residual disease.
Boulianne G.L. et al. *Nature* 312: 643-46, 1984. Production of functional chimaeric mouse/human antibody.
Brunner K.T. et al. *Immunology* 14(2): 181-96, 1968. Quantitative assay of the lytic action of immune lymphoid cells on Cr-labelled allogeneic target cells in vitro; inhibition by isoantibody and by drugs.
Buchsbaum D.J. et al. *IJ Rad. Oncol. Biol. Phys.* 18: 1033-41, 1990. A comparison of $^{131}$ Ilabeled monoclonal antibody 17-1A treatment to external beam irradiation on the growth of LS174T human colon carcinoma xenografts.
Buchsbaum D.J. et al. *Cancer Res.* 50: 993s-999s, 1990. Comparative binding and preclinical localization and therapy studies with radiolabeled human chimeric and murine 17-1A monoclonal antibodies.
Buchsbaum D.J. et al. *Cancer Res.* 52: 637-642, 1992. Improved delivery of radiolabeled anti-B1 monoclonal antibody to Raji lymphoma xcnografts by prcdosing with unlabeled anti-B1 monoclonal antibody.
Buchsbaum D.J. et al. *Cancer Res.* 52: 6476-81, 1992. Therapy with unlabeled and $^{131}$Ilabeled pan-B-cell monoclonal antibodies in nude mice bearing Raji Burkitt's lymphoma xenografts.
Byrd J.C. *Cancer Biother. Radiopharm.* 14(4)L 323, 1999. Rituximab therapy in patients with chronic lymphocytic leukemia.
Byrd J.C. et al. *Blood* 92(10 Suppl. 1): 106a, abst. No. 432 Nov. 1998. Rituximab therapy in hematologic malignancy patients with circulating blood tumor cells: association with increased infusion-related side effects and rapid tumor lysis.
Byrd J.C. et al. *Blood* 92(10 Suppl. 1): 106a, abst. No. 433 Nov. 1998. Rituximab therapy in previously treated Waldenstrom's Macroglobulinemia: Preliminary evidence of activity.
Byrd J.C. et al. *J Clin. Oncol.* 17(3): 791-795, Mar. 1999. Rituximab therapy in hematologic malignancy patients with circulating blood tumor cells: association with increased infusion-related side effects and rapid blood tumor clearance.
Byrd J.C. et al. *J. Clin. Oncol.* 19(8): 2153-64, 2001. Rituximab using a thrice weekly dosing schedule in B-cell chronic lymphocytic leukemia and small lymphocytic lymphoma demonstrates clinical activity and acceptable toxicity.
Caligiuri M.A. et al. *J. Clin. Invest.* 91(1): 123-32, 1993. Selective modulation of human natural killer cells in vivo after prolonged infusion of low dose recombinant interleukin 2.
Caligiuri M.A. *Semin. Oncol.* 20(6 Suppl 9): 3-10, 1993. Low-dose interleukin-2 therapy: rationale and potential clinical applications.
Calvert J.E. et al. *Semin. Hematol.* 21(4): 226-243, 1984. Cellular events in the differentiation of antibody-secreting cells.
CancerNetwork, "Rituximab Effective in Patients with Bulky NHL", Feb. 1, 1999, www.cancernetwork.com/display/article/10165/86193.retrieved Feb. 23, 2011.
Catovsky D. et al. *Eur J. Cancer* 31A(13/14): 2146-54, 1995. Key issues in the treatment of chronic lymphocytic leukaemia (CLL).
Cayeux S. et al. *Blood* 74(6): 2270-77, 1989. T-cell ontogeny after autologous bone marrow transplantation: failure to synthesize interleukin-2 (IL-2) and lack of CD2- and CD3- mediated proliferation by both CD4- and CD8+ cells even in the presence of exogenous IL-2.
Cheson B.D. et al. *Blood* 87: 4990-97, 1996. National Cancer Institute-specified working group guidelines for chronic lymphocytic leukemia: revised guidelines for diagnosis and treatment.
Cheson, "Radioimmunotherapy of non-Hodgkin lymphomas," *Blood* 101(2): 391-8 (2003), Epub Sep. 19, 2002.
Chinn P. et al. *Proc. Ann. Mtg. Am. Assn. Cancer Res.* 33: 337, abst. No. 2012, 1992. Production and characterization of radiolabeled anti-CD20 monoclonal antibody: potential application to treatment of B-cell lymphoma.
Chinn P.C. et al. *Proc. Am. Assn. Cancer Res.* 40: 574, abst. No. 3786, 1999. A $^{90}$Y-labeled anti-CD20 monoclonal antibody conjugated to MX-DTPA, a high-affinity chelator for yttrium.
Chomczynki P. et al. *Anal. Biochem.* 162: 156-59, 1987. Single-step method of RNA isolation by acid guanidinium thiocyanate-phenol-chloroform extraction.
Chow K.U. et al. *Haematologica* 87: 33-43, 2002. Anti-CD20 antibody (IDEC-C2B8, rituximab) enhances efficacy of cytotoxic drugs on neoplastic lymphocytes in vitro: role of cytokines, complement, and caspascs.
Clark E.A. et al. *Proc. Nat'l Acad. Sci. USA* 82(6): 1766-70, 1985. Role of the Bp35 cell surface polypeptide in human B-cell activation.
Classon B.J. et al. *J. Exp. Med.* 169(4): 1497-1502, 1989. The primary structure of the human leukocyte antigen CD37, a species homologue of the rat MRC OC-44 antigen.
Cogliatti S.B. et al. *Sw. Med. Weekly* 192: 607-17, 2002. Who is WHO and what was REAL.
Cohen et al., "Retreatment with rituximab alone induces sustained remission in a patient with follicular lymphoma with multiple extranodal sites of involvement, relapsing soon after primary treatment with fludarabine-rituximab," *Hematol. J.* 4(2): 151-3 (2003).
Cohen Y. et al. *Leuk. Lymphoma* 43(7): 1485-87, 2002. Large B-cell lymphoma manifesting as an invasive cardiac mass: sustained local remission after combination of methotrexate and rituximab.
Coiffier B. *Ann. Oncol.* 83(Suppl 1): S73-S74, 2004. New treatment strategies in lymphomas: aggressive lymphomas.
Coiffier B. et al. *Blood* 92(6): 1927-32, 1998. Rituximab (anti-CD20 monoclonal antibody) for the treatment of patients with relapsing or refractory aggressive lymphoma: a multicenter phase II study.
Coiffier B. et al. *N Engl. J. Med.* 346(4): 235-42, 2002. CHOP chemotherapy plus rituximab compared with CHOP alone in elderly patients with diffuse large-B-cell lymphoma.
Coiffier, "Rituximab in combination with CHOP improves survival in elderly patients with aggressive non-Hodgkin's lymphoma," *Semin. Oncol.* 29(2 Suppl. 6): 18-22 (2002).

(56) References Cited

OTHER PUBLICATIONS

Coleman M. et al. *Blood* 102(11 pt.1): 29a, abst. No. 29, 2003. The BEXXAR® therapeutic regimen (tositumomab and Iodine 1-131 tositumomab) produced durable complete remissions in heavily pretreated patients with non-Hodgkin's lymphoma (NHL), rituximabrelapsed/ refractory disease, and rituximab-naive disease.
Colombat P. et al. *Blood* 97: 101-06, 2001. Rituximab (anti-CD20 monoclonal antibody) as single first-line therapy for patients with follicular lymphoma with a low tumor burden: clinical and molecular evaluation.
Cope. *Oncology* 8(4): 100, 1994. Antibody shows promise in treating B-cell lymphoma.
Curti B.D. *Crit. Rev. Oncol. Hematol.* 14(1): 29-39, 1993. Physical barriers to drug delivery in tumors.
Czuczman et al., "IDEC-C2B8/CHOP chemoimmunotherapy in patients with low-grade lymphoma: Interim clinical and bcl-2 (PCR) results", Annals of Oncology, vol. 7, Suppl. 1, pp. 56-57, (1996).
Czuczman M. et al. *Blood* 94(10 Supp. 1): 99a, abst. No. 432, 1999. Rituximab/CHOP chemoimmunotherapy in patients (PTS) with low grade lymphoma (LG/F NHL): progression free survival (PFS) after three years (median) follow-up.
Czuczman M.S. et al. *J. Clin. Oncol.* 17(1): 268-76, Jan. 1999. Treatment of patients with low-grade B-cell lymphoma with the combination of chimeric anti-CD20 monoclonal antibody and CHOP chemotherapy.
David G. Maloney et al., "IDEC-C2B8: Results of a Phase I Multiple-Dose Trial in Patiets with Relapsed Non-Hodgkin's Lymphoma", Journal of Clinical Oncology, vol. 15, No. 10, Oct. 1977, pp. 3266-3274.
Davis et al., "Retreatments with Rituxan (rituximab, IDEC-C2B8) have significant efficacy, do not cause HAMA, and are a viable minimally toxic alternative in relapsed or refractory non-Hodgkin's lymphoma (abstract)," *Blood* 90(10 Suppl. 1 Part 1): 509a (1997).
Davis et al., "Rituximab Anti-CD20 Monoclonal Antibody Therapy in Non-Hodgkin's Lymphoma: Safety and Efficacy of Re-Treatment," *J. Clin. Oncol.* 18: 3135-3143 (2000).
Davis T. et al. *Blood* 90(10 Suppl. 1): 509a, abst No. 2269, Nov. 1997. Retreatments with RITUXAN™ (Rituximab, IDEC-C2B8) have significant efficacy, do not cause HAMA, and are a viable minimally toxic alternative in relapsed or refractory non-Hodgkin's lymphoma (NHL).
Davis T. et al.. *Proc. Amer. Soc. Clin. Oncol.* 17: abst. No. 39, May 1998. Combination immunotherapy of low grade or follicular (LG/F) non-Hodgkin's lymphoma (NHL) with rituximab and alpha interferon: interim analysis.
Davis T.A. et al. *Blood* 86(10 Suppl. 1): 273a, abst. No. 1080, 1995. Yttrium labeled antiCD20 therapy for recurrent B cell lymphoma.
Davis T.A. et al. *Blood* 92(10 Suppl. 1): 414a, abst. No. 1710, Nov. 1998. Rituximab: phase II (PII) retreatment (ReRx) study in patients (PTS) with low grade or follicular (LG/F) NHL.
Davis T.A. et al. *Blood* 92(10 Suppl. 1): 414a, abst. No. 1711, Nov. 1998. Rituximab: first report of a phase II (PII) trial in NHL patients (PTS) with bulky disease.
Davis T.A. et al. *Clin. Cancer Res.* 5(3): 611-15, 1999. Therapy of B-cell lymphoma with anti-CD20 antibodies can result in the loss of CD20 antigen expression.
Davis T.A. et al. *I Clin. Oncol.* 17(6): 1851-57, 1999. Single-agent monoclonal antibody efficacy in bulky non-Hodgkin's lymphoma: results of a phase II trial of rituximab.
Davis T.A. et al. *Proc. Amer. Assn. Cancer Res.* 39: 435, abst. No. 2964, 1998. Therapy of B cell lymphoma with anti-CD20 can result in relapse with loss of CD20 expression.
Demidem A. et al. *Cancer Biother. Radiopharm.* 12(3): 177-86, 1997 Chimeric anti-CD20 (IDEC-C2B8) monoclonal antibody sensitizes a B cell lymphoma cell line to cell killing by cytotoxic drugs.
Demidem et al., Chimeric anti-CD20 antibody (IDEC-C2B8) is apoptotic and sensitizes drug resistant human B cell lymphomas and AIDS related lymphomas to the cytotoxic effect of CDDP, VP-16 and toxins *FASEB J9(3):A206*, Abstract #1197, 1995.

DeNardo G.L. et al. *Cancer Res.* 50(3 Suppl.): 1014s-1016s, 1990. Fractionated radioimmunotherapy of B-cell malignancies with $^{131}$I-Lym-1.
DeNardo G.L. et al. *I.J. Rad. Oncol. Biol.Phys.* 11(2): 335-48, 1985. Requirements for a treatment plan in system for radioimmunotherapy.
DeNardo S.J. et al. *Antibody Immunoconj. Radiopharm.* 1(1): 17-33, 1988. Pilot studies of radioimmunotherapy of B cell lymphoma and leukemia using 1-131 Lym-1 monoclonal antibody.
DeNardo S.J. et al. *Cancer* 73(3 Suppl.): 1023-32, 1994. The biologic window for chimeric L6 radioimmunotherapy.
Dickson S. *Gen. Engr. News* 5(3): 1, Mar. 1985. Scientists produce chimeric monoclonal Abs.
Eary J.F. et al. *J Nucl. Med.* 31(8): 1257-68, 1990. Imaging and treatment of B-cell lymphoma.
Einfeld D.A. et al. *EMBO J.* 7: 711-17, 1988. Molecular cloning of the human B cell CD20 receptor predicts a hydrophobic protein with multiple transmembrane domains.
Eisenbeis C.F. et al. *Clin. Cancer Res.* 10: 6101-10, 2004. Combination immunotherapy of B-cell non-Hodgkin's lymphoma with rituximab and interleukin-2: a preclinical and phase I study.
Endo K. *Jpn. J. Cancer Chemother.* 26: 744-48, 1999. Current status of nuclear medicine in Japan.
Engel/ A. et al. *Ann. Hematol.* 77(suppl. 2): S180, abst. No. 717, 1998. Multicenter phase II study of the monoclonal anti-CD20 antibody rituximab (IDEC-C2B8) in patients with intermediate/high grade non-Hodgkin's lymphoma.
Fisher D.C. et al. *Blood* 92: 247a, abst. No. 1010, 1998. Phase 1 trial with CD40-activated follicular lymphoma cells: a novel cellular vaccine strategy for B cell malignancies.
Flinn I.W. et al. *Blood* 92(10 Suppl. 1): 648a, abst. No. 2678, Nov. 1998. In vivo purging and adjuvant immunotherapy with rituximab during PBSC transplant for NHM [sic].
Foon KA, "Laboratory and Clinical Applications of Monoclonal Antibodies for Leukemias and Non-Hodgkin's Lymphomas." Curr. Probl. Cancer 13(2): 57-128 (Mar./Apr. 1989).
Foran J.M. et al. *Br. I Haematol.* 102(1): 149, 1998. Immunotherapy of mantle cell lymphoma (MCL), lymphoplasmacytoid lymphoma (LPC) and Waldentrom's macroglobulinemia (WM), and small lymphocytic leukemia (SLL) with rituximab (IDECC2B8): preliminary results of an ongoing international multicentre trial.
Foran, et al., "Immunotherapy of recurrent follicular lymphoma (FL) with Rituximab (IDECCB8): Preliminary results of an ongoing UK multicentre trial", British Journal of Haematology, vol. 102, No. 1, p. 243, (1998).
Ford B. *The Cal-Gab: Quarterly Newsletter of the Cancer and Leukemia Group B* 7(1): 4-5, Spring 1998. Rituxan$^T$ (Rituximab).
Ford S.M. et al. *Highlights in Oncology Practice* 16(2): 40-50, 1998 Immunotherapeutic approaches to treatment of B-cell neoplasms: focus on unconjugated antibodies.
Fridik M.A. et al. *Ann. Hematol.* 74(1): 7-10, 1997. First-line treatment of Waldenstrom's disease with cladribine.
Friedberg J.W. et al. *Expert Rev. Anticancer Ther.* 4(1): 18-26, 2004. Iodine-131 tositumomab (Bexxaro): radioimmunoconjugate therapy for indolent and transformed B-cell non-Hodgkin's lymphoma.
Full prescribing information for Rituxan (rituximab). Revised Feb. 2010, pp. 1-35.
Garcia-Conde J et al: "Study to Evaluate the Efficacy and Safety of Rituximab (IDEC- C2B8) and CVP Chemotherapy in Low-Grade or Follicular B-Cell Lymphoma After Relapse. Preliminary Results at a Follow Up Period of 3 Months," Blood, vol. 94, No. 10 SUPPL. 1 PART 2, p. 261 b Nov. 15, 1999.
Gianni A.M. et al. *Blood* 102: 749-55, 2003. Long-term remission in mantle cell lymphoma following high-dose sequential chemotherapy and in vivo rituximab-purged stem cell autografting (R-HDS regimen).
Ginaldi L. et al. *I Clin. Pathol.* 51: 364-69, 1998. Levels of expression of CD19 and CD20 in chronic B leukaemias.
Golay J. et al. *Haematologica* 88: 1002-12, 2003. Rituximab-mediated antibody-dependent cellular cytotoxicity against neoplastic B cells is stimulated strongly by interleukin-2.

(56) References Cited

OTHER PUBLICATIONS

Golay J.T. et al. *J. Immunol.* 135(6): 3795-801, 1985. The CD20 (Bp35) antigen is involved in activation of B cells from the GO to the 01 phase of the cell cycle.
Goldenberg D.M. et al. *J. Clin. Oncol.* 9(4): 548-64, 1991 Imaging and therapy of gastrointestinal cancers with radiolabeled antibodies.
Gonzalez-Barca et al., "Low-dose subcutaneous interleukin-2 in patients with minimal residual lymphoid neoplasm disease," *Eur. J. Hemat.* 62(4): 231-238 (1999).
Gordon L.I. et al. *Blood* 94(10 Suppl. 1): 91a, abst. No. 396, 1999. ZEVALINTm (IDECY2B8) radioimmunotherapy of rituximab refractory follicular non-Hodgkin's lymphoma (NHL): interim results.
Gordon L.I. et al. *I Immunother*. 22(5): 459, 1999. Update on IDEC-Y2B8 (ZEvALINTM) radioimmunotherapy of B-cell NHL.
Greenberger J.S. et al. *Cancer Res.* 45(2):758-67, 1985. Effects of monoclonal antibody and complement treatment of human marrow on hematopoiesis in continuous bone marrow culture.
Greiner J.W. et al. *Science* 235(4791): 895-98, 1987. Recombinant interferon enhances monoclonal antibody-targeting of carcinoma lesions in vivo.
Gribben J.G. et al. *N Engl. I Med*. 325(22): 1525-32, 1991 Immunologic purging of marrow assessed by PCR before autologous bone marrow transplantation for B-cell lymphoma.
Grillo-Lopez A.J. et al. *Ann. Oncol.* 7(3 Suppl.): 57, abst. No. 195, 1996. Treatment (rx) of relapsed non-Hodgkin's lymphoma (NHL) using the 90-yttrium (90-Y) labeled anti-CD20 monoclonal antibody (MAB) IDEC-Y2B8: a phase I clinical trial (PI CT).
Grillo-Lopez A.J. et al. *Antibody Immunoconj. Radiopharm.* 8: 60, abst. No. 10, 1995. Treatment options for patients with relapsed low-grade or follicular lymphoma: the role of IDEC-C2B8.
Grillo-Lopez A.J. et al. *Blood* 86(10 Suppl. 1): 55a, abst. No. 207, 1995. Phase I study of IDEC-Y2B8: 90-yttrium labeled anti-CD20 monoclonal antibody therapy of relapsed non-Hodgkin's lymphoma.
Grillo-Lopez A.J. et al. *Br. J. Haematol.* 93(Suppl. 2): 283, abst. No. 1072, 1996. IDECC2B8 chimeric anti-CD20 antibody (MAB): safety and clinical activity in the treatment of patients (PTS) with relapsed low-grade or follicular (IWF:A-D) non-Hodgkin's lymphoma (NHL).
Grillo-Lopez A.J. IBC Int'l. Conference on Antibody Engineering, La Jolla, Dec. 1994. IDEC-C2B8 chimeric antibody and IDEC-Y2B8 radiolabeled antibody phase I and II studies in patients with non-Hodgkin's lymphoma (abstract of presentation).
Grossbard M.L. et al. *Blood* 80(4): 863-78, 1992. Monoclonal antibody-based therapies of leukemia and lymphoma.
Gura T. *Science* 278: 1041-42, 1997. Systems for identifying new drugs are often faulty.
Hagenbeek A. et al. *I Clin. Oncol.* 16(1): 41-47, 1998. Maintenance of remission with human recombinant interferon alfa-2a in patients with stages III and IV low-grade malignant non-Hodgkin's lymphoma. European Organization for Research and Treatment of Cancer Lymphoma Cooperative Group.
Hainsworth J.D. et al. *Blood* 95: 3052-56, 2000. Rituximab monoclonal antibody as initial systemic therapy for patients with low-grade non-Hodgkin lymphoma.
Hancock et al., "A monoclonal antibody against the c-erbB-2 protein enhances the cytotoxicity of cis-diamminediehloroplatinum against human breast and ovarian tumor cell lines," *Cancer Res.* 51(17): 4575-80 (1991).
Hancock MC et al., "A Monoclonal Antibody Against the C-Erbb-2 Protein Enhances the Cytotoxicity of Cis-Diamminedichloroplatinum Against Human Breast and Ovarian Tumor Cell Lines." Cancer Res. 51(17): 4575-80 (Sep. 1991).
Harris N.L. et al. *Blood* 54(5): 1361-92, 1994. A revised European-American classification of lymphoid neoplasms: a proposal from the international Lymphoma Study Group.
Harris N.L. et al. *I Clin. Oncol.* 17(12): 3835-49, 1999. World Health Organization classification of neoplastic diseases of the hematopoietic and lymphoid tissues: report of the Clinical Advisory Committee meeting—Airlie House, Virginia, Nov. 1997.

Hartwell L.H. et al. *Science* 278: 1064-68, 1997. Integrating genetic approaches into the discovery of anticancer drugs.
Hekman A. et al. *Ann. Rept. Netherlands Cancer Inst., Amsterdam*, pp. 47-48, 1993. Immunotherapy.
Herold M. et al. *Ann Hematol.* 79: 332-335, 2000. Successful treatment and re-treatment of resistant B-cell chronic lymphocytic leukemia with the monoclonal anti-CD20 antibody rituximab.
Hiddemann W. et al. *Blood* 88(11): 4085-89, 1996. Lymphoma classification—the gap between biology and clinical management is closing.
Hillmen P. et al. *Semin. Oncol.* 31(1 suppl. 2): 22-26, 2004. Advancing therapy for chronic lymphocytic leukemia—the role of rituximab.
Hochster et al., "Maintenance rituximab after cyclophosphamide, vincristine, and prednisone prolongs progression-free survival in advanced indolent lymphoma: Results of the randomized phase III ECOG1496 Study," *.1 Clin. Oncol.* 27(10): 1607-1614 (2009).
Hochster Howard S et al: "Maintenance Rituximab After CVP Results in Superior Clinical Outcome in Advanced Follicular Lymphoma (FL) : Results of the E1496 Phase III Trial From The Eastern Cooperative Oncology Group and The Cancer and Leukemia Group," Blood, vol. 106, No. 11, pt. 1, Nov. 1, 2005, p. 106A.
Hooijberg E. et al. *Cancer Res.* 55: 2627-34, 1995. Eradication of large human B cell tumors in nude mice with unconjugated CD20 monoclonal antibodies and interleukin 2.
Horning S.J. et al. *Blood* 100(11 part 1): 357a, abst. No. 1385, 2002. Rituximab treatment failures: tositumomab and Iodine I 131 tositumomab (Bexxar®) can produce meaningful durable responses.
Hurwitz E et al., "A Synergistic Effect Between Anti-Idiotype Antibodies and Antineoplastic Drugs in the Therapy of a Murine B-Cell Tumor." Intl. J. Cancer 37(5): 739-45 (May 1986).
IDEC Pharmaceuticals "IDEC Pharmaceuticals Announces Positive Preliminary Results for Pivotal Trial of IDEC-C2B8", press release, May 21, 1996 (USA). http://www.thefreelibrary.com/IDEC+PHARMACEUTICALS+ANNOUNCES+POSITIVE+PRELIMINARY+RESULTS+FOR . . . -a018307934.
IDEC Pharmaceuticals Corp. and Genentech, Inc., Product insert for RITUXAN® approved by U.S. Food and Drug Administration on Nov. 26, 1997.
IDEC Pharmaceuticals Corp., press release dated Dec. 9, 1996. IDEC Pharmaceuticals and Genentech announce positive final results for pivotal phase III trial of IDEC-C2B8 as single agent.
IDEC Pharmaceuticals Corp., U.S. Securities and Exchange Commission Form S-1 Registration Statement, 1991.
*IDEC Pharmaceuticals v. Corixa Corp.*, Case No. 01-1637-IEG [Doc. Nos. 486, 584] (S.D. Cal.) Oct. 14, 2003.
Imrie K. et al. *Curr. Oncol.* 6(4): 228-35, 1999. Use of rituximab in the treatment of lymphoma: an evidence summary.
International Non-Hodgkin's Lymphoma Prognostic Factors Project, "A Predictive Model for Aggressive Non-Hodgkin's Lymphoma," *N Engl. J Med* 329(14): 987-994 (1993).
Jain R.K. *Sci. Am*. 271(1): 58-65, 1994. Barriers to drug delivery in solid tumors.
Janakiraman N. et al. *Blood* 92(10 Suppl. 1): 337a, abst. No. 1384, Nov. 1998. Rituximab: correlation between effector cells and clinical activity in NHL.
Jazirchi A.R. et al. *Oncogene* 24: 2121-43, 2005. Cellular and molecular signal transduction pathways modulated by rituximab (rituxan, anti-CD20 mAb) in non-Hodgkin's lymphoma: implications in chemosensitization and therapeutic intervention.
Jensen M. et al. *Ann. Hematol.* 77: 89-91, 1998. Rapid tumor lysis in a patient with B-cell chronic lymphocytic leukemia and lymphocytosis treated with an anti-CD20 monoclonal antibody (IDEC-C2B8, rituximab).
Juweid M. et al. *Cancer Res.* 55(23 Suppl.): 5827s-5831s, 1995. Estimates of red marrow. dose by sacral scintigraphy in radioimmunotherapy patients having non-Hodgkin's lymphoma and diffuse bone marrow uptake.
Juweid M. et al. *Cancer Res.* 55(23 Suppl.): 5899s-5907s, 1995. Treatment of non-Hodgkin's lymphoma with radiolabeled murine, chimeric, or humanized LL2, an anti-CD22 monoclonal antibody.
Kaminski M. et al. *Antibody Immunoconj. Radiopharm.* 3(1): abst. No. 83, 1990. Radioimmunotherapy of advanced B-cell lymphoma with non bone marrow ablative doses of 131-I MB-1 antibody.

(56) References Cited

OTHER PUBLICATIONS

Kaminski M. et al. *Antibody Immunoconj. Radiopharm.* 4(1): 36, abst. No. 66, 1991. Phase I trial results of 131-1 antibody radioimmunotherapy (RAIT) of B-cell lymphoma.

Kaminski M. et al. *J. Clin. Oncol.* 10(11): 1696-1711, 1992. Imaging, dosimetry, and radioimmunotherapy with iodine 131-labeled anti-CD37 antibody in B-cell lymphoma.

Kaminski M. et al. *Proc. Amer. Soc. Clin. Oncol.* 9: 271, abst. No. 1051, 1990. Radioimmunodetection (RID) and non marrow ablative radioimmunotherapy (RIT) of B-cell lymphoma with 131-I MB-1 antibody.

Kaminski M. et al. Proc. Third Conf. on Radioimmunodetection and Radioimmunotherapy of Cancer, Princeton NJ, Nov. 15-17, 1990 (published at Antibody Immunoconj. Radiopharm. 4: 387, 1991), abst. No. 144. 131-1 anti-B1: Initial clinical evaluation in B-cell lymphoma.

Kaminski M.S. et al. *Antibody Immunoconj. Radiopharm.* 5(3): 345, abst. No. 57, 1992. Initial clinical radioimmunotherapy results with $^{131}$I-anti-B1 (anti-CD20) in refractory B-cell lymphoma.

Kaminski M.S. et al. *Blood* 76(10 Suppl. 1): 355a, abst. No. 1409, 1990. Phase I evaluation of 131-1 MB-1 antibody radioimmunotherapy (RIT) of B-cell lymphoma.

Kaminski M.S. et al. *Blood* 78(10 Suppl. 1): 43a, abst. No. 161, 1992. Radioimmunothcrapy (RIT) of refractory B-cell lymphoma with 131-I-anti-B1 (anti-CD20) antibody: promising early results using non-marrow ablative radiation doses.

Kaminski M.S. et al. *J Clin. Oncol.* 14(7): 1974-81, 1996. Iodine-131-anti-B1 radioimmunotherapy for B-cell lymphoma.

Kaminski M.S. et al. *N. Engl. J Med.* 329: 459-65, 1993. Radioimmunotherapy of B-cell lymphoma with [$^{131}$I]anti-B1 (anti-CD20) antibody.

Keating M. et al. *Semin. Oncol.* 27(6 suppl. 12): 86-90, 2000. High-dose rituximab therapy in chronic lymphocytic leukemia.

Kennedy et al., "Incidence and nature of CD20-negative relapses following rituximab therapy in aggressive B-cell non-Hodgkin's lymphoma: a retrospective review," *Br. .1 Haematol.* 119(2): 412-6 (2002).

Khan et al., "A phase 2 study of rituximab in combination with recombinant interleukin-2 for rituximab-refractory indolent non-Hodgkin's lymphoma," *Clin. Cancer Res.* 12(23):7046-53 (2006).

Khan et al., "A Phase 2 Study of Rituximab in Combination with Recombinant Interleukin-2 for Rituximab-Refractory Indolent Non-Hodgkin's Lymphoma," Clin Cancer Res 12(23):7046-7053 (2006).

Kimby, "Beyond immunochemotherapy: combinations of rituximab with cytokines interferon-alpha2a and granulocyte colony stimulating factor," *Semin. Oncol.* 29(2 Suppl. 6): 7-10 (2002).

King and Younes, "Rituximab: review and clinical applications focusing on non-Hodgkin's lymphoma," *Expert Rev. Anticancer Ther.* 1(2): 177-86 (2001).

Kinoshita T. et al. *J. Clin. Oncol.* 16(12): 3916, Dec. 1998. CD20-negative relapse in B-cell lymphoma after treatment with Rituximab.

Klarnet J.P. et al. *.1 Immunol.* 138(11): 4012-17, 1987. Antigen-driven T cell clones can proliferate in vivo, eradicate disseminated leukemia, and provide specific immunologic memory.

Knox S.J. et al. *Clin. Cancer Res.* 2: 457-70, 1996. Yttrium-90-labeled anti-CD20 monoclonal antibody therapy of recurrent B-cell lymphoma.

Knox S.J. et al. *I Immunother.* 16(2): 161, abst. No. 51, 1994. $^{90}$Y-anti-CD20 monoclonal antibody therapy (IDEC-Y2B8) for recurrent B cell lymphoma.

Knox S.J. et al. *I.J. Rad. Oncol. Biol.Phys.* 32: 215, 1995. $^{90}$Y-anti-CD20 monoclonal antibody therapy for recurrent B cell lymphoma.

Kuzel T. et al. *Cancer Biother.* 8(1): 3-16, 1993. A phase I escalating-dose safety, dosimetry and efficacy study of radiolabeled monoclonal antibody LYM-1.

L.e. Van Der Kolk et al., "Chimeric Anti-CD20 Monoclonal Antibody (Rituximab) Plus G-CSF in Relapsed B-Cell Lymphoma: A Phase I/II Clinical Trial", British Journal of Haematology, vol. 102, No. 1, Jul. 1998, p. 243.

Langmuir V.K. *NucL Med. Biol.* 19(2): 213-55, 1992. Radioimmunotherapy: clinical results and dosimetric considerations.

Larson S.M. et al. *Nucl. Med. Biol.* 16: 153-58, 1989. Comparison of bone marrow dosimetry and toxic effect of high dose $^{131}$1-labeled monoclonal antibodies administered to man.

Lauria F. et al. *Bone Marrow Transplant.* 18(1): 79-85, 1996 Immunologic and clinical modifications following low-dose subcutaneous administration of rIL-2 in non-Hodgkin's lymphoma patients after autologous bone marrow transplantation.

Leichner P.K. et al. *Front. Rad. Ther. Oncol.* 24: 109-20, 1990. Dosimetry and treatment planning in radioimmunotherapy.

Leichner P.K. et al. *Med. Phys.* 20(2): 529-34, 1993. Tumor dosimetry in radioimmunotherapy: methods of calculation for beta particles.

Levy R. et al. *Fed. Proc.* 42: 2650-56, 1983. Tumor therapy with monoclonal antibodies.

Li Tongdu (chief translator), Clinical Oncology, Anhui Science and Technology Publication, vol. 28-3, pp. 34-45, 1996 and English translation.

Ling N.R. et al. (in) *Leucocyte Typing III: White Cell Differentiation Antigens*, A.J. McMichael et al., eds., Oxford: Oxford Univ. Pr., 1987, pp. 302-35. B-cell and plasma cell antigens: new and previously defined clusters.

Link B.K. et al. *Proc. Amer. Soc. Clin. OncoL* 17: 3a, abst. No. 7, 1998. Phase II pilot study of the safety and efficacy of rituximab in combination with CHOP chemotherapy in patients with previously untreated intermediate- or high-grade NHL.

Link M.P. et al. *I Immunol.* 137(9): 3013-18, 1986. A unique antigen on mature B-cells defined by a monoclonal antibody.

Lipton J.M. et al. *Blood* 60(5 Suppl. 1): 170a, abst. No. 609, 1992. Distribution of B1, CALLA, 02 microglobulin and Ia on hematopoiesis supporting cells (HSC) in short and long-term cultures.

Lister, "The management of follicular lymphoma", Annals of Oncology, Supplement 2, vol. 2, pp. 131-135, (1991).

Liu A.Y. et al. *J. Immunol.* 139(10): 3521-26, Nov. 1987. Production of a mouse-human chimeric monoclonal antibody to CD20 with potent Fc-dependent biologic activity.

Lonberg N. et al. *Nature* 368: 856-59, 1994. Antigen-specific human antibodies from mice comprising four distinct genetic modifications.

Longo DL, "Immunotherapy for Non-Hodgkin's Lymphoma." Curr. Opin. Oncol. 8(5): 353-59 (Sep. 1996).

Lowman H.B. Slides presented at IBC Antibody Engineering Conference, Dec. 2, 2003. Differential activities in a series of humanized anti-CD20 antibodies.

Lum L.G. et al. *Blood* 69(2): 369-80, 1987. The kinetics of immune reconstitution after human marrow transplantation.

M.S. Czuczinan et al., "Chemoimmunotherapy of Low-Grade Lymphoma with the Anti-CD20 Antibody IDEC-C2B8 in Combination with Chop Chemotherapy", Cancer Investigation (abstract 53) 14(Suppl. 1):59-61 (1996).

Macey D.J. et al. *Front. Rad. Ther. Oncol.* 24: 123-31, 1990. A treatment planning program for radioimmunotherapy.

Macklis R.M. et al. *Antibody Immunoconj. Radiother.* 5(3): abst. No. 39, 1992. Induction of programmed cell death in malignant lymphomas after radioimmunotherapy.

Macklis R.M. et al. *Cancer* 73(3 Suppl.): 966-73, 1994. Radiobiologic studies of low-doserate $^{90}$Y-lymphoma therapy.

Maddy A.H. et al. *Immunol.* 68(3): 346-52, 1989. The role of cell maturation in the generation of phenotypic heterogeneity in B-cell chronic lymphocytic leukaemia.

Maloney D.C. et al. *Blood* 90(6): 2188-2195, 1997. IDEC-C2B8 (Rituximab) anti-CD20 monoclonal antibody therapy in patients with relapsed low-grade non-Hodgkin's lymphoma.

Maloney D.G. et al. *Blood* 80(6): 1502-1510, 1992. Monoclonal anti-idiotype antibody therapy of B-cell lymphoma: the addition of a short course of chemotherapy does not interfere with the antitumor effect nor prevent the emergence of idiotype-negative variant cells.

Maloney D.G. et al. *Blood* 84(8): 2457-66, 1994. Phase I clinical trial using escalating single-dose infusion of chimeric anti-CD20 monoclonal antibody (IDEC-C2B8) in patients with recurrent B-cell lymphoma.

(56) References Cited

OTHER PUBLICATIONS

Maloney D.G. et al. *Blood* 88(10: Suppl. 1): 637a, abst. No. 2635, 1996. The anti-tumor effect of monoclonal anti-CD20 antibody (mAb) therapy includes direct anti-proliferative activity and induction of apoptosis in CD20 positive non-Hodgkin's lymphoma (NHL) cell lines.
Mange et al., "Immunotherapy with rituximab following high-dose therapy and autologous stem-cell transplantation for mantle cell lymphoma," *Semin. Oncol.* 29(1 Suppl. 2): 56-69 (2002).
Marcus et al., "CVP chemotherapy plus rituximab compared with CVP as first-line treatment for advanced follicular lymphoma," *Blood* 105: 1417-1423 (2005).
Mariuzza et al. *Science.* 233: 747-53, 1986. Three-dimensional structure of an antigen-antibody complex at 2.8 A resolution.
Marquez S.D. et al. *I.J. Rad. Oncol. Biol. Phys.* 39: 327, abst. No. 2173, 1997. Hematological toxicity in radioimmunotherapy is predicted both by the computed absorbed whole body dose (cGy) and by the administered dose (mCi).
Marti G.E. et al. *Ann. N.Y. Acad. Sci.* 651: 480-83, 1992. CD20 and CD5 expression in B-chronic lymphocytic leukemia.
Marx J.L. *Science* 229(4712): 455-56, 1985. Antibodies made to order.
Masucci G. et al. *Med. Oncol. Tumor Pharmacother.* 8(3): 207-20, 1991. Chemotherapy and immunotherapy of colorectal cancer.
Mazza P. et al. *Bone Marrow Trans.* 23: 1273-78, 1999. Analysis of feasibility of myeloablative therapy and autologous peripheral stem cell (PBSC) transplantation in the elderly: an interim report.
McLaughlin P. et al. *Blood* 92(10 Suppl. 1): 414a-415a, abst. No. 1712, Nov. 1998. Efficacy controls and long-term follow-up for relapsed or refractory, low-grade or follicular (R-LG/F) NHL.
McLaughlin P. et al. *J. Clin. Oncol.* 16(8): 2825-33, Aug. 1998. Rituximab chimeric-antiCD20 monoclonal antibody therapy for relapsed indolent lymphoma: half of patients respond to a four-dose treatment program.
McLaughlin P. et al. *Oncology* 12(12): 1763-81, 1998. Clinical status and optimal use of rituximab for B-cell lymphomas.
Meredith R.F. et al. *J Nucl. Med.* 33(9): 1648-53, 1992. Dose fractionation of radiolabeled antibodies in patients with metastatic colon cancer.
Mishell B.E. et al., eds. *Selected Methods in Cellular Immunology*, San Francisco: Freeman, 1980, p. 287-304. Modification and use of antibodies to label cell surface antigens.
Morrison and Peterson, "Combination chemotherapy in the treatment of follicular low-grade lymphoma," *Leuk. Lymphoma* 10 Suppl.: 29-33 (1993).
Morrison S. et al. *Proc. Nat'l Acad. Sci. USA* 81: 6851-54, 1984. Chimeric human antibody molecules: mouse antigen-binding domains with human constant region domains.
Morrison S.L. *Science* 229: 1202-07, 1985. Transfectomas provide novel chimeric antibodies.
Multani P.S. et al. *J. Clin. Oncol.* 16(11): 3691-3710, 1998. Monoclonal antibody-based therapies for hematologic malignancies.
Munro A. *Nature* 312: 597, 1984. Uses of chimeric antibodies.
Murray J.L. et al. *J Biol. Resp. Modifiers* 9(6): 556-63, 1990. Recombinant alpha-interferon enhances tumor targeting of an antimelanoma monoclonal antibody in vivo.
Murray J.L. et al. *J. NucL Med.* 26: 3328-29, 1985. The effect of radionuclide dose on imaging with indium-111-labeled anti P-97 monoclonal antibody.
Nadler L.M. et al. *Cancer Res.* 40(9): 3147-54, 1980. Serotherapy of a patient with a monoclonal antibody directed against a human lymphoma-associated antigen.
Nadler L.M. et al. *J. Clin. Invest.* 67: 134-140, 1981. A unique cell surface antigen identifying lymphoid malignancies of B cell origin.
Nadler L.M. et al. *J. Clin. Invest.* 74(2): 332-40, 1984. B cell origin of non-T cell acute lymphoblastic leukemia. A model for discrete stages of neoplastic and normal pre-B cell differentiation.
Nadler L.M. et al. *Lancet* 2(8400): 427-31, 1984. Anti-B1 monoclonal antibody and complement treatment in autologous bone-marrow transplantation for relapsed B-cell non-Hodgkin's lymphoma.
Nakamura K. et al. *Oncology* 50(1): 35-40, 1993. Effect of alpha-interferon on anti-alpha fetoprotein-monoclonal-antibody targeting of hepatoma.
Neuberger M.S. et al. *Nature* 314: 268-70, 1985. A hapten-specific chimacric IgE antibody with human physiological effector function.
Nielsen B. et al. *Eur. J Haematol.* 48(3): 146-51, 1992. Interferon-a-induced changes in surface antigens in a hairy-cell leukemia (JOK-1), and a Burkitt's lymphoma cell line (Daudi) during in vitro culture.
Non-Hodgkin's Lymphoma Pathologic Classification Project. *Cancer* 49(10): 2112-35, 1982. National Cancer Institute sponsored study of classifications of non-Hodgkin's lymphomas.
O'Brien S. *Blood* 92(10 Suppl 1): 105a, abst. No. 431, 1998. Phase I/II study of rituxan in chronic lymphocytic leukemia (CLL).
O'Brien S. et al. *N. Engl. J. Med.* 330(5): 319-22, 1994. Lack of effect of 2chlorodeoxyadenosine therapy in patients with chronic lymphocytic leukemia refractory to fludarabine therapy.
O'Brien S.M. et al. *J. Clin. Oncol.* 19: 2165-70, 2001. Rituximab dose-escalation trial in chronic lymphocytic leukemia.
Oettgen H.C. et al. *Hybridoma* 2(1): 17-28, 1983. Further biochemical studies of the human B-cell differentiation antigens B1 and 132.
Oncology Nursing Society. onsopcontent.ons.org/oes/online_ce/lymph/.05ciassification.htm, retrieved Feb. 25, 2003. Current therapies and future directions in the treatment of non-Hodgkin's lymphoma.
Orura et al., "Therapeutic future direction with new clinical trials for refractory lymphoid malignancies", *Journal of Japan Lymphoreticular System Society*, 1997, 37, 4, 285-296.
Ozato K. et al. *J. Immunol.* 126(1): 317-21, 1981. Monoclonal antibodies to mouse MHC antigens. III. Hybridoma antibodies reacting to antigens of the H-2b haplotype reveal genetic control of isotype expression.
Ozer et al., "Recombinant interferon-alpha therapy in patients with follicular lymphoma," *Cancer* 82(10): 1821-30 (1998).
Panka D.J. et al. *Proc. Nat'l. Acad. Sci.* 85: 3080-84, 1988. Variable region framework differences result in decreased or increased affinity of variant anti-digoxin antibodies.
Parker B.A. et al. *Cancer Res.* 50(3): 1022s-1028s, 1990. Radioimmunotherapy of human 13-cell lymphoma with $^{90}$Y-conjugated antiidiotype monoclonal antibody.
Pearson J.W. et al. *Cancer Res.* 49(18): 4990-95, 1989 Enhanced therapeutic efficacy of an immunotoxin in combination with chemotherapy against an intraperitoneal human tumor xenograft in athymic mice.
Petryk M. et al. *Oncologist* 6: 317-26, 2001. ASCO 2001: Critical commentaries: Hematologic malignancies.
Pietersz G.A. et al. *Immunol. Cell. Biol.* 65(2): 111-25, 1987. The use of monoclonal antibody conjugates for the diagnosis and treatment of cancer.
Piro L. et al. *Blood* 90(10 Suppl. 1): 510a, abst. No. 2272, 1997. RITUXAN™ (rituximab, IDEC-C2B8): Interim analysis of a phase II study of once weekly times 8 dosing in patients with relapsed low-grade or follicular non-Hodgkin's lymphoma.
Piro L.D. et al. *Ann. Oncol.* 10: 655-61, 1999. Extended Rituximab (anti-CD20 monoclonal antibody) therapy for relapsed or refractory low-grade or follicular non-Hodgkin's lymphoma.
Pitini et al. "Interleukin-2 and Lymphokine-Activated Killer Cell Therapy in Patients with Relapsed B-Cell Lymphoma Treated with Rituximab," Clin Cancer Res 13(18):5497 (2007).
Pitini et al., "Interleukin-2 and lymphokine-activated killer cell therapy in patients with relapsed B-cell lymphoma treated with rituximab," *Clin. Cancer Res.* 13(18): 5497 (2007).
Polyak M.J. et al. *Blood* 99: 3256-62, 2002. Alanine-170 and praline-172 are critical determinants for extracellular CD20 epitopes; heterogeneity in the fine specificity of CD20 monoclonal antibodies is defined by additional requirements imposed by both amino acid sequence and quaternary structure.
Press 0. et al. *Proc. Amer. Soc. Clin. Oncol.* 5: 221, abst. No. 864, 1986. Serotherapy of malignant B cell lymphomas with monoclonal antibody 1F5 (anti-CD20).

(56) References Cited

OTHER PUBLICATIONS

Press O.W. *Cancer I Sci. Amer.* 4(Suppl 2): S19-S26, Jul. 1998. Prospects for the management of non-Hodgkin's lymphomas with monoclonal antibodies and immunoconjugates.

Press O.W. et al. *Adv. Exp. Med. Biol.* 303: 91-96, 1991. Radiolabeled antibody therapy of human B cell lymphomas.

Press O.W. et al. *Blood* 69(2): 584-91, 1987. Monoclonal antibody 1F5 (anti-CD20) serotherapy of human B cell lymphomas.

Press O.W. et al. *Cancer Res.* 49(17): 4906-12, 1989. Endocytosis and degradation of monoclonal antibodies targeting human B-cell malignancies.

Press O.W. et al. *J. Clin. Oncol.* 7(8): 1027-38, 1989. Treatment of refractory non-Hodgkin's lymphoma with radiolabeled MB-1 (anti-CD37) antibody.

Press O.W. et al. *Lancet* 346(8971): 336-40, 1995. Phase II trial of $^{131}$I-B1 (anti-CD20) antibody therapy with autologous stem cell transplantation for relapsed B cell lymphomas.

Press O.W. et al. *Proc. Amer. Soc. Clin. Oncol.* 17, abst. No. 9, May 1998. A phase I/II trial of high dose iodine-131-anti-B1 (anti-CD20) monoclonal antibody, etoposide, cyclophosphamide, and autologous stem cell transplantation for patients with relapsed B cell lymphomas.

Rai K.R. et al. (in) R. Hoffman, R., ed., *Hematology*, 2d. ed., Churchill Livingstone, 1995, Chapter 83, pp. 1308-1319. Chronic lymphocytic leukemia.

Rapoport et al., "Autotransplantation for advanced lymphoma and Hodgkin's disease followed by post-transplant rituxan/GM-CSF or radiotherapy and consolidation chemotherapy," *Bone Marrow Transplant.* 29(4): 303-12 (2002).

Rastetter et al., "Rituximab: expanding role in therapy for lymphomas and autoimmune diseases," Annu. Rev. Med., 55: 477-503 (2004).

Reff M.E. et al. *Blood* 83(2): 435-45, 1994. Depletion of B cells in vivo by a chimeric mouse human monoclonal antibody to CD20.

Reilly R.M. *Clin. Pharm.* 10: 359-75, 1991. Radioimmunotherapy of malignancies.

Robertson M.J. et al. *Blood* 79(9): 2229-36, 1992. Human bone marrow depleted of CD33-positive cells mediates delayed but durable reconstitution of hematopoiesis: Clinical trial of MY9 monoclonal antibody-purged autgrafts for the treatment of acute myeloid leukemia.

Robinson R. et al. *Human Antibody Hybrid* 2: 84-93, 1991 Chimeric mouse-human anti-carcinoma antibodies that mediate different anti-tumor cell biological activities.

Rottenburger C. et al. *Br. J. Haematol.* 106(2): 545-52, 1999. Clonotypic CD20+ and CD19+ B cells in peripheral blood of patients with multiple myeloma post high-dose therapy and peripheral blood stem cell transplantation.

Rudikoff S. et al. *Proc. Nat'l. Acad.Sci.* 79: 1979-83, 1982. Single amino acid substitution altering antigen-binding specificity.

Sahagan B.G. et al. *J. Immunol.* 137: 1066-74, 1986. A genetically engineered murine/human chimeric antibody retains specificity for human tumor-associated antigen.

Scharff M. *Harvey Lectures* 69: 125-42, 1974. The synthesis, assembly, and secretion of immunoglobulin: a biochemical and genetic approach.

Schlom J. et al. *J. Natl. Cancer Inst.* 82(9): 763-71, 1990. Advantage of dose fractionation in monoclonal antibody-targeted radioimmunotherapy.

Schwartz-Albiez R. et al. *J. Immunol.* 140(3): 905-14, 1988. The B cell-associated CD37 antigen (gp40-52). Structure and subcellular expression of an extensively glycosylated glycoprotein.

Seaver S. *Gen. Engr. News.* 19 and 21, 1982. Monoclonal antibodies in industry: more difficult than originally thought.

See-Lasley K. et al. *Manual of Oncology Therapeutics*, St. Louis: C.V. Mosby Co., pp. 44-71, 1981. Hodgkin's disease and non-Hodgkin's lymphoma.

Senter P.D. et al. *Adv. Exp. Med Biol.* 303: 97-105, 1991. Activation of prodrugs by antibody-enzyme conjugates.

Senter P.D. et al. *Cancer Res.* 49: 5789-92, 1989 Enhancement of the in vitro and in vivo antitumor activities of phosphorylated mitomycin C and etoposide derivatives by monoclonal antibody-alkaline phosphatase conjugates.

Senter P.D. *FASEB I* 4: 188-93, 1990. Activation of prodrugs by antibody-enzyme conjugates: a new approach to cancer therapy.

Shan D. et al. *Clin. Cancer Res.* 7(8): 2490-95, 2001. Synergistic effects of the fenretinide (4-HPR) and anti-CD20 monoclonal antibodies on apoptosis induction of malignant human B cells.

Sharkey R.M. et al. *Cancer Res.* 50(3): 964s-969s, 1990. Biological considerations for radioimmunotherapy.

Shulman M. et al. *Nature* 276(5685): 269-70, 1978. A better cell line for making hybridomas secreting specific antibodies.

Soiffer R.J. et al. *Blood* 79(2): 517-26, 1992. Clinical and immunologic effects of prolonged infusion of low-dose recombinant interleukin-2 after autologous and T-celldepleted allogeneic bone marrow transplantation.

Soiffer R.J. et al. *Blood* 84(3): 964-971, 1994. Effect of low-dose interleukin-2 on disease relapse after T-cell-depleted allogeneic bone marrow transplantation.

Srivastava S.C. et al. *Nucl. Med. Biol.* (*LI Rad. Appi. Instrum. B*) 18(6): 589-603, 1991. Progress in research on ligands, nuclides and techniques for labeling monoclonal antibodies.

Staudt L.M. et al. Manuscript from pubmedcentral at NIH, edited paper published at *Adv. Immunol.* 87: 163-208, 2005. The biology of human lymphoid malignancies revealed by gene expression profiling.

Stenbygaard L.E. et al. *Breast Cancer Res. Treatment* 25: 57-63, 1993. Toremifene and tamoxifen in advanced breast cancer—a double-blind cross-over trial.

Stewart J.S.W. et al. *Int. J Cancer* Suppl. 3: 71-76, 1988. Intraperitoneal $^{131}$I-And$^{9\circ}$Y-labelled monoclonal antibodies for ovarian cancer: pharmacokinetics and normal tissue dosimetry.

Sun L.K. et al. *Hybridoma* 5(Suppl. 1): S17-20, 1986 Chimeric antibodies with 17-1A-derived variable and human constant regions.

Tan L.K. et al. *J. Immunol.* 135: 3564-67, 1985. A human-mouse chimeric immunoglobulin gene with a human variable region is expressed in mouse myeloma cells.

Tedder T.F. et al. *Eur J Immunol.* 16(8): 881-87, 1986. Antibodies reactive with the B1 molecule inhibit cell cycle progression but not activation of human B lymphocytes.

Tedder T.F. et al. *J Immunol.* 141(12): 4388-94, 1988. Cloning of a complementary DNA encoding a new mouse B lymphocyte differentiation antigen, homologous to the human B1 (CD20) antigen, and localization of the gene to chromosome 19.

Tedder T.F. et al. *J. Immunol.* 135(2): 973-79, 1985. The B cell surface molecule B1 is functionally linked with B cell activation and differentiation.

Teeling J.L. et al. *Blood* 104: 1793-1800, 2004. Characterization of new human CD20 monoclonal antibodies with potent cytolytic activity against non-Hodgkin lymphomas.

Teeling J.L. et al. *J Immunol.* 277: 362-71, 2006. The biological activity of human CD20 monoclonal antibodies is linked to unique epitopes on CD20.

Tobinai K. et al. *Ann. Oncol.* 9(5): 527-34, 1998. Feasibility and pharmacokinetic study of a chimeric anti-CD20 monoclonal antibody (IDEC-C2B8, rituximab) in relapsed B-cell lymphoma. The IDEC-C2B8 Study Group.

Trcon et al., "Interferon-Gamma Induces CD20 Expression on Multiple Myeloma Cells via Induction of Pu.1 and Augments Rituximab Binding to Myeloma Cells," Oncology 14(31): Abstract #521 (2000).

Tsai D.E. et al. *Blood* 92(10 Suppl. 1): 415a, abst. No. 1713, Nov. 1998. Progressive intermediate grade non-Hodgkin's lymphoma after high dose therapy and autologous peripheral stem cell transplantation (PSCT) has a high response rate to rituximab.

Tsai D.E. et al. *Bone Marrow Transplant.* 24(5): 521-26, 1999. Rituximab (anti-CD20 monoclonal antibody) therapy for progressive intermediate-grade non-Hodgkin's lymphoma after high-dose therapy and autologous peripheral stem cell transplantation.

Tsai D.E. et al. *Clin. Lymphoma Myeloma* 1(1): 62-66, 2000. Progressive intermediate-grade non-Hodgkin's lymphoma after high-dose therapy and autologous peripheral stem-cell transplantation: changing the natural history with monoclonal antibody therapy.

(56) References Cited

OTHER PUBLICATIONS

Uckun F.M. et al. *Cancer Res.* 45(1): 69-75, 1985. Increased efficiency in selective elimination of leukemia cells by a combination of a stable derivative of cyclophosphamide and a human B-cell-specific immunotoxin containing pokeweed antiviral protein.

Urlaub G. et al. *Som. Cell. Mot Genet.* 12(6): 555-66, 1986. Effect of gamma rays at the dihydrofolate reductase locus: deletions and inversions.

van der Kolk L.E. et al. *Blood* 92(10 Suppl. 1): 241b, abst. No. 4037, Nov. 1998.Chimeric anti-CD20 monoclonal antibody (rituximab) plus G-CSF in relapsed B-cell lymphoma: a phase I/II clinical trial.

van der Kolk L.E. et al. *Blood* 92(10 Suppl. 1): 512a-513a, abst. No. 2284, 1997. Phase I/II clinical trial to evaluate the safety and efficacy of a chimeric anti-CD20 monoclonal antibody (rituximab) and G-CSF given weekly to patients with relapsed B-cell lymphoma.

Vartholomatos G. et al. *Acta Haematol.* 102: 94-98, 1999. Rituximab (anti-CD20 monoclonal antibody) administration in a young patient with resistant B-prolymphocytic leukemia.

Venugopal P. et al. *Blood* 92(10 Suppl. 1): 247a, abst. No. 1009, Nov. 1998. Upregulation of CD20 expression in chronic lymphocytic leukemia (CLL) cells by in vitro exposure to cytokines.

Verkh L.I. et al. *Proc. Amer. Soc. Clin. Oncol.* 17: abst. No. 154, 1998. Dosimetry results of ONCOLYMTm in the treatment of refractory B cell non-Hodgkin's lymphoma (NHL).

Vey N. et al. *Leuk. Lymphoma* 221(1-2): 107-14, 1996. A pilot study of autologous bone marrow transplantation followed by recombinant interleukin-2 in malignant lymphomas.

Vose J.M. et al. *J Clin. Oncol.* 19(2): 389-97, 2001. Phase II study of rituximab in combination with chop chemotherapy in patients with previously untreated, aggressive non-Hodgkin's lymphoma.

Voso et al., "In vivo depletion of B cells using a combination of high-dose cytosine arabinoside/mitoxantrone and rituximab for autografting in patients with non-Hodgkin's lymphoma," *Br. J Haematol* 109(4): 729-35 (2000).

Wadler S. et al. *Semin. Oncol.* 19(2 Suppl. 3): 45-48, 1992. Principles in the biomodulation of cytotoxic drugs by interferons.

Wahl R.L. et al. *J Nucl. Med.* 31(5): 852, abst. No. 622, 1990. Radioimmunotherapy of B-cell lymphoma with 1131 MB-1 monoclonal antibody.

Wahl R.L. et al. *Proc. Amer. Soc. Clin. Oncol.* 17: 40a, abst. No. 156, May 1998. Successful re-treatment of non-Hodgkin's lymphoma (NHL) with iodine-131 anti-BI antibody.

Welte K. et al. *Blood* 64: 380-85, 1984. Defective interleukin 2 production in patients after bone marrow transplantation and in vitro restoration of defective T lymphocyte proliferation by highly purified interleukin 2.

Wessels B.W. et al. *Med. Phys.* 11(5): 638-45, 1984. Radionuclide selection and model absorbed dose calculations for radiolabel ed tumor associated antibodies.

White C.A. et al. *Ann. Oncol.* 10(3 Suppl): 64, abst. No. 215, 1999. Radioimmunotherapy of relapsed or refractory non-Hodgkin's lymphoma (NHL): IDEC-Y2B8 phase I/II $^{90}$yttrium trial.

White C.A. et al. *Ann. Rev. Med.* 52: 125-45, 2001. Antibody-targeted immunotherapy for treatment of malignancy.

White C.A. et al. *Blood* 87(9): 3640-49, 1996. Radioimmunotherapy of relapsed B-cell lymphoma with Yttrium 90 anti-idiotype monoclonal antibodies.

White C.A. et al. *Eur. J. Cancer* 35: S57, abst. No. 107, 1999. Zevalin™ radioimmunotherapy of relapsed or refractory non-Hodgkin's lymphoma.

White CA et al., "Anti-Cd20 Monoclonal Antibodies as Novel Treatments for Non-Hodgkin's Hodgkin's Lymphoma." *Pharm. Sci. Tech. Today* 2(3): 95-101 (Mar. 19991 White CA, et al., "Idec-C2b8-Induced B Cell Depletion is Not Associated With Significant Immune Suppression or Infection." *Eur. J. Cancer* 33(S8): 5266, Abstract 1203 (Sep. 1997).

Winkler U. et al. *Blood* 92(10 Suppl. 1): 285b, abst. No. 4228, Nov. 1998. Severe side effects in patients with B-cell chronic lymphocytic leukemia (CLL) and lymphocytosis treated with the monoclonal anti-CD20 antibody rituximab.

Winkler U. et al. *Blood* 94: 2217-24, 1999. Cytokine-release syndrome in patients with B-cell chronic lymphocytic leukemia and high lymphocyte counts after treatment with an antiCD20 monoclonal antibody (rituximab, IDEC-C2B8).

Wiseman G. et al. *Blood* 92(10 Suppl. 1): 417a, abst. No. 1721, Nov. 1998. IDEC-Y2B8 radioimmunotherapy: baseline bone marrow involvement and platelet count are better predictors of hematologic toxicity than dosimetry.

Wiseman G. et al. *Cancer Biother. Radiopharm.* 13(1): 59, abst. No. 22, 1998. Radioimmunotherapy of relapsed non-Hodgkin's lymphoma (NHL) with IDEC-Y2B8 90yttrium anti-CD20 monoclonal antibody.

Wiseman G. et al. *Cancer Biother. Radiopharm.* 13(4): 317, abst. No. 51, 1998. IDECY2B8 radioimmunotherapy of relapsed non-Hodgkin's lymphoma (NHL): interim analysis.

Wiseman G. et al. *Cancer Biother. Radiopharm.* 14(4): 315, abst. No. 2, 1999. 90Yttrium labelled IDEC Y2B8 anti-CD20 radioimmunotherapy.

Wiseman G. et al. *Proc. Amer. Soc. Clin. Oncol.* 17, 1998. Radioimmunotherapy of relapsed non-Hodgkin's lymphoma (NHL) with IDEC-Y2B8 $^{90}$yttrium radioimmunotherapy.

Wiseman G.A. et al. *Blood* 92(10 Suppl. 1): 510a, abst. No. 2273, Nov. 1998. IDEC-Y2B8 ($^{90}$Y conjugated anti-CD20) dosimetry calculated from $^{111}$In anti-CD20 in patients with low and intermediate grade B-cell non-Hodgkin's lymphoma (NHL) emphasis on bone marrow (BM).

Wiseman G.A. et al. *Blood* 94(10 Suppl. 1): 92a, abst. No. 403, 1999. ZEVALINT$^M$ biodistribution and dosimetry estimated normal organ absorbed radiation doses are not affected by prior therapy with rituximab.

Wiseman G.A. et al. *Clin. Cancer Res.* 5(Suppl.): 3281s-3286s, 1999. Radioimmunothcrapy of relapsed non-Hodgkin's lymphoma with Zcvalin, a $^{90}$Y-labeled anti-CD20 monoclonal antibody.

Wiseman G.A. et al. *I.J. Oncol. Biol. Phys.* 42(1 Suppl.): 130, abst. No. 11, 1998. IDECY2B8 ($^{90}$yttrium ibritumomab tiuxetan) radioimmunotherapy safety results in relapsed or chemotherapy refractory non-Hodgkin's lymphoma patients treated at reduced doses because of pre-existing thrombocytopenia.

Wiseman G.A. et al. *I.J. Oncol. Biol. Phys.* 45(3 Suppl.): 390, abst. No. 2217, 1999. IDECY2B8 (90yttrium(90yttriumibritumomab tiuxctan) radioimmunothcrapy safety results in relapsed or chemotherapy refractory non-Hodgkin's lymphoma patients treated at reduced doses because of pre-existing thrombocytopenia.

Wiseman G.A. et al. *J NucL Med.* 38(5 Suppl.): 251, abst. No. 1062, 1997. Y-90 anti-CD20 monoclonal antibody (IDEC-Y2B8) dosimetry calculated from In-111 anti-CD20 in patients with low and intermediate grade B-cell non-Hodgkin's lymphoma.

Wiseman G.A. et al. *J NucL Med.* 39(5 Suppl.): 185P, abst. No. 836, 1998. Whole-body gamma camera image quantification from multiple camera types for radioisotope therapy dosimetry.

Wiseman G.A. et al. *Proc. Amer. Soc. Clin. Oncol.* 18: 4a, abst. No. 13, 1999. Therapeutic index of IDEC-Y2B8 radioimmunotherapy: up to 850 fold greater radiation dose to tumor than normal organs.

Witherspoon R.P. et al. *Semin. Hematol.* 21(1): 2-10, 1984. Immunologic reconstitution after human marrow grafting.

Witzig T. et al. *Blood* 90(10 Suppl. 1): 586a, abst. No. 2606, 1997. IDEC-Y2B8 $^{90}$tyttrium anti-CD20 radioimmunotherapy of relapsed non-Hodgkin's lymphoma (NHL): interim results of a phase I/II trial.

Witzig T. et al. *Blood* 92(10 Suppl. 1): 417a, abst. No. 1722, Nov. 1998. IDEC-Y2B8 radioimmunotherapy: responses in patients with splenomegaly.

Witzig T.E. et al. *Am. J. Clin. Pathol.* 101: 312-17, 1994. Measurement of the intensity of cell surface antigen expression in B-cell chronic lymphocytic leukemia.

Witzig T.E. et al. *Blood* 94(10 Suppl. 1): 631a, abst. No. 2805, 1999. Prospective randomized controlled study of ZEVALIN™ (IDEC-Y2B8) radioimmunotherapy compared to rituximab immunotherapy for B-cell NHL: report of interim results.

Witzig T.E. et al. *Blood* 94(10 Suppl. 1): 92a, abst. No. 400, 1999. Reduced-dose ZEVALIN™ radioimmunotherapy for relapsed or refractory B-cell non-Hodgkin's lymphoma (NHL) patients with pre-existing thrombocytopenia: report of interim results of a phase II trial.

(56) References Cited

OTHER PUBLICATIONS

Witzig T.E. et al. *I Clin. Oncol.* 17(12): 3793-3803, 1999. Phase I/II trial of IDEC-Y2B8 radioimmunotherapy for treatment of relapsed or refractory CD20(+) B-cell non-Hodgkin's lymphoma.
Witzig T.E. et al. *I Immunother.* 21(6): 463, abst. No. 2805, 1998. IDEC-Y2B8 radioimmunotherapy of relapsed or refractory non-Hodgkin's lymphoma.
Witzig T.E. et al. *J. Clin. Oncol.* 20(15): 3262-69, 2002. Treatment with ibritumomab tiuxetan radioimmunotherapy in patients with rituximab-refractory follicular non-Hodgkin's lymphoma.
Witzig T.E. et al. *J. Clin. Oncol.* 20: 2453-63, 2002. Randomized controlled trial of yttrium-90-labeled ibritumomab tiuxetan radioimmunotherapy versus rituximab immunotherapy for patients with relapsed or refractory low-grade, follicular, or transformed B-cell non-Hodgkin's lymphoma.
Witzig T.E. et al. *Proc. Amer. Soc. Clin. Oncol.* 18: 41a, abst. No. 152, 1999. Commonly used response criteria for non-Hodgkin's lymphoma (NHL) applied to IDEC-Y2B8 radioimmunotherapy trial: importance of "normal" lymph node size.
Yakoub-Agha et al., "Allogeneic bone marrow transplantation in patients with follicular lymphoma: a single center study," *Bone Marrow Transplant* 30(4): 229-34 (2002).
Yang H. et al. *Am. J. Hernatol* 62: 247-50, 1999. Tumor lysis syndrome occurring after the administration of rituximab in lymphoproliferative disorders: high-grade non-Hodgkin's lymphoma and chronic lymphocytic leukemia.
Yokota S. et al. *Cancer Res.* 50: 32-37, 1990. Synergistic potentiation of in vivo antitumor activity of anti-human T-leukemia immunotoxins by recombinant a-interferon and daunorubicin.
Clinical Trials (PDQ®); "Phase III Randomized Study of CHOP (Cyclophosphamide, Doxorubicin, Vincristine, and Prednisone) With or Without Rituximab in Older Patients With Diffuse Mixed, Diffuse Large, or Immunoblastic Large Cell Non-Hodgkin's Lymphoma" http://www.cancer.gov/clinicaltrials/search/view?cdrid=65935&version=HealthProfessional; First Published: Jan. 1, 1998; Last Modified: Aug. 27, 2010; Retrieved: Jan. 14, 2013; pp. 1-6.
FDA label of Doxorubicin Hydrochloride for injection USP, pp. 1-22, 2010.
Arico et al., "Long term survival after heart transplantation for doxorubicin induced cardiomyopathy", *Arch Dis Child* 66, 1991, pp. 985-986.
Bentley, M. and Taylor, K., "Low-grade non-Hodgkin's lymphoma—Biology and therapeutic approaches", *Australian and New Zealand Journal of Medicine* 27, 1997, pp. 150-155.
Buske et al., "Monoclonal Antibody Therapy for B Cell Non-Hodgkin's Lymphomas: Emerging Concepts of a Tumour-targeted Strategy", *European Journal of Cancer*, vol. 35(4), 1999, pp. 549-557.
Dana et al., "Long-Term Follow-Up of Patients With Low-Grade Malignant Lymphomas Treated With Doxorubicin-Based Chemotherapy or Chemoimmunotherapy" *J. Clinical Oncology*, vol. 11, No. 4 (Apr.) 1993, pp. 644-651.
Hainsworth et al., "Rituximab Induction and Maintenance Therapy in Patients (pts) with Previously Untreated Low-Grade Non-Hodgkin's Lymphoma (NHL): Preliminary Results of a Minnie Pearl Cancer Research Network Phase II Trial" *Proceedings of the ASCO*, vol. 18 (Abstract #105) 1999, p. 29a ; with e-mail from Ascopubs [ascobus@asco.org] dated Mar. 11, 2013, 1 pg, stating that the 1999 Program Proceedings vol. 18 was made available to the public on May 15, 1999.
Hiddemann, "Non-Hodgkin's Lymphomas—Current Status of Therapy and Future Perspectives", *European Journal of Cancer* vol. 31A (13/14) 1995, pp. 2141-2145.
Hochster, H.S., et al., "Results of E1496: A phase III trial of CVP with or without maintenance rituximab in advanced indolent lymphoma (NHL)", Journal of Clinical Oncology, 2004 ASCO Annual Meeting, vol. 22, No. 14S (Jul. 15 Supplemental), 2004: 6502, pp. 1-2.
Leget et al., "Use of rituximab, the new FDA-approved antibody", *Current Opinion in Oncology* 10, 1998, pp. 548-551.

McLaughlin P. et al. *J. Clin Oncol.* 16(8): 2825-2833, Aug. 1998. "Rituximab chimericanti-CD20 monoclonal antibody therapy for relapsed indolent lymphoma: half of patients respond to a four-dose treatment program" (Previously submitted); with e-mail from publisher Glenn Landis dated Nov. 5, 2012, 1 page, stating the official publication date thereof was Aug. 1, 1998.
Misset et al., "Dose-finding study of docetaxel and doxorubicin in first-line treatment of patients with metastatic breast cancer", *Annals of Oncology* 10, 1999, pp. 553-560.
Monnereau et al., "L'interféron alpha dans le traitement des lymphomes non hodgkiniens de faible malignité", *Bulletin du Cancer*, vol. 85, No. 10, 1998, pp. 855-65, in French with English translation, pp. 1-19.
Onrust et al., "Rituximab" *Drugs* 58(1), 1999, pp. 79-88.
Palmieri et al., "Maintenance therapy with recombinant interferon alpha-2B (αIFN) in prognostically unfavourable aggressive non-Hodgkin's lymphomas (NHL)" *Oncology Reports* 3: 1996, pp. 733-735.
Portlock, C.S. And Rosenberg, S.A., "Combination chemotherapy with cyclophosphamide, vincristine, and prednisone in advanced non-Hodgkin's lymphomas" *Cancer* 37(3); 1976, pp. 1275-1282.
Siddhartha, G. and Vijay, P., "R-CHOP versus R-CVP in the treatment of follicular lymphoma: a meta-analysis and critical appraisal of current literature". *J. Hematology & Oncology* 2:14, pp. 1-7 (Mar. 24, 2009) doi: 10.1186/1756-8722-2-14.
Steward et al. "Maintenance Chlorambucil After CVP in the Management of Advanced Stage, Low-Grade Histologic Type Non-Hodgkin's Lymphoma" *Cancer* 61(3) 1988, pp. 441-447.
Sweetenham et al., "Cost-minimization analysis of CHOP, fludarabine and rituximab for the treatment of relapsed indolent B-cell non-Hodgkin's lymphoma in the U.K.", *British Journal of Haematology* 106, 1999, pp. 47-54.
Davis et al., "Anti-Idiotype Antibodies Can Induce Long-Term Complete Remissions in Non-Hodgkin's Lymphoma Without Eradicating the Malignant Clone", *Blood, vol. 92, No. 4* (Aug. 15), 1998: pp. 1184-1190.
Feugier et al., "Long-Term Results of the R-CHOP Study in the Treatment of Elderly Patients With Diffuse Large B-Cell Lymphoma: A Study by the Groupe d'Etude des Lymphomes de l'Adult"; *Journal of Clinical Oncology*, vol. 23, No. 18, Jun. 20, 2005, pp. 4117-4126.
A. Gopal et al., "Clinical applications of anti-CD20 antibodies", *J. Lab Clin Med; 134*:, 1999, pp. 445-450.
Guan, et al., "Rituximab in combination with CHOP, an effective and well-tolerated salvage regimen for diffuse large B-Cell Lymphoma", *Chinese Journal of Clinical Oncology*, vol. 4, No. 4, pp. 264-267, (2007).
Habermann, et al., "Rituximab-CHOP versus CHOP alone or with maintenance rituximab in older patients with diffuse large B-cell lymphoma", [PUBMED Abstract] *J Clin Oncol* 24 (19): 3121-7, 2006.
Morrison, et al., "Maintenance rituximab (MR) compared to observation (OBS) after R-CHOP or CHOP in older patients (pts) with diffuse large B-cell lymphoma (DLBCL): An Intergroup E4494/C9793 update", [Abstract] *J Clin Oncol* 25 (Suppl 18): A-8011, 443s, 2007.
Cancer.Net, "Lymphoma—Non-Hodgkin", www.cancer.net/cancer-types/lymphoma-non-hodgkin/subtypes; Reviewed and approved by the Cancer.Net Editorial Board May 2012; pp. 1-6 (Retrieved Mar. 17, 2013).
ClinicalTrials.gov, "Combination Chemotherapy With or Without Monoclonal Antibody Therapy in Treating Patients With Stage III or Stage IV Low-Grade Non-Hodgkin's Lymphoma", http://clinicaltrials.gov/show/NCT00003204; Study Start Date: Mar. 1998, Primary Completion Date: May 2006, First Received: May 2, 2000; Last updated: Feb. 26, 2013; Last verified: Feb. 26, 2013; pp. 1-4 (Retrieved Mar. 4, 2013).
ECOG's Active Protocols: ECOG Protocols Active as of May 19, 1998, Internet Archive, Wayback Machine, http://web.archive.org/web/19980519084342/http://ecog. dfci.harvard.edu/~ecogdba/active_reports/Lymphoma.html; Revised: May 19, 1998; 1 page (Retrieved Mar. 4, 2013).

(56) References Cited

OTHER PUBLICATIONS

RITUXAN® Rituximab Prescribing Information, Initial US Approval: Nov. 1997; Med Guide Revision Date: Jul. 2012; Prescribing Information Revision Date: Oct. 2012; pp. 1-40.
RITUXAN® (Rituximab) ECOG 1496 Trial for Low-grade or Follicular Non-Hodgkin's Lymphoma, 2012, http://www.rituxan.com/hem/hcp/non-hodgkin/post-induction/ecog/index.html; pp. 1-3; (Retrieved 2012); Trial Design Published in Hochster et al., J. Clin. Oncol. 2009; 27:1607-1614.
MabThera® EU Marketing Authorization: EU/1/98/067/002; Summary of Product Characteristics; Date of first authorization: Jun. 2, 1998; Date of latest renewal: Jun. 2, 2008, pp. 1-94.
Roche press release, Investor Update, Basel, Jun. 7, 2004, "MabThera/Rituxan® maintenance therapy dramatically improves progression-free survival in patients with indolent Non-Hodgkin's Lymphoma (NHL)", http://www.roche.com/investors//ir_update/inv-update-2004-06-07d.html; pp. 1-3 (Retrieved Jan. 30, 2013).
Thompson Reuters Pharma™ "Drug Report: Rituximab", http://thomsonpharma.com; Update date: Mar. 28, 2011; pp. 1-4 (Retrieved 2011).
Clinical Trials (PDQ®); "Phase III randomized Study of CHOP (Cyclophosphamide, Doxorubicin, Vincristine, and Prednisone) With or Without Rituximab in Older Patients With Diffuse Mixed, Diffuse Large, or Immunoblastic Large Cell Non-Hodgkin's Lymphoma"; First Published: Jan. 1, 1998; Last Modified: Aug. 27, 2010; http://www.cancer.gov/clinicaltrials/search/view?cdrid=65935&version=HealthProfessional; pp. 1-7 (Retrieved Jan. 17, 2013).
Byrd et al., "Old and New Therapies in Chronic Lymphocytic Leukemia: Now is the Time for a Reassessment of Therapeutic Goals", Seminars in Oncology, vol. 25, No. 1 Feb. 1998; pp. 65-74.
Goldenberg DM, et al. "Characterization of New, Chimeric and Humanized, Anti-CD20 Monoclonal Antibodies, cA20 and hA20, with Equivalent Efficacy to Rituximab in-vitro and in Xenografted Human Non-Hodgkin's lymphoma." (Abstract #2260) *Poster Session: Biologic Therapy of Lymphomas: Laboratory Investigations held on Dec. 8, 2002*, 1 page. (Retrieved Sep. 30, 2004) http://www.abstracts2view.com/hemphiladelphia02/view.php?nu=HEM2L_1183.
Grossbard M.L. and Multani, P.S., "Clinical Status and Optimal Use of Rituximab for B-Cell Lymphomas", *Oncology* vol. 12(12); 1998, pp. 1-2, as published online by www.cancernetwork.com on Dec. 1, 1998 (Retrieved Feb. 4, 2013) http://www.cancernetwork.com/print/article/10165/66803?printable=true.
Grossbard M.L. and Multani, P.S. "The McLaughlin et al Article Reviewed", Dec. 1998, Oncology, 12(12):1769-1770.
Habermann, et al., "Rituximab-CHOP versus CHOP with or without maintenance rituximab in patients 60 years of age or older with diffuse large B-cell lymphoma (DLBCL): an update" *Blood (ASH Annual Meeting Abstracts) 104* (11): A-127, 2004. (Retrieved Oct. 14, 2011) http://www.hematologylibrary.org/ . . . HOR1=habermann &VOLUME=104&FIRSTINDEX=0&hits=10 &RESULTFORMAT=1&gca=ashmtg%3B104%2F11%2F127&al-lchb=.
Hultin et al., "CD20 (pan-B cell) antigen is expressed at a low level on a subpopulation of human T lymphocytes", Cytometry 1993; 14(2):196-204 (Abstract only—1 page), www.ncbi.nlm.nih.gov/pubmed/7679964 (Retrieved Mar. 26, 2013).
James, J.S. and Dubs, G., "FDA approves new kind of lymphoma treatment. Food and Drug Administration" *AIDS Treat News*, Dec. 5, 1997; (No. 284):2-3 (Abstract only), http://www.ncbi.nlm.nih.gov/pubmed/11364912 (Retrieved Feb. 4, 2013).
Lefrak et al., "A clinicopathologic analysis of adriamycin cardiotoxicity" *Cancer* 32(2) 1973, pp. 302-314 (Abstract only—pp. 1-3); article first published online. Jun. 27, 2006; http://onlinelibrary.wiley.com/doi/10.1002/1097-0142(197308)32:2<30 . . . (Retrieved Mar. 6, 2013).
McLaughlin, P. et al., "Clinical Status and Optimal Use of Rituximab for B-Cell Lymphomas", Dec. 1998, Oncology, 12(12):1763-1781.

Morrison, et al., "Dose intensity of CHOP alone or with rituximab in diffuse large B-cell lymphoma (DLBCL) in patients >60 years of age: an analysis of the intergroup trial (CALGB 9793, ECOG-SWOG 4494)", [Abstract] *Ann Oncol* 16 (Suppl 5): A-224, v102, 2005.
Pfreundschuh et al., "CHOP-like chemotherapy plus rituximab versus CHOP-like chemotherapy alone in young patients with good-prognosis diffuse large-B-cell lymphoma: a randomised controlled trial by the MabThera International Trial (MInT) Group", Lancet Oncol 2006; 7:379-91.
Chemocare.corn, "Oncovin", www.chemocare.com/chemotherapy/drug-info/Oncovin.aspx; pp. 1-6 (Mar. 2013) (Retrieved Mar. 25, 2013).
Maloney et al., "Newer Treatments for Non-Hodgkins Lymphoma: Monoclonal Antibodies", Oncology vol. 12, No. 10, Oct. 2, 1998, pp. 1-21 http://www.cancernetwork.com/display/article/10165/72098 (Retrieved 1998) Article also published in: Maloney et al., Oncology 12(Suppl 8):63-76 (1998).
Bodkin et al., "Pharmacokinetic analysis of serum concentrations of the chimeric anti-CD20 antibody IDEC-C2B8 in patients with relapsed B cell lymphoma", Proc Annu Meet Am Assoc Cancer Res 36:365 (#2175), Mar. 1995.
Brown S.L. et al., "Treatment of B-cell lymphomas with anti-idiotype antibodies alone and in combination with alpha interferon"; *Blood* 73:651-661, 1989.
Cabanillas, F. et al., "Anti-CD20 Antibody (MAB), IDEC-C2B8: Clearance of BCL-2 t(14;18) positive cells from peripheral blood (PB) and bone marrow (BM) in patients (PTS) with relapsed low-grade or follicular lymphoma (LG/F NHL)" Blood 88(10):91a (#351), Nov. 1996.
Cheson, B. et al., "Report of an International Workshop to Standardize Response Criteria for Non-Hodgkin's Lymphomas", J Clin Oncol 17(4):1244-53, Apr. 1999.
Czuczman M.S. et al., "Chemoimmunotherapy of Low-Grade Lymphoma with the Anti-CD20 Antibody IDEC-C2B8 in Combination with CHOP Chemotherapy", *Cancer Investigation* (Abstract 53) 14 (Suppl. 1): 59-61 (1996).
Czuczman M.S. et al., "IDEC-C2B8 (Rituximab) alone and in combination with CHOP in the treatment of low-grade B-cell lymphoma", Cancer Invest 16 (1 Suppl):21-22 (#17), 1998.
Czuczman M.S. et al., "IDEC-C2B8 and CHOP chemoimmunotherapy of low-grade lymphoma", Blood 86(10 suppl 1):55a (#206), Nov. 1995.
Czuczman, M.S. et al., "Rituxan™/CHOP Chemo immunotherapy in patients with low-grade or follicular (LG/F) non-Hodgkin's lymphoma (NHL)", J Immunother 20(5):401, Sep. 1997.
Czuczman, M.S. et al., "The Anti-CD20 Antibody (MAB) IDEC-C2B8 Clears Lymphoma Cells Bearing the t(14;18) Translocation (bcl-2) from the Peripheral Blood (PB) and Bone Marrow (BM) of a Proportion of Patients (PTS) with Low-Grade or Follicular (LG/F) Non-Hodgkin's Lymphoma (NHL)", J. Ann Oncol 7(5 Suppl):111 (#532P), Nov. 1996.
Czuczman, M.S. et al., "IDEC-C2B8 clears bcl-2 (t14;18) in patients (pts) with relapsed low grade or follicular lymphoma (LG/F NHL)", Proc Annu Meet Am Assoc Cancer Res 38:84 (#565), Mar. 1997.
Czuczman, M.S. et al., "Phase II Clinical Trial of IDEC-C2B8/CHOP Combination Therapy in Low Grade Lymphoma: Preliminary Results", Proc Am Soc Clin Oncol 14:401 (#1261), Mar. 1995.
Czuczman M.S. et al., "IDEC-C2B8/CHOP Chemoimmunotherapy in Patients with Low-Grade Lymphoma: Clinical BCL-2 (PCR) Final Results", Blood 88(10):453a (#1799), Nov. 1996.
Dallaire, B.K. et al., "IDEC-C2B8 (RITUXIMAB): Biology and preclinical studies", J Mol Med 75(7):B230-B231 (#256), Jul. 1997.
Flinn, I.W., et al, "Immunotherapy with rituximab during peripheral blood stem cell transplantation for non-Hodgkin's lymphoma." Biol Blood Marrow Transplant. 2000;6(6):628-32.
Gladstone, D.E. et al, "High-dose cyclophosphamide and rituximab without stem cell transplant: a feasibility study for low grade B-cell, transformed and mantle cell lymphomas." Leuk Lymphoma. Nov. 2011;52(11):2076-81.
Grillo-López, A.J., "Rituximab: An Insider's Historical Perspective", *Seminars in Oncology*, vol. 27, No. 6, Suppl 12 (Dec. 2000); pp. 9-16.

(56) References Cited

OTHER PUBLICATIONS

Grillo-López, A.J. et al., "Overview of the Clinical Development of Rituximab: First Monoclonal Antibody Approved for the Treatment of Lymphoma", Seminars in Oncology, vol. 26, No. 5, Suppl 14 (Oct. 1999); pp. 66-73.

Grillo-López, A.J. et al., "Monoclonal Anti-CD20 Antibody (IDEC-C2B8) Therapy of B-Cell Non-Hodgkin's Lymphoma—Pre Clinical Development and Early Clinical Results", Proc Eighth NCT/EORTC Symposium On New Drugs In Cancer Therapy, p. 112 (#175) Mar. 1994.

Grillo-López, A.J. et al., "Development of Response Criteria (RC) for Low-Grade or Follicular Lymphomas (LG/F NHL) and Application in a 166 Patient Study", 26th Annual Meeting of the International Society for Experimental Hematology, Exp Hematol Abstract 17, vol. 25, No. 8, pp. 732, Aug. 1997.

Grillo-López, A.J., "Rituximab (IDEC-C2B8): Development of an anti-CD20 monoclonal antibody (MAB) for the treatment of non-Hodgkin's lymphoma." Ann Hematol 77(Suppl 1):A7 (#26), 1998.

Grillo-López, A.J. et al., "Preclinical and Early Clinical Development of the Anti-CD20 Monoclonal Antibody IDEC-C2B8", Ninth International Conference on Monoclonal Antibody Immunoconjugates for Cancer, Antibody Immunoconjugates, and Radiopharmaceuticals, vol. 7, No. 1, Abstract 64, Spring 1994.

Grillo-López, A.J. et al., "IDEC-C2B8: Clinical development of a chimeric anti-CD20 antibody for the treatment of patients (pts) with relapsed low-grade or follicular NHL", Abstract 190, Ann Oncol 7(1 Suppl):56, Mar. 1996.

Grillo-López, A.J. et al., "Rituxan™: Anti CD20 monoclonal antibody for the treatment of lymphoma." Exp Hematol 26(8):746 (#233), Aug. 1998.

Grillo-López, A.J. et al., "Overview of the safety and efficacy of IDEC-C2B8 including activity in patient populations with poor prognosis low grade or follicular NHL (LG/F NHL)", J. Mol. Med. Abstract 259, vol. 75, No. 7, Jul. 1997, pp. B231-B232.

Grillo-López, A.J. et al., "IDEC-C2B8 (RITUXIMAB): Clinical Activity in Poor Prognosis Subgroups of Relapsed Low-Grade or Follicular Lymphoma", 26th Annual Meeting of the International Society for Experimental Hematology, EXP HEMATOL Abstract 406, vol. 25, No. 8, Aug. 1997, pp. 846.

Grillo-López, A.J. et al., Anti-CD20 Chimeric Antibody, IDEC-C2B8: Safety and Clinical Activity in the Treatment of Relapsed Low Grade or Follicular (IWF: A-D) Lymphomas (LG-F/NHL), 25th Annual Meeting of the International Society for Experimental Hematology, Exp Hematol Abstract 691, vol. 24, No. 9, Aug. 1996, pp. 1150.

Grillo-López, A.J., et al., "Clinical activity of the monoclonal antibody (MAB) IDEC-C2B8 in patients (pts) with relapsed low-grade or follicular NHL (R-LG/F NHL)", Eur J Cancer 33(S8):S260-S261 (#1179), Sep. 1997.

Grillo-López, A.J. et al., "Response criteria (RC) for NHL: Importance of "normal" lymph node (LN) size and correlations with response." Blood 92(10 Suppl 1):412a (#1701), Nov. 1998.

Grillo-López, A.J., "IDEC-C2B8: Initial Phase II Results in Patients with B-Cell Lymphoma", Journal of Immunotherapy with Emphasis on Tumor Immunology, vol. 16, No. 3, Oct. 1994, pp. 236.

Horning, S. et al., "Response criteria (RC) and quality assurance (QA) of responses in the evaluation of new therapies for patients (pts) with low-grade lymphoma (LG NHL)", Proc Am Soc Clin Oncol 16:18a (#62), May 1997.

Lazzarino, M. et al., "Immunochemotherapy with rituximab, vincristine and 5-day cyclophosphamide for heavily pretreated follicular lymphoma." Oncology. 2005;68(2-3):146-53.

Maloney, D.G., et al., "Initial Report on a Phase I/II Multiple Dose Clinical Trial of IDEC-C2B8 (Chimeric Anti-CD20) in Relapsed B-Cell Lymphoma", Proc Am Soc Clin Oncol 13:304 (#993) Mar. 1994.

Maloney, D.G., et al., "Phase I/II Clinical Trials of IDEC-C2B8 (Chimeric Anti-CD20 Antibody) in Relapsed B-Cell Lymphoma", Cancer Investigation, vol. 13, Suppl 1, pp. 31-32 (#24), 1995.

Maloney, D.G., et al., "Chimeric Anti-CD20 (IDEC-C2B8) Monoclonal Antibody Therapy of Low-Grade Lymphoma", Cancer Invest 15(1 Suppl):78-79 (#70), 1997.

Maloney, D.G., et al., "IDEC-C2B8 Anti-CD20 Antibody: Results of Long-Term Follow-Up of Relapsed NHL Phase II Trial Patients", Blood 86(10):54a (#205), Nov. 1995.

Maloney, D.G., et al., "IDEC-C2B8: Final report on a Phase II trial in relapsed non-Hodgkin's lymphoma", Blood 84(10) Supplement 1:169a (#661), 1994.

Maloney, D.G., et al., "Phase I Clinical Trial Using Escalating Single Dose Infusion of Chimeric Anti-CD20 Monoclonal Antibody (IDEC-C2B8) in Patients with Recurrent B-Cell Lymphoma)", Blood 82(10 Suppl 1): 445a (#1763), Nov. 1993.

McLaughlin, P. et al. "Efficacy controls and long-term follow-up of patients (PTS) treated with rituximab for relapsed or refractory, low-grade or follicular (R-LG/F) NHL", Blood 92(10 Suppl 1): 414a-415a, 1998.

McLaughlin P, et al., "A Phase III (PIII) pivotal trial of IDEC-C2B8 in patients (pts) with relapsed low-grade or follicular lymphoma."J Mol Med 75(7):B231 (#257), Jul. 1997.

McLaughlin P. et al., "Rituximab chimeric-antiCD20 monoclonal antibody therapy for relapsed indolent lymphoma: half of patients respond to a four-dose treatment program", J Clin. Oncol., vol. 16, No. 8 (received by Univ. of Minn. Biomedical Library: Aug. 10, 1998), pp. 2825-2833.

McLaughlin P. et al., "Rituximab in Indolent Lymphoma: The Single-Agent Pivotal Trial", Semin Oncol 26(5, 14 Suppl):79-87, Oct. 1999.

McLaughlin P. et al., "IDEC-C2B8 (Rituximab): Clinical activity in clinically-chemoresistant (CCRD) low-grade or follicular lymphoma (LG/F NHL) and in patients (pts) relapsing after anthracycline therapy (ANTHRA-RX) or ABMT.", Proc Am Soc Clin Oncol 16:16a (#55), May 1997.

McLaughlin P. et al., "Pivotal Phase III clinical trial (PIII CT) of the chimeric anti-CD20 antibody (MAB) IDEC-C2B8 in patients (PTS) with relapsed low-grade or follicular lymphoma (LG/F NHL): A preliminary report.", Ann Oncol 7 (3 Suppl):57 (#194), Jun. 1996.

McLaughlin P. et al., "IDEC-C2B8 anti-CD20 antibody: Final report on a Phase III pivotal trial in patients (PTS) with relapsed low-grade or follicular lymphoma (LG/F NHL).", Blood 88(10):90a (#349), Nov. 1996.

McLaughlin P. et al., "Pharmacokinetics (PK) and Pharmacodynamics (PD) of the anti-CD20 antibody (MAB) IDEC-C2B8 in patients (PTS) with relapsed low-grade or follicular lymphoma (LG/F NHL)" Blood (Abstract #350) 88(10 Suppl 1, Part 1 of 2):90a (Nov. 1996).

McLaughlin P. et al., "Preliminary report on a Phase III pivotal trial of the anti-CD20 antibody (MAB) IDEC-C2B8 in patients (PTS) with relapsed low-grade or follicular lymphoma." Proc Am Soc Clin Oncol 15:417 (#1281), May 1996.

Meeker, T.C. et al., "A clinical trial of anti-idiotype therapy for B cell malignancy", Blood 1985; 65: pp. 1349-1363.

Miller, R.A. et al., "Treatment of B-Cell Lymphoma with monoclonal anti-idiotype antibody.", N Engl J Med 306(9): 517-522, 1982.

RITUXAN (Rituximab) full prescribing information, pp. 1-2 (Nov. 1997).

Rituximab Prescribing Information, Oct. 2012, pp. 1-40.

Rogers, J., et al., "Clearance of bcl-2 (t14;18) from peripheral blood (PB) and bone marrow (BM) in patients (PTS) with relapsed low-grade or follicular (IWF:A-D) lymphoma (NHL) following single-agent therapy with the chimeric anti-CD20 antibody (MAB) IDEC-C2B8.", Ann Oncol 7(3 Suppl):34 (#108), Jun. 1996.

Rogers, J., et al., "Analysis of bcl-2 t(14;18) translocation in relapsed B-cell lymphoma patients treated with the chimeric anti-CD20 antibody IDEC-C2B8.", Proc Annu Meet Am Assoc Cancer Res 37:213 (#1456), Mar. 1996.

Rosenberg, J. et al., "Pharmacokinetic analysis of serum concentrations of the chimeric anti-CD20 antibody IDEC-C2B8 in patients with relapsed B-cell lymphoma." Proc Am Soc Clin Oncol 15:418 (#1282), May 1996.

Rosenberg J., "Pharmacokinetics (PK) of the chimeric anti-CD20 antibody (MAB) IDEC-C2B8: Analysis of serum concentrations in patients (PTS) with relapsed B-cell lymphoma." Br J Haematol 93 (2 Suppl):283 (#1071), May 1996.

(56) References Cited

OTHER PUBLICATIONS

Weisdorf, Daniel et al., "Survival After Relapse of Low-Grade Non-Hodgkin's Lymphoma: Implications for Marrow Transplantation"; *J. Clin Oncol* 1992; 10(6): pp. 942-947.

White, C.A. et al., "Review of single agent IDEC-C2B8 safety and efficacy results in low-grade or follicular non-Hodgkin's lymphoma.", Eur J Cancer 33(5 Suppl):S40 (#91), Jun. 1997.

White, C.A. et al., "Anti-CD20 antibody (MAB) IDEC-C2B8 in relapsed low-grade/follicular (LG/F) B-cell non-Hodgkin's lymphoma (NHL). Expanded efficacy and safety results.", J Immunother 19(6):458, Nov. 1996.

White, C.A. et al., "IDEC-C2B8: Improved tolerance correlated with pharmacodynamic effects in patients with B-cell NHL.", Proc Annu Meet Am Assoc Cancer Res 36:638 (#3799), Mar. 1995.

White, C.A., "Rituximab immunotherapy for non-Hodgkin's lymphoma." Cancer Biother Radiopharm. Aug. 1999;14(4):241-50.

Almasri N.M. et al. *Am. J. Hematol.* 40: 259-63, 1992. Reduced expression of CD20 antigen as a characteristic marker for chronic lymphocytic leukemia.

Armitage J.O. et al. *J. Clin. Oncol.* 16(8): 2780-95, 1998. New approach to classifying non-Hodgkin's lymphomas: clinical features of the major histologic subtypes. Non-Hodgkin's Lymphoma Classification Project.

Arranz R. et al. *J. Clin. Oncol.* 16(4): 1538-46, 1998. Role of interferon alfa-2b in the induction and maintenance treatment of low-grade non-Hodgkin's lymphoma: results from a prospective, multicenter trial with double randomization.

Buchsbaum D.J. et al. *Int'l J. Rad. Oncol. Biol. Phys.* 25(4): 629-38, 1993. Comparison of $^{131}$I- and $^{90}$Y-labeled monoclonal antibody 17-1A for treatment of human colon cancer xenografts.

Caligiuri M.A. et al. *J. Clin. Oncol.* 9(12): 2110-19, 1991. Extended continuous infusion low-dose recombinant interleukin-2 in advanced cancer: prolonged immunomodulation without significant toxicity.

Carrasquillo J.A. et al. *J. Nucl. Med.* 26: 67, abst. No. 276, 1985. Improved imaging of metastatic melanoma with high dose 9.2.27 In-111 monoclonal antibody.

Chen J.J. et al. *J. Immunol.* 143(3): 1053-57, 1989. Tumor idiotype vaccines. VI. Synergistic anti-tumor effects with combined "internal image" anti-idiotypes and chemotherapy.

Chinn P.C. et al. *Int. J. Oncol.* 15(5): 1017-25, Nov. 1999. Preclinical evaluation of 90Y-labeled anti-CD20 monoclonal antibody for treatment of non-Hodgkin's lymphoma.

Clark E.A. et al. *J. Cell. Biochem.* (abstract #0147) (Suppl. 9A): 63, 1985. Anti-Bp35 antibody induces human B cell proliferation: implications for in vivo immunotherapy.

Comella, et al., *Tumori*, 68(2):137-142, (Apr. 30, 1982) Combination chemotherapy (CVP or CHOP)-radiotherapy approach in early stage non-Hodgkin's lymphomas.

Czuczman et al., *J. Mol. Med.* 75(7): B231, abstract #258 (1997); "IDEC-C2B8/CHOP chemoimmunotherapy in patients with low grade lymphoma: Clinical and bcl-2 (PCR) results."

Davis T.A. et al. *J. Clin. Oncol.* 17(6): 1851-57, 1999. Single-agent monoclonal antibody efficacy in bulky non-Hodgkin's lymphoma: results of a phase II trial of rituximab.

DeNardo G.L. et al. *Int. J. Radiat. Oncol. Biot. Phys.* 11(2): 335-48, 1985. Requirements for a treatment planning system for radioimmunotherapy.

Di Gaetano N. et al. *Br. J. Haematol.* 114(4): 800-09, 2001. Synergism between fludarabine and rituximab revealed in a follicular lymphoma cell line resistant to the cytotoxic activity of either drug alone.

Dillman R.O. *J. Clin. Oncol.* 12(7): 1497-1515(Jul. 1994). Antibodies as cytotoxic therapy.

Foran J.M. et al. *Br. J Haematol.* (Abstract #O-0586) 102(1): 149, 1998. Immunotherapy of mantle cell lymphoma (MCL), lymphoplasmacytoid lymphoma (LPC) and Waldentrom's macroglobulinemia (WM), and small lymphocytic lymphoma (SLL) with rituximab (IDEC-C2B8): preliminary results of an ongoing international multicentre trial.

Foran J.M. et al. *J. Clin. Oncol.* 18: 317-24, 2000. European phase II study of rituximab (chimeric anti-CD20 monoclonal antibody) for patients with newly diagnosed mantle-cell lymphoma and previously treated mantle-cell lymphoma, immunocytoma, and small B-cell lymphocytic lymphoma.

Freedman A.S. et al. *J. Clin. Oncol.* 8(5): 784-91, May 1990: Autologous bone marrow transplantation in B-cell non-Hodgkin's lymphoma: very low treatment-related mortality in 100 patients in sensitive relapse.

Ginaldi L. et al. *J. Clin. Pathol.* 51: 364-69, 1998. Levels of expression of CD19 and CD20 in chronic B leukaemias.

Hagenbeek A. et al. *J. Clin. Oncol.* 16(1): 41-47, 1998. Maintenance of remission with human recombinant interferon alfa-2a in patients with stages III and IV low-grade malignant non-Hodgkin's lymphoma. European Organization for Research and Treatment of Cancer Lymphoma Cooperative Group.

Harris N.L. et al. *J. Clin. Oncol.* 17(12): 3835-49, 1999. World Health Organization classification of neoplastic diseases of the hematopoietic and lymphoid tissues: report of the Clinical Advisory Committee meeting—Airlie House, Virginia, Nov. 1997.

Kennedy et al., *Br. J. Haematol.* 119(2): 412-6 (2002) "Incidence and nature of CD20-negative relapses following rituximab therapy in aggressive B-cell non-Hodgkin's lymphoma: a retrospective review."

Klarnet J.P. et al. *J. Immunol.* 138(11): 4012-17, 1987. Antigen-driven T cell clones can proliferate in vivo, eradicate disseminated leukemia, and provide specific immunologic memory.

Knox S.J. et al. *J Immunother.* 16(2): 161, abst. No. 51, 1994. $^{90}$Y-anti-CD20 monoclonal antibody therapy (IDEC-Y2B8) for recurrent B cell lymphoma.

Knox S.J. et al. *Int. J. Rad. Oncol. Biol.Phys.* (Abstract #148) 32(Suppl 1): 215, 1995. $^{90}$Y-anti-CD20 monoclonal antibody therapy for recurrent B cell lymphoma.

Link M.P. et al. *J. Immunol.* 137(9): 3013-18, 1986. A unique antigen on mature B-cells defined by a monoclonal antibody.

"Lymphomas: New Recognitions and Therapy Strategies", Wolfgang Hiddemann, Martin Dreyling, Harald Stein editors, Georg Thieme Verlag, Stuttgart, New York, pp. 78-81 (2005), English translation and original in German.

Maloney D.G. et al. *J. Clin. Oncol.* 15(10): 3266-74, Oct. 1997. IDEC-C2B8: results of a phase 1 multiple-dose trial in patients with relapsed non-Hodgkin's Lymphoma.

McLaughlin P. et al. *J. Clin. Oncol.* 16(8): 2825-33, Aug. 1998. Rituximab chimeric-anti-CD20 monoclonal antibody therapy for relapsed indolent lymphoma: half of patients respond to a four-dose treatment program.

Meredith R.F. et al. *J. Nucl. Med.* 33(9): 1648-53, 1992. Dose fractionation of radiolabeled antibodies in patients with metastatic colon cancer.

Muzaffar S. et al. *J. Pak. Med. Assoc.* 47(4): 106-09, Apr. 1997. Immunophenotypic analysis of non-Hodgkin's lymphoma.

Nguyen D.T. et al. *Eur. J. Haeinatol.* 62: 76-82, 1999. IDEC-C2B8 anti-CD20 (Rituximab) immunotherapy in patients with low-grade non-Hodgkin's lymphoma and lymphoproliferative disorders: evaluation of response on 48 patients.

Press O.W. et al. *N. Engl. J.Med.* 329(17): 1219-24, 1993. Radiolabeled-antibody therapy of B-cell lymphoma with autologous bone marrow support.

Reff M. et al. *J. Cell. Biochem.* Suppl. 17E: 260, abst. No. T103, 1993. Depletion of B cells in vivo by a chimeric mouse human monoclonal antibody to CD20.

Shipp et al. *N. Engl. J. Med.* 329(14): 987-94, 1993. A predictive model for aggressive non-Hodgkin's lymphoma: The International Non-Hodgkin's Lymphoma Prognostic Factors Project.

Smalley R.V. et al. *N. Engl. J. Med.* 327(19): 1336-41, 1992. Interferon alfa combined with cytotoxic chemotherapy for patients with non-Hodgkin's lymphoma.

Smeland E.B. et al. *J. Immunol.* 138(10): 3179-84, 1987. Activation of human B cells: alternate options for initial triggering and effects of nonmitogenic concentrations of anti-IgM antibodies on resting and activated cells.

Solal-Celigny P. et al. *J. Clin. Oncol.* 16(7): 2332-38, 1998. Doxorubicin-containing regimen with or without interferon alfa-2b

(56) References Cited

OTHER PUBLICATIONS for advanced follicular lymphomas: final analysis of survival and toxicity in the Groupe d'Etude des Lymphomes Folliculaires 86 Trial.
Stashenko P. et al. *J. Immunol.* 125(4): 1678-85, 1980. Characterization of Human B Lymphocyte-Specific Antigen.
Uckun F.M. et al. *J. Immunol.* 134(5): 3504-15, 1985. Combined ex vivo treatment with immunotoxins and mafosfamid: a novel immunochemotherapeutic approach for elimination of neoplastic T cells from autologous marrow grafts.
Valentine M.A. et al. *J. Biol. Chem.* 264: 11282-87, 1989. Phosphorylation of the CD20 phosphoprotein in resting B lymphocytes. Regulation by protein kinase C.
van der Kolk L.E. et al. *Br. J. Haematol.* 102(1): 243, abst. No. P-0970, Jul. 1998. Chimeric anti-CD20 monoclonal antibody (rituximab) plus G-CSF in relapsed B-cell lymphoma: a phase I/II clinical trial.
Wiseman G. et al. *Int. J. Rad. Oncol. Biol. Phys.* 42(10 Suppl): 390, abst. No. 260, 1998. Radioimmunotherapy of relapsed or refractory non-Hodgkin's Lymphoma (NHL) with IDEC-Y2B8.
Wiseman G.A. et al. *J. Nucl. Med.* 39(5 Suppl.): 69P, abst. No. 267, 1998. Non-Hodgkin's lymphoma tumor and bone marrow radiation doses from radioimmunotherapy with IDEC-Y2B8 yttrium-90 anti-CD20 monoclonal antibody.
Wiseman G.A. et al. *J. Nucl. Med.* 40(1 Suppl.): 64P, abst. No. 260, 1999. Final dosimetry results of IDEC-Y2B8 phase I/II $^{90}$yttrium radioimmunotherapy trial in non-Hodgkin's lymphoma (NHL).
Witzig T.E. et al. *J. Clin. Oncol.* 17(12): 3793-3803, 1999. Phase I/II trial of IDEC-Y2B8 radioimmunotherapy for treatment of relapsed or refractory CD20($^+$) B-cell non-Hodgkin's lymphoma.
Carlson, R. "Rituximab plus CHOP: a new approach for non-Hodgkin's lymphoma?" Inpharma No. 1116:7-8 (Dec. 6, 1997) (Chemotherapy Foundation Symposium XV, New York, US, Nov. 1997).
Clinical Review of BLA Reference No. BLA 97-0260 and BLA 97-0244, pp. 1-40 with cover page signed: Nov. 1997; the source is available on the Internet (as of Nov. 28, 2013) at the following (URL): http://www.fda.gov/downloads/Drugs/DeveloumentApprovalProcess/HowDrugsareDevelopedandApproved/ApprovalApplications/TherapeuticBiologicApplications/ucm113330.pdf.
Fisher et al. "Comparison of a standard regimen (CHOP) with three instensive chemotherapy regimens for advanced non-Hodgkin's lymphoma", The New England Journal of Medicine 328(14):1002-1006 (Apr. 8, 1993).
Gottlieb et al. "Chemotherapy of malignant lymphoma with adriamycin", Cancer Research 33:3024-3028 (Nov. 1973).
ECOG E1496 Trial Results "Non-Progressing Low-grade NHL after CVP-RITUXAN®) (Rituximab)", Internet Archive, Wayback Machine, Originally Posted Sep. 25, 2008, pp. I-5. (Retrieved Oct. 14, 2014) https://web.archive.org/web/20080925225303/http://www.rituxan.com/lymphoma/hcp/indications/E1496/index.m.
Al-Ismail, "Combination chemotherapy Including Epirubicin for the Management of Non-Hodgkin's Lymphoma", European J. Cancer and Clinical Oncology, 1987, vol. 23, pp. 1379-1384.
Aviles et al., "Interferon Alpha 2b as Maintenance Therapy in Low Grade Malignant Lymphoma Improves Duration of Remission and Survival", Leukemia and Lymphoma, 1996, vol. 20, pp. 495-499.
Aviles et al., "Maintenance therapy with interferon alfa 2b in patients with diffuse large cell lymphoma", Investigational New Drugs, 1992, vol. 10, pp. 351-355.
Aviles, A., "The role of Interferon as Maintenance Therapy in Malignant Lymphoma", Medical Oncology, 1997, vol. 14, pp. 153-157.
Clendeninn, N.J., et. al., "Phase I/II trials of CAMPATH-1H, a humanized anti-lymphocyte monoclonal antibody (MoAb), in non-Hodgkin's lymphoma (NHL) and chronic lymphocytic leukemia (CLL).", Blood, Nov. 1992, vol. 80, No. 10, Supplement 1, Abstract #624, p. 158a.
ClinicalTrials.gov report on the NCT00003204 (ECOG 1496) Clinical Trial (Jan. 27, 2014) http://clinicaltrials.gov/show/NCT00003204 pp. 1-5 (retrieved Dec. 2, 2014).

ECOG E1496, ACTIVATION OF PROTOCOL E1496, Randomized Phase III Study in Low Grade Lymphoma Comparing Cyclphosphamide/Fludarabine to Standard Therapy Followed by Maintenance Anti-CD20 Antibody, Activation Date: Mar. 19, 1998 pp. 1-47.
ECOG E4494, ACTIVATION OF PROTOCOL E4494, A Phase III Trial of CHOP versus CHOP and Chimeric Anti-CD20 Monoclonal Antibody (IDEC-C2B8) in Older Patients with Diffuse Mixed, Diffuse Large Cell and Immunoblastic Large Cell Histology Non-Hodgkin's Lymphoma, Activation Date: Dec. 12, 1997 pp. 1-61.
ECOG Institutions by Name, http://web.archive.org/web/19980519084032/http://ecog.dfci.harvard.edu/~ecogdb a/general/insts_byname.html (archived May 19, 1998) pp. 1-10 (retrieved Dec. 4, 2014).
FDA Clinical Review of Rituximab dated Sep. 29, 2006, pp. 1-110.
Ghielmini et al., "Prolonged treatment with rituximab in patients with follicular lymphoma significantly increases event-free survival and response duration compared with the standard weekly X4 schedule", Blood, 2004, vol. 103, No. 12, pp. 4416-4423.
Grillo-López, AJ "The First Antibody Therapy for Cancer: a Personal Experience", Expert Review of Anticancer Therapy Retrospective, 2013, vol. 13, No. 4, pp. 399-406.
Gupta and Lister, "Current Management of Follicular Lymphoma", Current Opinion in Oncology, 1996, vol. 8, pp. 360-365.
Hainsworth et al. "Rituximab as First-Line and Maintenance Therapy for Patients With Indolent Non-Hodgkin's Lymphoma", J. Clinical Oncology, 2002, vol. 20, pp. 4261-4267.
Hickish et al., "Molecular monitoring of low grade non-Hodgkin's lymphoma by gene amplification", Br. J. Cancer, 1991, vol. 64, pp. 1161-1163.
Hiddemann et al., "New Aspects in the Treatment of Advanced Low-Grade Non-Hodgkin's Lymphomas: Prednimustine/Mitoxantrone Versus Cyclophosphamide/Vincristine/Prednisone Followed by Interferon Alfa Versus Observation Only—A Preliminary Update of the German Low-Grade Lymphoma Study Group", Seminars in Hematology, 1994, vol. 31, No. 2, Suppl 3, pp. 32-35.
Hoerni et al., "Maintenance Immunotherapy with BCG in Non-Hodgkin's Malignant Lymphomas: a Progress Report of a Randomized Trial", Recent Results in Cancer Research, 1980, vol. 80, pp. 92-97.
Hoerni et al., "Successful Maintenance Immunotherapy by BCG of Non-Hodgkin's Malignant Lymphomas: Results of a Controlled Trial", British J. Haematology, 1979, vol. 42, pp. 507-514.
IDEC and Genentech joint press release, "IDEC Pharmaceuticals and Genentech Announce Positive Final Results", Dec. 9, 1996, pp. 1-5.
Jones et al., "Improved Complete Remission Rates and Survival for Patients with Large Cell Lymphoma Treated with Chemoimmunotherapy", Cancer, 1983, vol. 51, pp. 1083-1090.
Kohler and Milstein, "Derivation of Specific Antibody-Producing Tissue culture and Tumor Lines by Cell Fusion", European J. Immunology, 1976, vol. 6, pp. 511-519.
Maloney et al., "IDEC-C2B8: Results of a Phase I Multiple-Dose Trial in Patients With Relapsed Non-Hodgkin's Lymphoma", J. Clinical Oncology, 1997, vol. 15, pp. 3266-3274.
McLaughlin et al., "Management of Patients with Nodular Lymphoma", UT M.D. Anderson Clinical Conference on Cancer, 1984, vol. 27, pp. 301-312.
McNeil, C. "Non-Hodgkin's Lymphoma Trials in Elderly Look Beyond CHOP", Journal of the National Cancer Institute, Feb. 18, 1998, vol. 90, No. 4, pp. 266-267.
PDQ—Nci's Comprehensive Cancer Database, http://web.archive.org/web/19980116194104/http://cancernet.nci.nih.gov/pdq.htm (archived Jan. 16, 1998) pp. 1-2 (retrieved Dec. 4, 2014).
Ravaud et al., "Adjuvant Bacillus Calmette-Guerin Therapy in Non-Hodgkin's Malignant Lymphomas: Long-Term Results of a Randomized Trial in a Single Institution", J. Clinical Oncology, 1990, vol. 8, pp. 608-614.
Unterhalt et al., "Significant Prolongation of Disease Free Survival in Advanced Low Grade Non Hodgkin's Lymphomas (NHL) by Interferon Alpha Maintenance: International Conference on Malignant Lymphoma, Jun. 5-8, 1996, Lugano, Switzerland", Annals of Oncology, 1996, vol. 7, Supplement 3, p. 229.

(56) References Cited

OTHER PUBLICATIONS

Van Oers et al., "Rituximab maintenance improves clinical outcome of relapsed/resistant follicular non-Hodgkin lymphoma in patients both with and without rituximab during induction: results of a prospective randomized phase 3 intergroup trial", Blood, 2006, vol. 108, pp. 3295-3301.
Almasri N.M. et al., "Reduced expression of CD20 antigen as a characteristic marker for chronic lymphocytic leukemia", Am. J Hematol., 1992, vol. 40, pp. 259-263.
Buchsbaum D.J. et al., "Comparison of131I-and Y-labeled monoclonal antibody 17-1A for treatment of human colon cancer xenografts", Int. J. Rad. Oncol. Biol. Phys., 1993, vol. 25, No. 4, pp. 629-638.
Caligiuri M.A. et al., "Extended continuous infusion low-dose recombinant interleukin-2 in advanced cancer: prolonged immunomodulation without significant toxicity", J. Clin. Oncol., Dec. 1991, vol. 9, No. 12, pp. 2110-2119.
Carrasquillo J.A. et al., "Improved imaging of metastatic melanoma with high dose 9.2.27 In-111 monoclonal antibody" J. Nucl. Med., 1985, vol. 26, No. 67, Abst. No. 276 (1 page).
Chen J.J. et al., "Tumor idiotype vaccines. VI. Synergistic anti-tumor effects with combined internal image anti-idiotypes and chemotherapy.", J Immunol., Aug. 1989, vol. 143, No. 3, pp. 1053-1057.
Chinn P.C. et al., "Preclinical evaluation of 90Y-labeled anti-CD20 monoclonal antibody for treatment of non-Hodgkin's lymphoma.", Int J Oncol., Nov. 1999, vol. 15, No. 5, pp. 1017-1025.
Clark E.A. et al. "Anti-Bp35 antibody induces human B cell proliferation: implications for in vivo immunotherapy.", J Cell. Biochem., 1985, Suppl. 9A, p. 63.
Comella, et al., "Combination chemotherapy (CVP or CHOP)-radiotherapy approach in early stage non-Hodgkins' lymphomas", Tumori, Apr. 1982, vol. 68, No. 2, pp. 137-142.
Czuczman et al., "IDEC-C2B8/CHOP chemoimmunotherapy in patients with low grade lymphoma: Clinical and bcl-2 (PCR) results," J Mol. Med.. 1997, vol. 75, No. 7, abstract #258, p. B231.
Di Gaetano N. et al., "Synergism between fludarabine and rituximab revealed in a follicular lymphoma cell line resistant to the cytotoxic activity of either drug alone", Br. J Haematol, 2001, vol. 114, No. 4, pp. 800-809.
Dittman R.O, "Antibodies as cytotoxic therapy.", J. Clin. Oncol., Jul. 1994, vol. 12, No. 7, pp. 1497-1515.
Foran J.M. et al., "European phase II study of rituximab (chimeric anti-CD20 monoclonal antibody) for patients with newly diagnosed mantle-cell lymphoma and previously treated mantle-cell lymphoma, immunocytoma, and small B-cell lymphocytic lymphoma", J Clin Oncol., Jan. 2000, vol. 18, No. 2, pp. 317-324.
Freedman A.S. et al., "Autologous bone marrow transplantation in B-cell non-Hodgkin's lymphoma: very low treatment-related mortality in 100 patients in sensitive relapse", J. Clin Oncol., May 1990, vol. 8, No. 5, pp. 784-791.
Maloney D.G. et al., "IDEC-C2B8: results of a phase 1 multiple-dose trial in patients with relapsed non-Hodgkin's Lymphoma", J Clin Oncol., Oct. 1997, vol. 15, No. 10, pp. 3266-3274.
Muzaffar S. et al., "Immunophenotypic analysis of non-Hodgkin's lymphoma", J Pak Med Assoc., Apr. 1997, vol. 47, No. 4, pp. 106-109.
Nguyen D.T. et al., "IDEC-C2B8 anti-CD20 (rituximab) immunotherapy in patients with low-grade non-Hodgkin's lymphoma and lymphoproliferative disorders: evaluation of response on 48 patients", Eur J Haematol., Feb. 1999, vol. 62, No. 2, pp. 76-82.
Press O.W. et al., "Radiolabeled-antibody therapy of B-cell lymphoma with autologous bone marrow support", N Engl J Med., Oct. 1993, vol. 329, No. 17, pp. 1219-1224.
Reff M. et al., "Depletion of B cells in vivo by a chimeric mouse human monoclonal antibody to CD20.", J. Cell. Biochem., 1993, Suppl. 17E: p. 260, abst. No. T103.
Saville, M.W., Statement of M. Wayne Saville, M.D., dated Dec. 20, 2007, submitted by applicant in Taiwan (R.O.C.) patent application No. 088119557 (Treatment of hematologic malignancies associated with circulating tumor cells using chimeric anti-CD20 antibody, Grillo-Lopez et al., filed Nov. 9, 1999) pp. 1-3.
Shipp et al. "The International Non-Hodgkin's Lymphoma Prognostic Factors Project: A predictive model for aggressive non-Hodgkin's lymphoma", N Engl J Med., Sep. 1993, vol. 329, No. 14, pp. 987-994.
Smalley R.V. et al., "Interferon alfa combined with cytotoxic chemotherapy for patients with non-Hodgkin's lymphoma", N Engl J Med., Nov. 1992, vol. 327, No. 19, pp. 1336-1341.
Smeland E.B. et al., "Activation of human B cells: alternate options for initial triggering and effects of nonmitogenic concentrations of anti-IgM antibodies on resting and activated cells", J Immunol., May 1987, vol. 138, No. 10, pp. 3179-3184.
Solal-Celigny P. et al., "Doxorubicin-containing regimen with or without interferon alfa-2b for advanced follicular lymphomas: final analysis of survival and toxicity in the Groupe d'Etude des Lymphomes Folliculaires 86 Trial", J Clin Oncol., Jul. 1998, vol. 16, No. 7, pp. 2332-2338.
Stashenko P. et al., "Characterization of Human B Lymphocyte-Specific Antigen", J Immunol., Oct. 1980, vol. 125, No. 4 pp. 1678-1685.
Valentine M.A. et al., "Phosphorylation of the CD20 phosphoprotein in resting B lymphocytes. Regulation by protein kinase C", J Biol Chem., Jul. 1989, vol. 264, No. 19, pp. 11282-11287.
Van Der Kolk et al., "Chimeric Anti-CD20 Monoclonal Antibody (Rituximab) Plus G-CSF in Relapsed B-Cell Lymphoma: A Phase I/II Clinical Trial", British Journal of Haematology, Jul. 1998, vol. 102, No. 1, p. 243.
Wiseman G. et al., "Radioimmunotherapy of relapsed or refractory non-Hodgkin's Lymphoma (NHL) with IDEC-Y2B8.", I.J Rad. Oncol. Biol. Phys., 1999, vol. 45, Suppl., 10, p. 390, abst. No. 260.
Wiseman G.A. et al., "Non-Hodgkin's lymphoma tumor and bone marrow radiation doses from radioimmunotherapy with IDEC-Y2B8 yttrium-90 anti-CD20 monoclonal antibody.", J Nucl Med. 1998, vol. 39, Suppl. 5, p. 69P, abst. No. 267.
Wiseman G.A. et al.. "Final dosimetry results of IDEC-Y2B8 phase I/II 90yttrium radioimmunotherapy trial in non-Hodgkin's lymphoma (NHL).", J Nucl Med., 1999, vol. 40, Suppl. 1, p. 64P, abst. No. 260.
Zhou X. et al., "Application of cytokine therapy in tumor treatment", Chinese Pharm. J., 1995, vol. 30, No. 8, pp. 453-54 (English translation of abstract provided).
"Biological Therapy for Cancer Treatment", Stanford Cancer Center, https://web.archive.org/web/20131617382400/http://cancer.stanford.edu/information/cancerTreatment/methods/biological.html, 2009 (archived Jun. 17, 2013), pp. 1-8 (Retrieved Dec. 22, 2014).
"NCI—Cooperative Group—Industry Relationship Guidelines", updated May 29, 2008 http://ctep.cancer.gov/industrycollaborations2/guidelines.htm retrieved Aug. 25, 2015, pp. 1-3.
2011 RITUXAN (Rituximab) full prescribing information, pp. 1-8 (Initial US Approval Nov. 1997, Revised Jan. 2011).
Aisenberg AC, "Coherent view of non-Hodgkin's lymphoma." J Clin Oncol., 1995, vol. 13, pp. 2656-2675.
Amendment and Reply under 35 CFR §1.111 filed Aug. 25, 2010, in U.S. Appl. No. 11/840,956 (Antonio J. Grillo-Lopez, Combination Therapies For B-Cell Lymphomas Comprising Administration of Anti-CD20 Antibody, filed Aug. 18, 2007), pp. 1-16.
Amendment and Response to Restriction Requirement filed Jan. 29, 2010 in U.S. Appl. No. 11/840,956 (Antonio J. Grillo-Lopez, Combination Therapies for B-Cell Lymphomas Comprising Administration of Anti-CD20 Antibody, filed Aug. 18, 2007), pp. 1-9.
Amendment Responsive to Examiner's Request filed Oct. 28, 2011 in U.S. Appl. No. 11/840,956 (Antonio J. Grillo-Lopez, Combination Therapies for B-Cell Lymphomas Comprising Administration of Anti-CD20 Antibody, filed Aug. 18, 2007), pp. 1-8.
Applicant's Remarks/ Arguments filed Jun. 6, 2011 in U.S. Appl. No. 11/840,956 (Antonio J. Grillo-Lopez, Combination Therapies for B-Cell Lymphomas Comprising Administration of Anti-CD20 Antibody, filed Aug. 18, 2007) pp. 19-35.
Applicant's Remarks/Arguments filed May 22, 2012 with USPTO in U.S. Appl. No. 11/840,956 (Antonio J. Grillo-Lopez, Combination Therapies for B-Cell Lymphomas Comprising Administration of Anti-CD20 Antibody, filed Aug. 18, 2007), pp. 1-8.

(56) References Cited

OTHER PUBLICATIONS

Biogen's Patent Owner Preliminary Response filed Apr. 15, 2015 in Response to Petition Inter Partes Review of U.S. Pat. No. 8,329,172 dated Dec. 15, 2014 (U.S. Appl. No. 11/840,956, Antonio J. Grillo-Lopez, Combination Therapies for B-Cell Lymphomas Comprising Administration of Anti-CD20 Antibody, filed Aug. 18, 2007) pp. 1-69.
Biological Therapies: Using the Immune System to Treat Cancer, National Cancer Institute, http://web.archive.org/web/19980216091909/http://cancernet.nci.nih.gov/clinpdq/therapy/Biological_Therapies:_Using_the_immune_System_To_Treat_Cancer.html (last modified Sep. 1995, archived Feb. 16, 1998) pp. 1-5 (retrieved Apr. 8, 2014).
Blackwelder, William C., "'Proving the Null Hypothesis' in Clinical Trials", Controlled Clinical Trials, 1982, vol. 3, pp. 345-353.
Cabanillas et. al., "Clinical, Biologic, and Histologic Features of Late Relapses in Diffuse Large Cell Lymphoma", Blood, Feb. 1992, vol. 79, No. 4, pp. 1024-1028.
Chisesi et. al., "Randomized Study of Chlorambucil (CB) Compared to Interferon (Alfa-2b) Combined with CB in Low-Grade Non-Hodgkin's Lymphoma: An interim report of a randomized study", Eur. J. Cancer, 1991, vol. 27, Supp. 4, pp. S31-S33.
Czuczman M.S. et al., "IDEC-C2B8/CHOP Chemoimmunotherapy in Patients with Low-Grade Lymphoma: Clinical BCL-2 (PCR) Final Results", Nov. 1996, Blood 88, vol. 10, abstract 1799, pp. 453a, Nov. 1996.
Dallaire, B.K. et al., "IDEC-C2B8 (RITUXIMAB): Biology and preclinical studies", J Mol Med, Jul. 1997, vol. 75, No. 7, abstract #256, pp. B230-B231.
Dana et. al., "A Randomized Study of Alpha-Interferon Consolidation in Patients with Low-Grade Lymphoma Who Have Responded to Pro-Mace-Mopp (Day 1-8) (SWOG 8809)", Proceedings of ASCO, May 16-19, 1998, vol. 17, Abstract 10, p. 3a.
Decision Denying Institution of Inter Partes Review of U.S. Pat. No. 8,329,172 dated Jul. 13, 2015 (U.S. Appl. No. 11/840,956, Antonio J. Grillo-Lopez, Combination Therapies for B-Cell Lymphomas Comprising Administration of Anti-CD20 Antibody, filed Aug. 18, 2007), pp. 1-35.
Declaration of Michael J. Grossbard, M.D., in Support of the Petition for Inter Partes Review of U.S. Pat. No. 8,329,172 (U.S. Appl. No. 11/840,956, Antonio J. Grillo-Lopez, Combination Therapies for B-Cell Lymphomas Comprising Administration of Anti-CD20 Antibody, filed Aug. 18, 2007), dated Dec. 5, 2014 pp. 1-107.
Dillman RO et al., "Therapy of chronic lymphocytic leukemia and cutaneous T-cell lymphoma with T101 monoclonal antibody." J Clin Oncol,, 1984, vol. 2, pp. 881-891.
Documents from European Oppositions pertaining to EP Application No. 08005921.5 (Antonio J. Grillo-Lopez, Combination Therapies for B-Cell Lymphomas Comprising Administration of Anti-CD20 Antibody, filed Aug. 11, 1999) (Patent No. EP 1974747), pp. 1-52.
ECOG E1496 Trial Results "Non-Progressing Low-grade NHL after CVP—RITUXAN® (Rituximab)", Study date Mar. 9, 2009, pp. 1-7, (Retrieved Dec. 2, 2010) http://www.rituxan.com/lymphoma/hcp/indications/E1496/index.m.
Foon et. al., "Lymphomas", Williams Hematology, 5th edition, Ch. 111, Part ix, Beutler, Lichtman, Coller, & Kipps, McGraw-Hill, Inc., 1995, pp. 1076-1096.
Foon KA et al., "Effects of monoclonal antibody therapy in patients with chronic lymphocytic leukemia." Blood, 1984, vol. 64, pp. 1085-1093.
Gallagher CJ et al., "Follicular lymphoma: Prognostic factors for response and survival.", 1986, J Clin Oncol, vol. 4, pp. 1470-1480.
Gisselbrecht et. al., "Treatment of low-grade non-Hodgkin's lymphomas", Non-Hodgkin's Lymphoma, Solal-Céligny, Brousse, Reyes, Gisselbrecht & Coiffier, Manson Publishing Ltd., 1993, pp. 317-336.
Gribben JG et al., "Detection of residual lymphoma cells by polymerase chain reaction in peripheral blood is significantly less predictive for relapse than detection in bone marrow." Blood, 1994, vol. 83, pp. 3800-3807.

Grillo-López, A.J. et al., "Development of Response Criteria (RC) for Low-Grade or Follicular Lymphomas (LG/F NHL) and Application in a 166 Patient Study", 26th Annual Meeting of the International Society for Experimental Hematology, Exp Hematol, Aug. 1997, vol. 25, No. 8, Abstract 17, p. 732.
Hiddemann, et al. "Lymphomas: New Recognitions and Therapy Strategies", Ch. 11, C.H. Beck, Thieme Georg Verlag, 2005, pp. 78-81 (Translated).
Information Disclosure Statement Form PTO-1449 considered by examiner on May 10, 2010 in U.S. Appl. No. 11/840,956 (Antonio J. Grillo-Lopez, Combination Therapies for B-Cell Lymphomas Comprising Administration of Anti-CD20 Antibody, filed Aug. 18, 2007), pp. 1-31.
Kaplan EL et al., "Nonparametric estimation from incomplete observations." J Am Stat Assoc, 1958, vol. 53, pp. 457-481.
Kimura et al., "VII Medicaments for hematologic diseases 'lymphoid malignancy'; 177. Drug therapies for non-Hodgkin's lymphoma" Medicina vol. 24, No. 10 (1987), pp. 2194-2197 (English translation of Japanese Office Action dated Dec. 25, 2012, filed in corresponding JP Patent Application No. 2000-564662, Antonio J. Grillo-Lopez, Combination Therapies for B-Cell Lymphomas Comprising Administration of Anti-CD20 Antibody).
Kwak et. al., "Biological response modifiers", The Non-Hodgkin's Lymphomas, 2nd edition, Ch. 32, Ian T. MaGrath, Arnold, 1997, pp. 699-714.
Leonard et. al., "Monoclonal Antibody Therapy of Lymphoma", American Cancer Society Atlas of Clinical Oncology Malignant Lymphomas, Ch. 18, Michael L. Grossbard, BC Decker Inc. 2002, pp. 301-315.
LoBuglio AF et al., "Mouse/human chimeric monoclonal antibody in man: Kinetics and Immune response." PNAS, 1989, vol. 86, pp. 4220-4224.
Lopez-Guillermo A et al., "The molecular breakpoint site of bcl-2 gene has prognostic importance in indolent follicular lymphoma.", Blood, Nov. 1996, vol. 88, No. 10, SUPPL 1 Part 1 of 2, Abstract 1162, p. 293a.
Lopez-Guillermo et al. "The clinical significance of molecular response in indolent follicular lymphomas", Blood, Apr. 1998, vol. 91, No. 8, pp. 2955-2960.
McLaughlin P et al., "Fludarabine phosphate in lymphoma: an important new therapeutic agent" in Advances in Lymphoma Research, Boston, MA, Cabanillas F, Rodriguez, MA, Kluwer Academic Publishers, 1996, pp. 3-14.
McLaughlin P. et al., "IDEC-C2B8 (Rituximab): Clinical activity in clinically-chemoresistant (CCRD) low-grade or follicular lymphoma (LG/F NHL) and in patients (pts) relapsing after anthracycline therapy (ANTHRA-RX) or ABMT.", Proc Am Soc Clin Oncol, May 1997, vol. 16, Abstract #55, p. 16a.
Mueller BM et al., "Enhancement of antibody-dependent cytotoxicity with a chimeric anti-GD2 antibody." J Immunol, 1990, vol. 144, pp. 1382-1386.
National Cancer Institute: Surveillance, Epidemology, and End Results Program, "SEER Stat Fact Sheets: Non-Hodgkin Lymphoma", http://seer.cancer.gov/statfacts/html/nhl.html, Apr. 2014, pp. 1-9 (retrieved Dec. 2, 2014).
Notice of Allowability dated Jun. 26, 2012 in U.S. Appl. No. 11/840,956 (Antonio J. Grillo-Lopez, Combination Therapies for B-Cell Lymphomas Comprising Administration of Anti-CD20 Antibody, filed Aug. 18, 2007), pp. 1-2.
Office Action mailed by the USPTO dated Feb. 29, 2012 in U.S. Appl. No. 11/840,956 (Antonio J. Grillo-Lopez, Combination Therapies for B-Cell Lymphomas Comprising Administration of Anti-CD20 Antibody, filed Aug. 18, 2007), pp. 1-12.
Office Restriction Requirement mailed Oct. 15, 2009 in U.S. Appl. No. 11/840,956 (Antonio J. Grillo-Lopez, Combination Therapies for B-Cell Lymphomas Comprising Administration of Anti-CD20 Antibody, filed Aug. 18, 2007) pp. 1-5.
Official Action mailed by the USPTO dated May 11, 2010 in U.S. Appl. No. 11/840,956 (Antonio J. Grillo-Lopez, Combination Therapies for B-Cell Lymphomas Comprising Administration of Anti-CD20 Antibody, filed Aug. 18, 2007), pp. 1-8.
Patent Owner's Updated Mandatory Notices in Petition for Inter Partes Review of U.S. Pat. No. 8,329,172 dated May 11, 2015 (U.S.

(56) References Cited

OTHER PUBLICATIONS

Appl. No. 11/840,956, Antonio J. Grillo-Lopez, Combination Therapies for B-Cell Lymphomas Comprising Administration of Anti-CD20 Antibody, filed Aug. 18, 2007) pp. 1-4.
Peterson et. al., "Cyclophosphamide versus cyclophosphamide plus interferon alfa-2b in follicular low-grade lymphomas: an intergroup phase III trial (CALGB 8691 and EST 7486)", Proceedings of ASCO, May 17-20, 1997, vol. 16, Abstract 48, p. 14a.
Petition for Inter Partes Review of U.S. Pat. No. 8,329,172 (U.S. Appl. No. 11/840,956, Antonio J. Grillo-Lopez, Combination Therapies for B-Cell Lymphomas Comprising Administration of Anti-CD20 Antibody, filed Aug. 18, 2007) dated Dec. 15, 2014 pp. 1-76.
Petitioner's Request for Rehearing on the Institution Decision in Inter Partes Review of U.S. Pat. No. 8,329,172 dated Dec. 15, 2014 (U.S. Appl. No. 11/840,956, Antonio Grillo-Lopez, Combination Therapies for B-Cell Lymphomas Comprising Administration of Anti-CD20 Antibody, filed Aug. 18, 2007) pp. 1-18.
Petryk et.al., "Indolent B-Cell Lymphomas", American Cancer Society Atlas of Clinical Oncology Malignant Lymphomas, Ch. 6, Michael L. Grossbard, BC Decker Inc. 2002, pp. 94-111.
Piro LD, "Cladribine in the treatment of low-grade non-Hodgkin's lymphoma." Semin Hematol, 1996, vol. 33, No. 1, SUPPL 1, pp. 34-39.
Pott-Hoeck C. et al., "Purine analogs in the treatment of low-grade lymphomas and chronic lymphocytic leukemias." Ann Oncol, 1995, vol. 6, pp. 421-433.
Poynton CH et al., "Adverse reactions to Campath-1H monoclonal antibody." Lancet, 1993, vol. 341, p. 1037.
Preliminary Amendment filed Oct. 31, 2007 in U.S. Appl. No. 11/840,956 (Antonio J. Grillo-Lopez, Combination Therapies for B-Cell Lymphomas Comprising Administration of Anti-CD20 Antibody, filed Aug. 18, 2007), pp. 1-5.
Rituxan® (Rituximab) Draft Labeling Text, U.S. BL 103705/5230 Amendment: RITUXAN®(Rituximab)—Genentech, Inc. Sep. 29, 2006, pp. 1-46.
Rituxan® (Rituximab) Labeling Text, U.S. BL 103705 Supplemental Amendment: Rituxan Rheumatoid Arthritis—Genentech, Inc. Feb. 2006, pp. 1-53.
Ritz J et al., "Serotherapy of acute lymphoblastic leukemia with monoclonal antibody." Blood, 1981, vol. 58, pp. 141-152.
Rohatiner et. al., "Follicular Lymphoma", The Non-Hodgkin's Lymphomas, $2^{nd}$ edition, Ch. 41, Ian T. MaGrath, Arnold, 1997, pp. 867-895.
Rohatiner et. al., "Meta-Analysis to Evaluate the Role of Interferon in Follicular Lymphoma," J. Clinical Oncology, Apr. 2005, vol. 23, No. 10, pp. 2215-2223.
Schein et. al., "Non-Hodgkin's Lymphoma: Patterns of Relapse from Complete Remission After Combination Chemotherapy", Cancer, 1975, vol. 35, pp. 354-357.
Tedder TF et al., "CD20: A regulator of cell-cycle progression of B lymphocytes." Immunol Today, 1994, vol. 15, pp. 450-454.
Uckun F.M. et al., "Combined ex vivo treatment with immunotoxins and mafosfamid: a novel immunochemotherapeutic approach for elimination of neoplastic T cells from autologous marrow grafts", J Immunol., May 1985, vol. 134, No. 5, pp. 3504-3515.
United States Department of Health and Human Services, Food and Drug Administration, "Guidance for Industry: Distributing Scientific and Medical Publications on Unapproved New Uses—Recommended Practices", Revised Draft Guidance, Feb. 2014, pp. 1-17.
Unterhalt, et. al., "Long Term Interferon Alpha Maintenance Prolongs Remission Duration in Advanced Low Grade Lymphomas and is Related to the Efficacy of Initial Cytoreductive Chemotherapy", Blood, Nov. 1996, vol. 88, No. 10, Suppl. 1, Abstract 1801, pp. 453a.
White, C.A. et al., "Review of single agent IDEC-C2B8 safety and efficacy results in low-grade or follicular non-Hodgkin's lymphoma.", Eur J Cancer, Jun. 1997, vol. 33, Suppl. 5, Abstract #91, p. S40.
White, et. al., "Anti-Cd20 Monoclonal Antibodies As Novel Treatments for Non-Hodgkin's Lymphoma", Pharm. Sci. Tech. Today, Mar. 1999, vol. 2, No. 3, pp. 95-101.
Zhou L-J et al., "CD20 Workshop Panel Report" in Schlossman SF. Boumsell L., Gilks W., et al. (eds): *Leucocyte Typing V* (White Cell Differentiation Antigens. Proceedings of the Fifth International Workshop and Conference Held in Boston, USA Nov. 3-7, 1993) Oxford, United Kingdom, Oxford University, 1995, vol. 1, pp. 511-514.

\* cited by examiner

SEQUENCE LISTING

<160> NUMBER OF SEQ ID NOS: 2

<210> SEQ ID NO 1
<211> LENGTH: 106
<212> TYPE: PRT
<213> ORGANISM: Mus musculus

<400> SEQUENCE: 1

Gln Ile Val Leu Ser Gln Ser Pro Ala Ile Leu Ser Ala Ser Pro
 1               5                  10                  15

Gly Glu Lys Val Thr Met Thr Cys Arg Ala Ser Ser Ser Val Ser
                20                  25                  30

Tyr Ile His Trp Phe Gln Gln Lys Pro Gly Ser Ser Pro Lys Pro
                35                  40                  45

Trp Ile Tyr Ala Thr Ser Asn Leu Ala Ser Gly Val Pro Val Arg
                50                  55                  60

Phe Ser Gly Ser Gly Ser Gly Thr Ser Tyr Ser Leu Thr Ile Ser
                65                  70                  75

Arg Val Glu Ala Glu Asp Ala Ala Thr Tyr Tyr Cys Gln Gln Trp
                80                  85                  90

Thr Ser Asn Pro Pro Thr Phe Gly Gly Gly Thr Lys Leu Glu Ile
                95                 100                 105

Lys

<210> SEQ ID NO 2
<211> LENGTH: 121
<212> TYPE: PRT
<213> ORGANISM: Mus musculus

<400> SEQUENCE: 2

Gln Val Gln Leu Gln Gln Pro Gly Ala Glu Leu Val Lys Pro Gly
 1               5                  10                  15

Ala Ser Val Lys Met Ser Cys Lys Ala Ser Gly Tyr Thr Phe Thr
                20                  25                  30

Ser Tyr Asn Met His Trp Val Lys Gln Thr Pro Gly Arg Gly Leu
                35                  40                  45

Glu Trp Ile Gly Ala Ile Tyr Pro Gly Asn Gly Asp Thr Ser Tyr
                50                  55                  60

Asn Gln Lys Phe Lys Gly Lys Ala Thr Leu Thr Ala Asp Lys Ser
                65                  70                  75

Ser Ser Thr Ala Tyr Met Gln Leu Ser Ser Leu Thr Ser Glu Asp
                80                  85                  90

Ser Ala Val Tyr Tyr Cys Ala Arg Ser Thr Tyr Tyr Gly Gly Asp
                95                 100                 105

Trp Tyr Phe Asn Val Trp Gly Ala Gly Thr Thr Val Thr Val Ser
               110                 115                 120

Ala

COMBINATION THERAPIES FOR B-CELL LYMPHOMAS COMPRISING ADMINISTRATION OF ANTI-CD20 ANTIBODIES

CROSS-REFERENCE TO RELATED APPLICATIONS

This application is a divisional application of U.S. patent application Ser. No. 11/840,956, filed Aug. 18, 2007 (now U.S. Pat. No. 8,329,172), which is a continuation of U.S. patent application Ser. No. 10/196,732, filed Jul. 17, 2002 (abandoned), which is a continuation of U.S. patent application Ser. No. 09/372,202, filed Aug. 11, 1999, (now U.S. Pat. No. 6,455,043) which claims priority under 35 U.S.C. Section 119(e) and the benefit of U.S. Provisional Application Ser. No. 60/096,180 filed Aug. 11, 1998, the disclosures of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Apr. 4, 2014, is named GNE-0375R1C2D4US_SL.txt and is 2,517 bytes in size.

FIELD OF THE INVENTION

The invention relates to the use of anti-CD20 antibodies or fragments thereof in the treatment of B-cell lymphomas, particularly the use of such antibodies and fragments in combined therapeutic regimens.

BACKGROUND OF THE INVENTION

The use of antibodies to the CD20 antigen as diagnostic and/or therapeutic agents for B-cell lymphoma has previously been reported. CD20 is a useful marker or target for B-cell lymphomas as this antigen is expressed at very high densities on the surface of malignant B-cells, i.e., B-cells wherein unabated proliferation can lead to B-cell lymphomas.

CD20 or Bp35 is a B-lymphocyte-restricted differentiation antigen that is expressed during early pre-B-cell development and remains until plasma cell differentiation. It is believed by some that the CD20 molecule may regulate a step in the B-cell activation process which is required for cell cycle initiation and differentiation. Moreover, as noted, CD20 is usually expressed at very high levels on neoplastic ("tumor") B-cells. The CD20 antigen is appealing for targeted therapy, because it does not shed, modulate, or internalize.

Previous reported therapies involving anti-CD20 antibodies have involved the administration of a therapeutic anti-CD20 antibody either alone or in conjunction with a second radiolabeled anti-CD20 antibody, or a chemotherapeutic agent.

In fact, the Food and Drug Administration has approved the therapeutic use of one such anti-CD20 antibody, RITUXAN®, for use in relapsed and previously treated low-grade non-Hodgkin's lymphoma (NHL). Also, the use of RITUXAN® in combination with a radiolabeled murine anti-CD20 antibody has been suggested for the treatment of B-cell lymphoma.

However, while anti-CD20 antibodies and, in particular, RITUXAN® (U.S.; in Britain, MABTHERA®; in general Rituximab), have been reported to be effective for treatment of B-cell lymphomas, such as non-Hodgkin's lymphoma, the treated patients are often subject to disease relapse. Therefore, it would be beneficial if more effective treatment regimens could be developed. More specifically, it would be advantageous if anti-CD20 antibodies had a beneficial effect in combination with other lymphoma treatments, and if new combined therapeutic regimens could be developed to lessen the likelihood or frequency of relapse. Also, it would be helpful if current treatment protocols for B-cell lymphoma were improved whereby patients with lymphomas which are refractory to other treatment methods could be treated with chimeric or radiolabeled anti-CD20 antibodies. It would also be helpful if treatment with anti-CD20 antibodies, particularly in combination with other treatments, could be used as therapy for other types of lymphoma besides low grade, follicular non-Hodgkin's lymphoma (NHL).

SUMMARY OF THE INVENTION

The present invention discloses combined therapeutic treatments for B-cell lymphomas, and reports the benefits of treating relapsed or refractory B-cell lymphomas with chimeric and radiolabeled anti-CD20 antibodies. In particular, it has been found that treatment with anti-CD20 antibody provides a beneficial synergistic effect when administered in combination with cytokines, radiotherapy, myeloablative therapy, or chemotherapy. Surprisingly, patients who had prior bone marrow or stem cell transplantation had an unexpected increase in the over-all response rate when compared with patients with no prior therapy.

DETAILED DESCRIPTION OF THE INVENTION

This invention encompasses combined therapeutic regimens for the treatment of B-cell lymphomas. In general, such methods include a method for treating relapsed B-cell lymphoma, where a patient having prior treatment for lymphoma has relapsed and is administered a therapeutically effective amount of a chimeric anti-CD20 antibody. Such prior treatments can include, for example, previous treatment with anti-CD20 antibodies, treatments which included a bone marrow or stem cell transplantation, radiotherapy and chemotherapy. The previous chemotherapy may be selected from a wide group of chemotherapeutic agents and combination regimens, including CHOP, ICE, Mitozantrone, Cytarabine, DVP, ATRA, Idarubicin, hoelzer chemotherapy regime, La La chemotherapy regime, ABVD, CEOP, 2-CdA, FLAG & IDA with or without subsequent G-CSF treatment), VAD, M & P, C-Weekly, ABCM, MOPP and DHAP.

Also included in the methods of the invention are methods for treating a subject having B-cell lymphoma wherein the subject is refractory for other therapeutic treatments, including all those listed above, i.e., treatment with chimeric anti-CD20 antibody, treatments which included a bone marrow or stem cell transplantation, radiotherapy and chemotherapy. In particular, encompassed are methods of treating a patient who has not exhibited appreciable tumor remission or regression after administration of a chimeric anti-CD20 antibody, comprising administering to said patient a radiolabeled anti-CD20 antibody.

In particular, the methods of treating a patient with a radiolabeled antibody after a chimeric antibody are performed whereby the radiolabeled anti-CD20 antibody is administered from about one week to about two years after said administration of said chimeric anti-CD20 antibody. More particularly, the radiolabeled anti-CD20 antibody is administered from about one week to about nine months after said administration of said chimeric anti-CD20 antibody.

While any anti-CD20 antibodies can be used for the methods of the present invention, a preferred chimeric antibody is C2B8 (IDEC Pharmaceuticals, Rituximab). A preferred radiolabeled antibody is Y2B8, which is a murine antibody labeled with yttrium-90 ($^{90}Y$). However, antibodies with other radiolabels may be used, particularly those labeled with a beta or alpha isotope. Anti-CD19 antibodies may also be used.

One of skill in the art would know the parameters for choosing a particular type of anti-CD20 antibody. For instance, chimeric and humanized antibodies are beneficial for decreased immunogenicity, and for facilitating antibody effector mediated immune reactions via the human constant region domains. Murine and other mammalian antibodies, in contrast, are beneficial for delivering a radiolabel to the tumor cell, as such antibodies generally have a decreased half-life in vivo.

Antibody treatments performed initially to which patients are refractory or have relapsed may include initial treatments with chimeric antibodies or mammalian antibodies. Also encompassed are initial treatments with other antibodies, including anti-CD19 antibodies and anti-Lym antibodies, and treatments with antibodies labeled with cytotoxic moieties, such as toxins, and radiolabels, e.g., ONCOLYM® (Techniclone) or BEXXAR® (Coulter).

It should be clear that the combined therapeutic regimens of the present invention can be performed whereby said therapies are given simultaneously, i.e., the anti-CD20 antibody is administered concurrently or within the same time frame (i.e., the therapies are going on concurrently, but the agents are not administered precisely at the same time). The anti-CD20 antibodies of the present invention may also be administered prior to or subsequent to the other therapies. Sequential administration may be performed regardless of whether the patient responds to the first therapy to decrease the possibility of remission or relapse.

The combined therapies of the present invention include a method for treating B-cell lymphoma comprising administering at least one chimeric anti-CD20 antibody and at least one cytokine. In particular, the invention includes a method for treating B-cell lymphoma comprising administering a synergistic therapeutic combination comprising at least one anti-CD20 antibody and at least one cytokine, wherein the therapeutic effect is better than the additive effects of either therapy administered alone. Preferred cytokines are selected from the group consisting of alpha interferon, gamma interferon, IL-2, GM-CSF and G-CSF. Again, the anti-CD20 antibody and the cytokine(s) may be administered sequentially, in either order, or in combination.

Also included in the present invention is a method for treating B-cell lymphoma comprising administering to a patient a therapeutically effective amount of a chimeric anti-CD20 antibody before, during or subsequent to a chemotherapeutic regimen. Such a chemotherapy regimen may be selected from the group consisting of, at the very least, CHOP, ICE, Mitozantrone, Cytarabine, DVP, ATRA, Idarubicin, hoelzer chemotherapy regime, La La chemotherapy regime, ABVD, CEOP, 2-CdA, FLAG & IDA with or without subsequent G-CSF treatment), VAD, M & P, C-Weekly, ABCM, MOPP and DHAP.

Also encompassed are methods for treating B-cell lymphoma comprising administering to a patient a therapeutically effective amount of a chimeric anti-CD20 antibody before, during or subsequent to a bone marrow or peripheral stem cell transplant. Such bone marrow transplant may also be accompanied by other therapeutic regimens such as chemotherapy. The antibodies of the present invention may also be used in a method of reducing residual CD20+ tumor cells in bone marrow or stem cells before or after myeloablative therapy by administering to a patient a chimeric anti-CD20 antibody. It may also be possible to use such antibodies in vitro to induce apoptosis of tumor cells and reduce or cure bone marrow or stem cell preparations of residual tumor cells before they are infused back into the patient.

It should be understood that stem cell transplants may be allogeneic or autologous. If the transplant is allogeneic, i.e., from another person, the disclosed therapeutic regimens may include treatments with immunosuppressive drugs before administration of the anti-CD20 antibodies. Coadministration of other drugs designed to enhance acceptance of the transplant and stimulate the production and differentiation of immune cells is also contemplated. For instance, it has been shown that administration of GM-CSF to marrow transplant recipients promotes the development of specific bone marrow cells which in turn produces circulating infection-fighting neutrophils, and increased the survival rate of marrow transplant recipients.

The methods of the present invention may be used to treat a variety of B-cell lymphomas, including low grade/follicular non-Hodgkin's lymphoma (NHL), small lymphocytic (SL) NHL, intermediate grade/follicular NHL, intermediate grade diffuse NHL, high grade immunoblastic NHL, high grade lymphoblastic NHL, high grade small non-cleaved cell NHL, bulky disease NHL and Waldenstrom's Macroglobulinemia. It should be clear to those of skill in the art that these lymphomas will often have different names due to changing systems of classification, and that patients having lymphomas classified under different names may also benefit from the combined therapeutic regimens of the present invention.

For instance, a recent classification system proposed by European and American pathologists is called the Revised European American Lymphoma (REAL) Classification. This classification system recognizes Mantle cell lymphoma and Marginal cell lymphoma among other peripheral B-cell neoplasms, and separates some classifications into grades based on cytology, i.e., small cell, mixed small and large, large cell. It will be understood that all such classified lymphomas may benefit from the combined therapies of the present invention.

The U.S. National Cancer Institute (NCI) has in turn divided some of the REAL classes into more clinically useful "indolent" or "aggressive" lymphoma designations. Indolent lymphomas include follicular cell lymphomas, separated into cytology "grades," diffuse small lymphocytic lymphoma/chronic lymphocytic leukemia (CLL), lymphoplasmacytoid/Waldenstrom's Macroglobulinemia, Marginal zone lymphoma and Hairy cell leukemia. Aggressive lymphomas include diffuse mixed and large cell lymphoma, Burkitt's lymphoma/diffuse small non-cleaved cell lymphoma, Lymphoblastic lymphoma, Mantle cell lymphoma and AIDS-related lymphoma. These lymphomas may also benefit from the combined therapeutic regimens of the present invention.

Non-Hodgkin's lymphoma has also been classified on the basis of "grade" based on other disease characteristics including low-grade, intermediate-grade and high-grade lymphomas. Low-grade lymphoma usually presents as a nodal disease, and is often indolent or slow-growing. Intermediate- and high-grade disease usually presents as a much more aggressive disease with large extranodal bulky tumors. Intermediate- and high-grade disease, as well as low grade NHL, may benefit from the combined therapeutic regimens of the present invention.

The Ann Arbor classification system is also commonly used for patients with NHL. In this system, stages I, II, III, and IV of adult NHL can be classified into A and B categories depending on whether the patient has well-defined generalized symptoms (B) or not (A). The B designation is given to patients with the following symptoms: unexplained loss of more than 10% body weight in the 6 months prior to diagnosis, unexplained fever with temperatures above 38° C. and drenching night sweats. Occasionally, specialized staging systems are used:

Stage I—involvement of a single lymph node region or localized involvement of a single extralymphatic organ or site.

Stage II—involvement of two or more lymph node regions on the same side of the diaphragm or localized involvement of a single associated extralymphatic organ or site and its regional lymph nodes with or without other lymph node regions on the same side of the diaphragm.

Stage III—involvement of lymph node regions on both sides of the diaphragm, possibly accompanying localized involvement of an extralymphatic organ or site, involvement of the spleen, or both.

Stage IV—disseminated (multifocal) involvement of 1 or more extralymphatic sites with or without associated lymph node involvement or isolated extralymphatic organ involvement with distant (non-regional) nodal involvement.

For further details, see The International Non-Hodgkin's Lymphoma Prognostic Factors Project: A predictive model for aggressive non-Hodgkin's lymphoma. New England J. Med. 329(14): 987-994 (1993).

Preferred antibodies, dosage regimens and particular combinations of therapy will now be illustrated by way of the following exemplary data.

Rituximab and Y2B8

Non-Hodgkin's lymphoma (NHL) affects approximately 250,000 people in the United States. The majority of patients with NHL are not cured by chemotherapy, radiotherapy, or high-dose treatment with autologous bone marrow (ABMT) or peripheral blood stem cell (PBSC) support.

Approximately 80% of non-Hodgkin's lymphomas are B-cell malignancies and >95% of these express the CD20 antigen on the cell surface. This antigen is an attractive target for immunotherapy because it is found exclusively on B-cells, and not on hematopoietic stem cells, pro-B-cells, normal plasma cells, or other normal tissues. It is not shed from the cell surface and does not modulate upon antibody binding (1).

Rituximab is one of a new generation of monoclonal antibodies developed to overcome limitations encountered with murine antibodies, including short half-life, limited ability to stimulate human effector functions, and immunogenicity (2,3).

Rituximab is a genetically engineered monoclonal antibody with murine light- and heavy-chain variable regions and human gamma I heavy-chain and kappa light-chain constant regions. The chimeric antibody is composed of two heavy chains of 451 amino acids and two light chains of 213 amino acids and has an approximate molecular weight of 145 kD. Rituximab is more effective than its murine parent in fixing complement and mediating ADCC, and it mediates CDC in the presence of human complement (4). The antibody inhibits cell growth in the B-cell lines FL-18, Ramos, and Raji, sensitizes chemoresistant human lymphoma cell lines to diphtheria toxin, ricin, CDDP, doxorubicin, and etoposide, and induces apoptosis in the DHL-4 human B-cell lymphoma line in a dose-dependent manner (5). In humans, the half-life of the antibody is approximately 60 hours after the first infusion and increases with each dose to 174 hours after the fourth infusion. The immunogenicity of the antibody is low; of 355 patients in seven clinical studies, only three (<1%) had a detectable anti-chimeric antibody (HACA) response.

Rituximab was genetically engineered using the murine 2B8 antibody. The 2B8 antibody has also been conjugated to different radiolabels for diagnostic and therapeutic purposes. To this end, copending application Ser. No. 08/475,813 (now U.S. Pat. No. 6,682,734); Ser. No. 08/475,815 (now U.S. Pat. No. 6,399,061) and Ser. No. 08/478,967 (now U.S. Pat. No. 5,843,439), all herein incorporated by reference in their entirety, disclose radiolabeled anti-CD20 conjugates for diagnostic "imaging" of B-cell lymphoma tumors before administration of therapeutic antibody. "In2B8" conjugate comprises a murine monoclonal antibody, 2B8, specific to human CD20 antigen, that is attached to Indium[111] ($^{111}$In) via a bifunctional chelator, i.e., MX-DTPA (diethylenetriaminepentaacetic acid), which comprises a 1:1 mixture of 1-isothiocyanatobenzyl-3-methyl-DTPA and 1-methyl-3-isothiocyanatobenzyl-DTPA. Indium-[111] is selected as a diagnostic radionuclide because it emits gamma radiation and finds prior usage as an imaging agent.

Patents relating to chelators and chelator conjugates are known in the art. For instance, U.S. Pat. No. 4,831,175 of Gansow is directed to polysubstituted diethylenetriaminepentaacetic acid chelates and protein conjugates containing the same, and methods for their preparation. U.S. Pat. Nos. 5,099,069, 5,246,692, 5,286,850, and 5,124,471 of Gansow also relate to polysubstituted DTPA chelates. These patents are incorporated herein in their entirety.

The specific bifunctional chelator used to facilitate chelation in application Ser. Nos. 08/475,813, 08/475,815 and 08/478,967 (now U.S. Pat. Nos. 6,682,734; 6,399,061; and 5,843,439, respectively) was selected as it possesses high affinity for trivalent metals, and provides for increased tumor-to-non-tumor ratios, decreased bone uptake, and greater in vivo retention of radionuclide at target sites, i.e., B-cell lymphoma tumor sites. However, other bifunctional chelators are known in the art and may also be beneficial in tumor therapy.

Also disclosed in application Ser. Nos. 08/475,813, 08/475,815 and 08/478,967 (now U.S. Pat. Nos. 6,682,734; 6,399,061; and 5,843,439, respectively) are radiolabeled therapeutic antibodies for the targeting and destruction of B-cell lymphomas and tumor cells. In particular, the Y2B8 conjugate comprises the same anti-human CD20 murine monoclonal antibody, 2B8, attached to yttrium-[90] ($^{90}$Y) via the same bifunctional chelator. This radionuclide was selected for therapy for several reasons. The 64 hour half-life of $^{90}$Y is long enough to allow antibody accumulation by the tumor and, unlike e.g. $^{131}$I, it is a pure beta emitter of high energy with no accompanying gamma irradiation in its decay, with a range of 100 to 1000 cell diameters. The minimal amount of penetrating radiation allows for outpatient administration of $^{90}$Y-labeled antibodies. Furthermore, internalization of labeled antibodies is not required for cell killing, and the local emission of ionizing radiation should be lethal for adjacent tumor cells lacking the target antigen.

Because the $^{90}$Y radionuclide was attached to the 2B8 antibody using the same bifunctional chelator molecule MX-DTPA, the Y2B8 conjugate possesses the same advantages discussed above, e.g., increased retention of radionuclide at a target site (tumor). However, unlike $^{111}$In, it cannot be used for imaging purposes due to the lack of gamma radiation associated therewith. Thus, a diagnostic "imaging" radionuclide, such as $^{111}$In, can be used for determining the location and relative size of a tumor prior to and/or following administration of therapeutic chimeric or $^{90}$Y-labeled antibodies in the combined regimens of the invention. Additionally, indium-labeled antibody enables dosimetric assessment to be made.

Depending on the intended use of the antibody, i.e., as a diagnostic or therapeutic reagent, other radiolabels are known in the art and have been used for similar purposes. For instance, radionuclides which have been used in clinical diagnosis include $^{131}$I, $^{125}$I, $^{123}$I, $^{99}$Tc, $^{67}$Ga, as well as $^{111}$In. Antibodies have also been labeled with a variety of radionuclides for potential use in targeted immunotherapy (Peirersz et al. (1987) The use of monoclonal antibody conjugates for the diagnosis and treatment of cancer. *Immunol. Cell Biol.* 65: 111-125). These radionuclides include $^{188}$Re and $^{186}$Re as well as $^{90}$Y, and to a lesser extent $^{199}$Au and $^{67}$Cu. I-(131) has also been used for therapeutic purposes. U.S. Pat. No. 5,460,785 provides a listing of such radioisotopes and is herein incorporated by reference.

As reported in copending application Ser. Nos. 08/475,813, 08/475,815 and 08/478,967 (now U.S. Pat. Nos. 6,682,734; 6,399,061; and. 5,843,439, respectively), administration of the radiolabeled Y2B8 conjugate, as well as unlabeled chimeric anti-CD20 antibody, resulted in significant tumor reduction in mice harboring a B-cell lymphoblastic tumor. Moreover, human clinical trials reported therein showed significant B-cell depletion in lymphoma patients infused with chimeric anti-CD20 antibody. In fact, chimeric 2B8 has recently been heralded the nation's first FDA-approved anti-cancer monoclonal antibody under the name of RITUXAN®. Thus, at least one chimeric anti-CD20 antibody has been shown to demonstrate therapeutic efficacy in the treatment of B-cell lymphoma.

In addition, U.S. application Ser. No. 08/475,813 (now U.S. Pat. No. 6,682,734) herein incorporated by reference, discloses sequential administration of RITUXAN®, a chimeric anti-CD20, with both or either indium-labeled or yttrium-labeled marine monoclonal antibody. Although the radiolabeled antibodies used in these combined therapies are murine antibodies, initial treatment with chimeric anti-CD20 sufficiently depletes the B-cell population such that the HAMA response is decreased, thereby facilitating a combined therapeutic and diagnostic regimen.

Thus, in this context of combined immunotherapy, murine antibodies may find particular utility as diagnostic reagents. Moreover, it was shown in U.S. application Ser. No. 08/475,813 (now U.S. Pat. No. 6,399,061) that a therapeutically effective dosage of the yttrium-labeled anti-CD20 antibody following administration of RITUXAN® is sufficient to (a) clear any remaining peripheral blood B-cells not cleared by the chimeric anti-CD20 antibody; (b) begin B-cell depletion from lymph nodes; or (c) begin B-cell depletion from other tissues.

Thus, conjugation of radiolabels to cancer therapeutic antibodies provides a valuable clinical tool which may be used to assess the potential therapeutic efficacy of such antibodies, create diagnostic reagents to monitor the progress of treatment, and devise additional therapeutic reagents which may be used to enhance the initial tumor killing potential of the chimeric antibody. Given the proven efficacy of an anti-CD20 antibody in the treatment of non-Hodgkin's lymphoma, and the known sensitivity of lymphocytes to radioactivity, it would be highly advantageous for such chimeric and radio-labeled therapeutic antibodies to find use in combined therapeutic regimens which decrease the frequency of relapsed or refractory non-Hodgkin's lymphoma. In addition, it would be beneficial if such combined therapeutic regimens found use in the treatment of other B-cell lymphomas.

Low-Grade or Follicular NHL

Single-Agent Studies with Relapsed or Refractory NHL

FDA approval of Rituximab was based on five single-agent studies primarily in patients with low-grade or follicular NHL. An early Phase I study of single Rituximab infusions ranging from 10-500 mg/m² demonstrated that the maximum tolerated dose had not been reached; however, the length of infusion time at the highest dose was not considered feasible for outpatient therapy. The ORR in 15 patients was 13% (Table 1)(6).

TABLE 1

Rituximab: Summary of Efficacy Results

| Study Description | Indication | N* | ORR | CR | PR | Median DR (months) | Median TIP (months) | References |
|---|---|---|---|---|---|---|---|---|
| Phase I/II, Single-Dose Single Agent | Relapsed B-Cell Lymphoma | 15 | 2 (13%) | 0 (0%) | 2 (13%) | NA† | 8.1 | 6 |
| Phase I/II, Multiple-Dose Dose-Ranging | Relapsed Low-, Intermediate-, and High-Grade Lymphoma | 34 | 17 (50%) | 3 (9%) | 14 (41%) | 8.6 | 10.2 | 7 |
| Phase II; Multiple-Dose Combined with CHOP | Newly Diagnosed and Relapsed Low-Grade or Follicular B-Cell Lymphoma | 38 | 38 (100%) | 22 (58%) | 16 (42%) | 35.3+ | 36.7+ | 21, 22 |
| Phase III, Multiple-Dose Single-Agent | Relapsed Low-Grade or Follicular B-Cell Lymphoma | 151 | 76 (50%) | 9 (6%) | 67 (44%) | 11.6 | 13.2 | 8, 9 |
| Phase II, Multiple-Dose Single-Agent | Relapsed Low-Grade or Follicular B-Cell Lymphoma | 35 | 21 (60%) | 5 (14%) | 16 (46%) | 13.4+ | 19.4+ | 13 |
| Phase II, Multiple-Dose, Combined with Interferon | Relapsed Low-Grade or Follicular B-Cell Lymphoma | 38 | 17 (45%) | 4 (11%) | 13 (34%) | 22.3+ | 25.2+ | 29 |
| Phase II, Multiple-Dose, Single-Agent | Relapsed Low-Grade or Follicular B-Cell Lymphoma, Bulky Disease | 28 | 12 (43%) | 1 (4%) | 11 (39%) | 5.9 | 8.1 | 14 |
| Phase II, Multiple-Dose, Single-Agent | Relapsed Low-Grade or Follicular B-Cell Lymphoma, Retreatment | 57 | 23 (40%) | 6 (11%) | 17 (29%) | 15.0+ | 16.7+ | 19, 20 |
| Phase II, Multiple-Dose Combined with CHOP Modality | Previously Untreated Intermediate- or High-Grade Lymphoma | 30 | 29 (96%) | 19 (63%) | 10 (33%) | 1 I+ | 17+ | 34 |
| Phase II, Alternative Multiple Dosing | Intermediate- or High-Grade B-Cell Lymphoma | 54 | 17 (32%) | 5 (9%) | 12 (22%) | NA† | 8.2+ | 33 |

In Phase I of a Phase I/II dose-ranging study, patients received 125-375 mg/m² administered as four weekly infusions. No dose-related toxicities were demonstrated, and 375 mg/m² was chosen as the Phase II dose. Tumor regressions were observed in 17 of 37 (46%) patients who received this dose, including 3 (8%) complete responses (CR) and 14 (38%) partial responses PR (7).

A subsequent single-arm pivotal study of Rituximab infused at 375 mg/m² weekly times four was conducted in 166 patients with relapsed or refractory, low-grade or follicular NHL (International Working Formulation [IWF] Types A-D and REAL classification, small lymphocytic lymphoma, Follicular center, follicular Grades I, II, III(8)). Patients with tumor masses >10 cm or with >5000 lymphocytes/μL in the peripheral blood were excluded from this study. The median age was 58 years (105 men and 61 women) and the median number of prior treatments was three. Bone marrow involvement was present in 56% of 149 patients evaluated. Forty-five percent had ≥2 extranodal sites and 41% had bulky disease (≥5 cm).

Complete response required the regression of all lymph nodes to <1×1 cm² demonstrated on two occasions at least 28 days apart on neck, chest, abdomen, and pelvic CT scans, resolution of all symptoms and signs of lymphoma, and normalization of bone marrow, liver, and spleen. Partial response required a ≥50% decrease in the sum of the products of perpendicular measurements of lesions without any evidence of progressive disease for at least 28 days. Patients who did not achieve a CR or PR were considered non-responders, even if a net decrease (>50%) of measurable disease was observed. Time to progression was measured from the first infusion until progression.

The overall response rate (ORR) was 48% with a 6% CR and a 42% PR rate (8). The median time to progression (TTP) for responders was 13.2 months and the median duration of response (DR) was 11.6 months. Twenty-two of 80 (28%) responders remain in ongoing remission at 20.9+ to 32.9+ months (9).

Administration of Rituximab resulted in a rapid and sustained depletion of B-cells. Circulating B-cells were depleted within the first three doses with sustained depletion for up to six to nine months post-treatment in 83% of patients. Median B-cell levels returned to normal by 12 months following treatment. Although median NK cell counts remained unchanged, a positive correlation was observed between higher absolute NK cell counts at baseline and response to Rituximab (10).

Several baseline prognostic factors were analyzed to determine their correlation to response. Significantly, in 23 patients relapsed after ABMT or PBSC, the ORR was 78% versus 43% in patients who did not undergo prior high-dose therapy (p<0.01). In a multivariate analysis, the ORR was higher in patients with follicular NHL as compared with small lymphocytic lymphoma (58% vs. 12%, p<0.01), and higher in patients with chemosensitive relapse as compared with chemoresistant relapse (53% vs. 36%, p=0.06). No effect on response rate was associated with: age >60 years, extranodal disease, prior anthracycline therapy, or bone marrow involvement.

A statistically significant correlation was found between the median serum antibody concentration and response at multiple time points during treatment and follow up (11).

Serum levels of antibody were higher in patients with follicular NHL compared with small lymphocytic lymphoma. Mean serum antibody was also inversely correlated with measurements of tumor bulk and with the number of circulating B-cells at baseline. The association of lower serum antibody concentrations with higher numbers of circulating NHL cells and with higher tumor bulk suggest that the main mode of antibody clearance is to tumor cells. The association of high serum antibody concentrations with response and lower tumor bulk or circulating cells suggests that higher or more doses of Rituximab may be necessary to induce responses in some subsets of patients, such as those with bulky disease.

Nevertheless, responses were seen with Rituximab in 43% of patients with tumors >5 cm and in 35% of patients with tumors >7 cm, suggesting that treatment of patients with bulky disease with Rituximab is feasible. This is surprising considering it was long thought that antibody therapy is not conducive to treating bulky disease due to the compact nature of the tumors.

In a study conducted in Japan (12), patients with relapsed B-cell lymphoma were treated with either 250 mg/m² (N=4) or 375 mg/m² (N=8) of Rituximab weekly times four. Of 11 evaluable patients, 8 had follicular NHL, 2 had diffuse large-cell NHL, and one had mantle-cell lymphoma. Two of the 11 had a CR and 5 had a PR for an ORR of 64%; all responders had follicular histology.

Because Rituximab serum levels and response were positively correlated in previous studies, a Phase II study of eight weekly doses of 375 mg/m² Rituximab was conducted in low-grade or follicular NHL patients. The ORR was 60% in evaluable patients, with a 14% CR and a 46% PR rate. Median values for TTP in responders and DR were 13.4+ months and 19.4+ months, respectively (13). Though it is difficult to compare across studies, it appears that TTP and DR may be improved by using more doses.

Contrary to early assumptions about antibody therapy being useful only in micrometastatic disease, Rituximab® is quite active in high bulk disease. In a separate study, 31 patients with relapsed or refractory, bulky low-grade NHL (single lesion of >10 cm in diameter) received 375 mg/m² Rituximab as four weekly infusions. Twelve of 28 evaluable patients (43%) demonstrated a CR (1, 4%) or PR (11, 39%) (14).

Waldenstrom's Macroglobulinemia

Waldenstrom's Macroglobulinemia (WM) is a malignancy wherein B lymphocytes secrete excessive amounts of IgM antibodies. WM usually occurs in people over sixty, but has been detected in adults in their early thirties. WM today is considered a rare incurable indolent malignancy, which has in the past been treated by plasmaphoresis to reduce serum viscosity. Chemotherapeutic drugs such as an alkylating agent and a corticosteroid are often prescribed. The most recommended drug for WM has been Leustatin (2CdA).

A report on seven patients with Waldenstrom's macroglobulinemia where the patients were treated with Rituximab (375 mg/m² weekly times 4)(15) noted responses in 4 (57%) of patients. Median progression-free survival was 8 months (range 3-27+ months). Thus, Rituximab should be useful in combined therapeutic protocols, particularly with chemotherapeutic reagents such as 2CdA.

Chronic Lymphocytic Leukemia (CLL)

CLL is the liquid (leukemic) equivalent of small lymphocytic lymphoma (SLL). Patients with SLL had lower serum levels and a lower response rate when treated with the standard dose of Rituximab than patients with other low-grade NHL subtypes. This is probably due to the very high levels of circulating tumor cells in patients with CLL, and because malignant cells involved in CLL are thought to have reduced levels of expression of CD20 on the cell surface.

Nevertheless, the present inventors have discovered that hematologic malignancies such as CLL may be treated with Rituximab. A recent clinical study evaluated treatment of CLL patients at higher doses of Rituximab (16). All patients receive a first dose of 375 mg/m³ to minimize infusion-relapsed side effects. Subsequent weekly dosages (3) remained the same but were given at an increased dose level. Sixteen patients have been treated at dosages of 500-1500 mg/m³. Medium age was 66 years (range, 25-78). Eighty-one percent had end-stage III-IV disease. Medium white blood cell count was $40 \times 10^9$/L (range, 4-200), Hgb 11.6 g/dl (range, 7.7-14.7), platelets $75 \times 10^9$/L, (range, 16-160), median $\beta_2$ immunoglobulin was 4.5 mg/L (range, 3.1-9.2). Median numbers of prior therapies was 2.5 (range 1-9). Sixty percent of patients were refractory to treatment. Two patients developed severe hypertension with the first dose (375 mg/m²); another one received further therapy. Toxicity at subsequent escalated dosages has been mild although no patient at the 1500 mg/m² dose level has been fully evaluated. Eight patients have completed therapy (4 at 500 mg/m², 3 at 650 mg/m², 1 at 825 mg/m²). One patient treated at 560 mg/m² achieved full remission. One patient has progressive lymphocytosis on treatment and all other patients had reduction in peripheral blood lymphocytosis but less effect on lymph nodes. Dose escalation studies are ongoing.

Another approach to improving response in CLL patients is to upregulate the CD20 antigen using cytokines. In an in vitro study, mononuclear cells from CLL patients were incubated for 24 hours with various cytokines. Flow cytometry results showed significant up-regulation by IL-4, GM-CSF, and TNF-alpha (17). In fact, recent data suggests that the upregulation of CD20 observed on CLL cells may be limited to tumor cells (Venogopal et al. Poster—PanPacific Lymphoma meeting, June 1999. Cytokine-induced upregulation of CD20 antigen expression in chronic lymphocytic leukemia (CLL) cells may be limited to tumor cells). Preliminary data also suggest that interferon alpha also upregulates CD20 on CLL cells after only 24 hours when applied at a concentration of 500 to 1000 U/ml.

Thus, by administering certain cytokines to CLL patients prior to or concurrently with administration of Rituximab, the expression of CD20 on the surface of malignant B-cells may be upregulated, thereby rendering CD20, as well as other cell surface markers such as CD19, a more attractive target for immunotherapy. A collaborative study has been initiated to test for optimal cytokine doses for CD20 upregulation in vivo. The study protocol involves treating ten patients initially with GM-CSF at 250 mcg/m² SQ QD X 3, ten patients with IL-4 mcg/kg SQ QD X 3, and ten patients with G-CSF at 5 mcg/kg SQ QD X 3. Mononuclear cells will be separated by Ficon Hypaque centrifugation for apoptotic studies to determine if upregulation of CD20 translates to enhanced killing of tumor cells by Rituximab.

Antibody treatment of CLL can be combined with other conventional chemotherapeutic treatments known to be useful for the treatment of CLL. The most frequently used single agent for CLL is chlorambucil (leukeran), given either as 0.1 mg/kg daily or 0.4 to 1.0 mg/kg every 4 weeks. Chlorambucil is often combined with oral prednisone (30 to 100 mg/m²/d), which is useful in the management of autoimmune cytopenias. Cyclophosphamide is an alternative to chlorambucil, the usual dose being 1-2 g/m² every 3-4 weeks together with vincristine and steroids (e.g., COP regimen).

Various drug combinations have been used for CLL, including COP (cyclophosphamide, Oncovin, and prednisone), and CHOP (these three drugs plus doxorubicin). Fludarabine has shown an effect in the treatment of CLL, and gave an ORR of 50% in a group of patients treated with 25-30 mg/m²/d every 3-4 weeks. http://www.cancernetwork.com. Although some patients have been shown to be refractory for fludarabine. Such patients may also be resistant to 2-CdA because often, patients who are refractory to fludarabine are also refractory to 2-CDA (O'Brien et al. N. Engl. J. Med. 330: 319-322 (1994)).

Hence, anti-CD20 antibody therapy will be particularly useful for patients who are refractory or who have relapsed after treatment with chemotherapeutic drugs. Rituximab therapy may also be combined with radiotherapy in these patients. TBI with a low fraction size of 15 cGy to total doses of 75 to 150 cGy has been shown to be effective in about one-third of patients.

A Phase II trial is currently being conducted by CALGB in CLL patients. Rituximab and fludarabine are administered concurrently, followed by Rituximab consolidation versus fludarabine induction followed by Rituximab.

Rituximab with Myeloablative Therapy

Myeloablative therapy has yielded responses in indolent lymphomas; however, residual tumor cells may remain despite high-dose therapy and the PBSC reinfused may contain tumor cells. Rituximab is being used before stem cell mobilization and after transplant to reduce residual CD20+ tumor cells and contamination of the bone marrow or stem cells harvested. Interim results demonstrated that no CD20+ cells were detectable in harvested cells. Eighteen of 24 patients achieved engraftment and the treatment was well tolerated. PCR testing is ongoing to evaluate residual tumor cells (18).

Retreatment of Relapsed Low-Grade NHL with Rituximab

A trial evaluating retreatment of 53 patients who had responded to Rituximab and later relapsed has been reported (19). Seven of 56 evaluable patients (13%) obtained a CR and 16 a PR (29%), for an ORR of 42%. Four patients who had a second response received a third treatment; 3 of these responded.

After treatment with two courses of Rituximab, one patient's tumor, initially classified as follicular, small cleaved cell NHL, no longer expressed the CD20 antigen and was unresponsive to Rituximab at the time of transformation to diffuse, large-cell NHL (20).

Thus, while retreatment with Rituximab is effective for treating patients who have relapsed after prior treatment with Rituximab, there may be an increased incidence of CD20- tumor cells after secondary treatment. This observation supports the utility of the combined therapeutic treatment regimens described herein.

Combination of Rituximab and CHOP Chemotherapy for Low-Grade NHL

Chemotherapy with cyclophosphamide, doxorubicin, vincristine, and prednisone (CHOP) is an effective first-line therapy for low-grade or follicular NHL. Though initial response rates are high, relapse eventually occurs and subsequent chemotherapy regimens produce remissions with shorter durations. A Phase II trial was initiated to evaluate the combination of CHOP and Rituximab (21) in newly diagnosed and relapsed low-grade or follicular NHL because their mechanisms of action are not cross-resistant, and Rituximab is synergistic with certain cytotoxic drugs, including doxorubicin (5).

Twenty-nine of 38 patients received no prior anticancer therapy. CHOP was administered at standard doses every three weeks for six cycles with six infusions of Rituximab (375 mg/m²). Rituximab infusions 1 and 2 were administered on Days 1 and 6 before the first CHOP cycle, which started on Day 8. Rituximab infusions 3 and 4 were given 2 days before the third and fifth CHOP cycles, respectively, and infusions 5 and 6 were given on Days 134 and 141, respectively, after the sixth CHOP cycle.

In this combination study, 100% of the 38 patients treated responded (CR, 58%; PR, 42%). Of 35 evaluable patients who completed treatment, there were 63% CR, and 37% PR (21). Median DR is 35.3+ months with median progression-free survival not reached after a median observation time of 36.7+ months. Twenty patients are still in remission after 36+ months to 53.4+ months (22). This DR is impressive even for first-line treatment, and 24% of this trial population had relapsed after chemotherapy.

In a study to be conducted by CALGB, 40 patients with low-grade NHL will receive Rituximab weekly times 8 and oral cyclophosphamide daily starting on Day 8. Twenty patients will receive Rituximab alone for 8 weekly doses.

A Phase III study conducted by ECOG in patients with low-grade NHL is comparing the combination of cyclophosphamide and fludarabine (Arm A) with standard CVP therapy (Arm B). In the randomization to Arm A or Arm B, patients are stratified by age, tumor burden, histology, and B symptoms. Responders in both arms will undergo a second randomization to Rituximab maintenance therapy (375 mg/m$^2$ weekly times 4 every 6 months for 2 years (Arm C) or to observation (Arm D).

Combination of Rituximab with Cytokines

Rituximab Plus Interferon Alpha

Interferon is a cytokine involved in modulating the immune system (23). Mechanisms by which interferon may increase the effectiveness of antibodies include the potentiation of antigen expression (24), increased targeting of antibodies into tumors (25,26), and enhanced cytotoxicity of immunotoxins (27).

In a combination trial, interferon-alpha (Roferon-A), a cytokine with a single-agent clinical activity in NHL (28), and Rituximab were given to patients with relapsed low-grade or follicular NHL. Interferon-alpha (2.5 or 5 MIU) was administered subcutaneously, three times weekly for 12 weeks. Rituximab® was administered by IV infusion weekly for four doses (375 mg/m$^2$) starting on the fifth week of treatment. The ORR was 45% (17/38 patients); 11% had a CR and 34% had a PR. Kaplan-Meier estimates of the median DR and TTP in responders were 22.3+ and 25.2+ months, respectively (29). Previous combination studies of interferon-alpha and chemotherapeutic regimens containing anthracyclines yielded prolonged time to progression, but did not consistently increase response or survival rates (30-32). These early results suggest that the combination of Rituximab and interferon-alpha may prolong the time to progression relative to Rituximab alone.

Rituximab Plus G-CSF

In a separate study, Rituximab and G-CSF are being evaluated in relapsed low-grade NHL. It has been demonstrated in vitro as well as in vivo in healthy volunteers that G-CSF, via its effect on myeloid precursor cells, induces FcRI-positive neutrophils that are capable of functioning as effector cells in ADCC. Therefor, a Phase VII study was initiated to evaluate the toxicity and efficacy of the combined treatment.

Both in Phase I and Phase II, patients were administered a standard dose of G-CSF (5 µg/kg/day) administered for three days, starting 2 days before administration of Rituximab. Phase I consisted of a dose escalation of Rituximab (125, 250, or 375 mg/m$^2$ weekly ×4). Early results in 9 patients evaluated so far yielded an ORR of 67% (44% CR, 22% PR) with minor toxicity in 8 of the 9 patients (33). The most frequent adverse events were fever (⅘ patients), rhinitis (⅘), chills (⅜) and headaches (⅜), which were comparable to the adverse events observed previously in administration of Rituximab alone. The Phase II part of the study has been initiated, which will examine the efficacy of the combination of G-CSF and 375 mg/m$^2$ Rituximab ×4.

Rituximab Plus IL-2

High-dose therapy with autologous peripheral blood stem cells (PBSC) or bone marrow (BM) rescue has been used to treat NHL, however success remains limited by the high risk of relapse, which is 50-80%. In an effort to improve durable remissions post-transplant, immunotherapy including high dose and low dose therapy with IL-2 has been studied in a number of treatment centers. Such studies have suggested that IL-2 therapy does demonstrate early post-transplant anti-Tumor activity.

Initially following autologous transplant, patients display delayed immune reconstitution which potentially results in diminished immune-mediated tumor eradication (43, 44). Indeed, it has been shown that both CD$+ T cells and cytotoxic CD8+ T cells are depressed (45-49). In vitro assays have demonstrated a profound suppression of T cell cytolytic and proliferative responses as well as decreased production of IL-2 in response to mitogens and soluble antigens. However, soluble IL-2 is able to restore these immune responses suggesting that immune cells in patients after autologous transplant are capable of responding to exogenous IL-2 (47). Peripheral blood NK activity also remains lower following BMT than control values and the NK activity is also augmented by addition of exogenous IL-2 (49). These data suggest that administration of IL-2 to patients shortly after stem cell transplant may enhance immune responsiveness at a critical period when tumor burden is minimal and when immune responsiveness in the absence of IL-2 is lacking.

For instance, Caligiuru et al. have shown that IL-2 (Hoffman-LaRoche) administered at $0.45 \times 10^6$ U/M$^2$/day by 24 hour CIV for 12 weeks was able to expand the absolute number of CD56 bright NK cells (50-52). This regimen was administered to non-transplant patients in the outpatient setting with little toxicity.

Animal models have shown that non-LAK inducing low doses of IL-2 dramatically enhances anti-tumor activity when administered with tumor-specific T effector cells (53). In addition, Soiffer et al. (54) administered low doses of IL-2 to 13 autologous BMT or T cell depleted allogeneic BMT recipients undergoing treatment for relapsed leukemia or lymphoma. Enhanced immunological responsiveness was demonstrated in the laboratory with a 5- to 40-fold increase in circulating CD56 bright CD16+ CD3-NK cells. Moreover, this low dose regimen of IL-2 resulted in augmented in vitro killing of the NK targets K562. When Soiffer et al. (55) updated the outcome of 29 allogeneic BMT patients who received low dose IL-2, they found superior survival for these patients (70%) compared to histological controls (30%, p=0.41).

Lauria et al. (56) treated 11 patients with high grade NHL at a median of 42 days after ABMT with IL-2 at a dose of $2 \times 10^6$ IU/m$^2$ god for two weeks and then $3 \times 10^6$ IU/m$^2$ twice a week for a year. Phenotypic analysis showed a persistent and significant (p=0.001) increase in the proportion and absolute number of total lymphocytes and especially of both CD16 and CD56 NK cells after 6 months of therapy. None of the patients progressed with a median follow-up of twenty-two months (range 10-42 months) after starting therapy. In addition, two patients with residual disease after ABMT, one in the liver and second in the lymph nodes, obtained a complete response after 7 and 10 months of IL-2 therapy.

Vey et al. (57) treated 25 patients with refractory or relapsed HD (11 patients) and NHL (14 patients) with low dose IL-2. 48% of the patients had resistant disease at transplant and 84% achieved CR after ABMT. IL-2 was started at a mean of 54 days after transplant and consisted of a first cycle of 5 days followed by 4 cycles of 2 days every other week.

Patients received a mean of $160 \times 10^6$ IU/m$^2$ of IL-2. After a five year follow-up, the probability of survival and DFS is 72% (HD 73% and NHL 70%) and 45% (HD 36% and NHL 48%).

A group at the Fred Hutchinson Cancer Research Center (FHCRC) has recently found that low dose IL-2 therapy was well-tolerated in the outpatient setting, and that remissions in patients treated with low dose IL-2 tended to be longer than without IL-2 treatment. IL-2 therapy was associated with an increase in the number of certain populations of immune cells, including CD8+ CD69+ cells; CD16+ CD8+ cells; CD16+ CD69+ cells; CD16+ CD56+ cells; CD16+ CD122+ cells; CD16+ Dr+ cells; and CD8+ CD56+ cells. There was also an increase in the expression of lytic activity against the tumor targets K562 and Daudi, with a median of 5.9-fold and 6.5-fold increase, respectively. Relapses, when they occurred, occurred at a median of 17.8 months after transplant, and therefor remissions were reported to be characteristically longer than what was historically seen in transplant recipients without IL-2 therapy.

Given the encouraging data gathered from single therapy studies with IL-2 on ABMT transplant recipients, it seemed reasonable to combine IL-2 therapy with Rituximab post transplant, given that Rituximab's biological activity appears to be mediated through ADCC and complement-mediated lytic activity. Thus, a Phase I trial has been initiated in collaboration with the FHCRC to evaluate the safety and potential efficacy of a combined therapeutic regimen.

A separate Phase II study is also being performed to evaluate the efficacy and the incidence of HACA formation in patients receiving low-dose IL-2 and RITUXAN®. A specific objective of this study is to assess whether ADCC is enhanced by in vivo exposure to IL-2 and whether ADCC activity correlates with clinical response. Inclusion criteria for patients are histologically confirmed stage II-IV low-grade, follicular B-cell or mantle cell lymphoma. Mantle cell lymphoma, for the purposes of this clinical study, is defined as CD5+, CD23− (if available) and/or bcl-1+ by immunohistochemistry. Patients who did not respond to or have relapsed following their first treatment with a standard therapy, i.e., chemotherapy, radiotherapy, ABMT and/or immunotherapy, are eligible.

Rituximab Plus GM-CSF for the Treatment of Relapsed Low Grade or Follicular B-Cell Lymphoma Two separate Phase II trials have also been initiated to test the efficacy of combined treatment with Rituximab and GM-CSF. One study involves 40 patients with relapsed low grade B-cell lymphoma, and comprises administering Rituximab at 375 mg/m$^2$ weekly ×4 (d. 1, 8, 15, 22) and GM-CSF (Leukine, Immunex) at 250 mcg sc three times weekly for 8 weeks, starting one hour before the first dose of Rituximab. This study will be used to evaluate the clinical efficacy (overall response rate (ORR), overall complete response rate, time to progression and failure-free survival) of the combined therapeutic regimen, to characterize the safety (qualitative, quantitative, duration and reversibility of adverse events) of the combined therapy, and to determine the effects of the combined therapy on relevant lymphocyte subsets and cytokines. The second study plans to also monitor immunologic parameters to assess the mechanism of killing (complement C3 and C4, CH50, flow cytometry for CD3, CD4, CD8, CD16, CD19 and CD56 and ADCC assay).

Rituximab Plus Gamma-Interferon

Gamma-interferon may also be useful in combined therapy with Rituximab for treating patients with low-grade or higher-grade lymphomas. It is has recently been found that gamma-interferon upregulates CD20 expression on multiple myeloma (MM) patient plasma cells, patient B-cells, as well as on normal donor B-cells (Treon et al., Lugano, 1999). In fact, Treon and colleagues have shown that gamma-interferon augments binding of these cells to Rituximab. Induction of CD20 expression on plasma cells occurred in a dose dependent manner, with upregulation seen with as little as 1 U/ml of interferon gamma. A plateau occurred at 100 U/ml at 48 hours. Thus, gamma-interferon may also be beneficial when administered in combination with Rituximab.

Intermediate-Grade and High-Grade NHL

Single-Agent Studies

In a study conducted in Europe and Australia, alternative dosing schedules were evaluated in 54 relapsed or refractory intermediate- or high-grade NHL patients (34). Rituximab was infused at 375 mg/m$^2$ weekly for 8 doses or at 375 mg/m$^2$ once followed by 500 mg/m$^2$ weekly for 7 doses. The ORR was 31%; (CR 9%, PR 22%) no significant difference between the dosing regimens was observed. Patients with diffuse large-cell lymphoma (N=30) had an ORR of 37% and those with mantle-cell lymphoma (N=12) had an ORR of 33%.

Combination of Rituximab and CHOP Chemotherapy

In another study, 31 patients with intermediate- or high-grade NHL (19 females, 12 males, median age 49) received Rituximab on Day 1 of each of six 21-day cycles of CHOP (35). Of 30 evaluable patients, there were 19 CR (63%) and 10 PR (33%), for an ORR of 96%. This regimen was considered well tolerated and may result in higher response rates than with Rituximab or CHOP alone.

The NCI Division of Cancer Treatment and Diagnosis is collaborating with IDEC Pharmaceuticals Corporation to explore Rituximab treatment in other indications. A Phase II trial of CHOP versus CHOP and Rituximab is being conducted by ECOG, CALGB, and SWOG in older patients (>60 years) with mixed, diffuse large cell, and immunoblastic large cell histology NHL (N=630 planned). This study includes a secondary randomization to maintenance with Rituximab versus non-maintenance.

A Phase III trial of Rituximab and CHOP in 40 patients with previously untreated mantle-cell lymphoma is also ongoing at the Dana Farber Institute. Rituximab® is administered on Day 1 and CHOP is given on Days 1-3 every 21 days for 6 cycles. Accrual for this study has been completed. A Phase II trial of CHOP followed by Rituximab in newly diagnosed follicular lymphoma conducted by SWOG has also been completed. Results of these two trials are being analyzed.

A Phase II trial of CHOP and Rituximab versus CHOP alone in HIV-related NHL conducted by the AIDS Malignancy Consortium is ongoing; 120 patients are planned.

Rituximab after Myeloablative Therapy Relapse

Rituximab has shown promising early results in patients with relapsed intermediate-grade NHL after high-dose therapy with autologous PBSC support. Six of seven patients responded (1 CR and 5 PR) and one patient had stable disease; therapy was well tolerated (36).

Safety Experience

Adverse events and clinical laboratory data from 315 patients in the five single-agent U.S. studies were combined to provide a safety profile of Rituximab in patients with low-grade or follicular NHL. The majority of adverse events were infusion-related and occurred with decreasing frequency after the first infusion. The most common infusion-related events were fever (49%), chills (32%), nausea (18%), fatigue (16%), headache (14%), angioedema (13%), pruritus (10%), and occasionally, hypotension (10%) and bronchospasm (8%). During the treatment period (up to 30 days following the last dose), 10% of patients experienced Grade 3 or 4 adverse events, which were primarily infusion-related or hematologic. Thrombocytopenia (<50,000 platelets/mm$^3$) occurred in 1.3% of patients, neutropenia (<1000/mm$^3$) occurred in 1.9%, and anemia (<8 gm/dL) occurred in 1.0%. Although Rituximab induced B-cell depletion in 70% -80% of patients, abnormally decreased serum immunoglobulins were observed in a minority of patients and the incidence of infection did not appear to be increased.

Hypotension requiring interruption of the Rituximab infusion occurred in 10% of patients and was Grade 3 or 4 in 1%. Angioedema was reported in 13% of patients and was considered serious in one patient. Bronchospasm occurred in 8% of patients; 2% were treated with bronchodilators. A single report of bronchiolitis obliterans was noted. Most patients experienced no further infusion-related toxicities by the second and subsequent infusions. The percentage of patients reporting adverse events upon retreatment was similar to that reported following the first course (14).

Four patients developed arrhythmias during Rituximab infusion. One of the four discontinued treatment because of ventricular tachycardia and supraventricular tachycardias. The other three patients experienced trigeminy (N=1) and irregular pulse (N=2) and did not require discontinuation of therapy. Angina was reported during infusion and myocardial infarction occurred four days post-infusion in one subject with a prior history of myocardial infarction.

The overall incidence of adverse events and Grade 3 and 4 adverse events was higher in patients with bulky disease than in patients with non-bulky disease. The incidence of dizziness, neutropenia, thrombocytopenia, myalgia, anemia, and chest pain was higher in patients with lesions >10 cm. The incidence of Grade 3 or 4 neutropenia, anemia, hypotension, and dyspnea was also higher in patients with bulky disease compared with patients with lesions <10 cm (19).

Since FDA approval of Rituximab for treatment of relapsed or refractory low-grade or follicular NHL in 1997, an estimated 17,000 patients have been treated. In May, 1998, descriptions of eight post-marketing reports of severe infusion-related adverse events associated with the use of Rituximab that resulted in fatal outcomes were summarized. In seven of the eight fatalities, severe symptoms occurred during the first Rituximab infusion. The cause of death was not reported or remains unknown for two of the eight cases. Severe respiratory events, including hypoxia, pulmonary infiltrates, or adult respiratory distress syndrome contributed to six of the eight reported deaths. One patient had a pretreatment lymphocyte count of 600,000/mm$^3$; another, a creatinine of 8; a third, a respiratory rate of 40; and a fourth, pancytopenia. Patients with a high tumor burden or with a high number of circulating malignant cells may be at higher risk and these patients should be monitored closely throughout each infusion.

Most of the adverse events recently described were previously observed in Rituximab clinical studies. One notable exception is an infusion-related syndrome associated with rapid tumor lysis, that was reported in six patients with high numbers of circulating tumor cells (37,38). This syndrome was characterized by fever, rigors, bronchospasm with associated hypoxemia, a rapid decline in peripheral lymphocytes, laboratory evidence of tumor destruction, and transient, severe thrombocytopenia. These patients had diagnoses of B-prolymphocytic leukemia (N=2), chronic lymphocytic leukemia (N=2), mantle-cell lymphoma (N=1), or transformed NHL (N=1); all had elevated circulating lymphocytes, bulky adenopathy, and organomegaly. Although five of these six patients required hospitalization, symptoms resolved and subsequent Rituximab treatments were well tolerated; the last patient refused further therapy and died of progressive disease two weeks later.

In a separate report of seven patients with CLL and one patient with mantle-cell lymphoma, tumor lysis syndrome was observed after the first Rituximab infusion in those patients with lymphocyte counts >10×10$^9$ L, (39).

Radioimmunotherapy with $^{90}$Yttrium-Labeled Anti-CD20 Antibody in Combination with Rituximab Another therapeutic approach to NHL under evaluation is a radiolabeled anti-CD20 antibody (IDEC-Y2B8) in combination with Rituximab. IDEC-Y2B8 ($^{90}$Y-ibritumomab tiuxetan) is a murine IgG$_1$ kappa anti-CD20 antibody conjugated to $^{90}$Y via a chelator, MX-DTPA, which is covalently bound to the antibody. Rituximab (250 mg/m2) is administered prior to IDEC-Y2B8 to deplete peripheral B lymphocytes and improve biodistribution of the radiolabeled antibody.

In a recently reported Phase I/II study (40-42), patients with low-grade NHL (N=34), intermediate-grade NHL (N=14), or mantle-cell lymphoma (N=3) were treated with IDEC-Y2B8. The median age was 60, 71% were male, and 96% were Caucasian. Of 51 patients with relapsed or refractory NHL, 34 (67%) responded to single doses of 0.2, 0.3, or 0.4 mCi/kg of IDEC-Y2B8. The ORR was 82% (28/34) for patients with low-grade or follicular NHL and was 43% (6/14) for patients with intermediate-grade lymphoma. No patients with mantle-cell disease responded.

A Phase III randomized study comparing IDEC-Y2B8 with Rituximab (375 mg/m$^2$ weekly times 4) for treatment of low-grade follicular or transformed NHL patients is ongoing. Another Phase III trial is also being conducted in patients with relapsed NHL who are refractory to Rituximab.

SUMMARY

In the absence of curative therapy for NHL, the objective of treatment is to achieve control of the disease for a meaningful duration and provide relief of tumor-related symptoms without undue toxicity. Treatment with Rituximab is a brief, 22-day outpatient therapy with limited adverse events in most patients. In clinical studies, 50% of evaluable relapsed or chemotherapy refractory low-grade or follicular NHL patients achieved complete or partial responses. These responses were durable without maintenance therapy; the median TTP for responders was 13.2 months and the median DR was 11.6 months in the pivotal study.

Rituximab is approved as a safe and effective treatment for patients with relapsed low-grade or follicular B-cell NHL. It has significant clinical activity, a novel mechanism of action, and compares favorably with alternative therapies in response rate and response duration. Completion of ongoing studies will verify the role of alternative Rituximab regimens and Rituximab in the treatment of other CD20+ B-lymphocyte malignancies.

REFERENCES

1. Press O, Appelbaum F, Ledbetter J, Martin P, Zarling J, Kidd P, Thomas E. Monoclonal antibody 1F5 (anti-CD20) serotherapy of human B-cell lymphomas. *Blood* 1987; 69:584-591.
2. Dillman R. Antibodies as cytotoxic therapy. Journal of Clinical Oncology 1994; 12:1497-1515.
3. Grossbard M, Press O, Appelbaum F, Bernstein I, Nadler L. Monoclonal antibody-based therapies of leukemia and lymphoma. *Blood* 1992; 80:863-878.

4. Reff M, Carner K, Chambers K, Chinn P, Leonard J, Raab R, Newman R, Hanna N, Anderson D. Depletion of B cells in vivo by a chimeric mouse human monoclonal antibody to CD20. *Blood* 1994; 83:435-445.
5. Demidem A, Lam T, Alas S, Hariharan K, Hanna N, Bonavida B. Chimeric anti-CD20 (IDEC-C2B8) monoclonal antibody sensitizes a B cell lymphoma cell line to cell killing by cytotoxic drugs. Cancer Biotherapy & Radiopharmaceuticals 1997; 12:177-186.
6. Maloney D, Liles T, Czerwinski D, Waldichuk C, Rosenberg J, Grillo-López A, Levy R. Phase I clinical trial using escalating single-dose infusion of chimeric anti-CD20 monoclonal antibody (IDEC-C2B8) in patients with recurrent B-cell lymphoma. *Blood* 1994; 84:2457-2466.
7. Maloney D, Grillo-López A, White C, Bodkin D, Schilder R, Neidhart J, Janakiraman N, Foon K, Liles T-M, Dallaire B, Wey K, Royston I, Davis T, Levy R. IDEC-C2B8 (Rituximab®) anti-CD20 monoclonal antibody therapy in patients with relapsed low-grade non-Hodgkin's lymphoma. *Blood* 1997; 90: 2188-2195.
8. McLaughlin P, Grillo-López A, Link B, Levy R, Czuczman M, Williams M, Heyman M, Bence-Bruckler I, White C, Cabanillas F, Jain V, Ho A, Lister J, Wey K, Shen D, Dallaire B. Rituximab® chimeric anti-CD20 monoclonal antibody therapy for relapsed indolent lymphoma: half of patients respond to a 4-dose treatment program. Journal of Clinical Oncology 1998; 16:2825-2833.
9. McLaughlin P, Grillo-López A, Maloney D, Link B, Levy R, Czuczman M, Cabanillas F, Dallaire B, White C. Efficacy controls in long-term follow-up of patients treated with rituximab for relapsed or refractory, low-grade or follicular NHL. *Blood* 1998; 92:414a-415a.
10. Janakiraman N, McLaughlin P, White C, Maloney D, Shen D, Grillo-López A. Rituximab: Correlation between effector cells and clinical activity in NHL. *Blood* 1998; 92 (10 Suppl 1):337a.
11. Berinstein N, Grillo-López A, White C, Bence-Bruckler I, Maloney D, Czuczman M, Green D, Rosenberg J, McLaughlin P, Shen D. Association of serum Rituximab (IDEC-C2B8) concentration and anti-tumor response in the treatment of recurrent low-grade or follicular non-Hodgkin's lymphoma. Annals of Oncology 1998; 9:995-1001.
12. Tobinai K, Kobayashi Y, Narabayashi M, Ogura M, Kagami Y, Morishima Y, Ohtsu T, Igarashi T, Sasaki Y, Kinoshita T, Murate T. Feasibility and pharmacokinetic study of a chimeric anti-CD20 monoclonal antibody (IDEC-C2B8, rituximab) in relapsed B-cell lymphoma. Annals of Oncology 1998; 9:527-534.
13. Piro L, White C, Grillo-López A, Janakiraman N, Saven A, Beck T, Varns C, Shuey S, Czuczman M, Lynch J, Kolitz J, Jain V. Extended Rituxan (anti-CD20 monoclonal antibody) therapy for relapsed or refractory low-grade or follicular non-Hodgkin's lymphoma. 1999; Submitted
14. Davis T, White C, Grillo-López A, Velasquez W, Link B, Maloney D, Dillman R, Williams M, Mohrbacher A, Weaver R, Dowden S, Levy R. Rituximab: First report of a Phase II (PII) trial in NHL patients (pts) with bulky disease. *Blood* 1998; 92 (10 Suppl 1):414a.
15. Byrd J, White C, Thomas S, Veldsquez W, Rosenberg J, Grillo-López A. Rituximab therapy in previously treated Waldenstrom's Macroglobulinemia: Preliminary evidence of activity. *Blood* 1998; 92 (IO Suppl 1): 106(a).
16. O'Brien S, Freireich E, Andreeff M, Lerner S, Keating M. Phase I/III Study of Rituxan in chronic lymphocytic leukemia (CLL). *Blood* 1998; 92:105a, #431.
17. Venugopal P, Sivararnan S, Huang X, Chopra H, O'Brein T, Jajeh A, Preisler H. Upregulation of CD20 expression in chronic lymphocytic leukemia (CLL) cells by in vitro exposure to cytokines. *Blood* 1998; 10:247a.
18. Flinn I, O'Donnell P, Noga S, Vogelsang G, Greyer M, Goodrich A, Abrams R, Marcellus D, Miller C, Jones R., Ambinder R. In vivo purging and adjuvant immunotherapy with Rituximab PBSC transplant for NHL. *Blood* 1998; 92:648a, #2673.
19. Davis T, Levy R, White C, Czuczman M, McLaughlin P, Link B, Varns C, Weaver R, Grillo-López A. Rituximab: Phase II (PII) retreatment (ReRx) study in patients (pts) with low-grade or follicular (LG/F) NHL. *Blood* 1998; 92 (10 Suppl 1):414a.
20. Davis T, Czerwinski D, Levy R. Therapy of B cell lymphoma with anti-CD20 antibodies can result in the loss of CD20 antigen expression. Clinical Cancer Research 1999; 5: In press.
21. Czuczman M, Grillo-López A, White C, Saleh M, Gordon L, LoBuglio F, Jonas C, Klippenstein D, Dallaire B, Varns C. Treatment of patients with low-grade B-cell lymphoma with the combination of chimeric anti-CD20 monoclonal antibody and CHOP chemotherapy. *Journal of Clinical Oncology* 1999; 17:268-276.
22. White C, Czuczman M, Grillo-López A, White C, Saleh M, Gordon L, LoBuglio A, Jonas C, Alkuzweny B, Dowen S. Rituximab/CHOP chemoimmunotherapy in patients (pts) with low grade lymphoma (LG/F NHL): Progression free survival (PFS) after three years (median) follow-up. *Proceedings of ASCO* 1999, In press.
23. Wadler S, Schwartz E. Principles in the biomodulation of cytotoxic drugs by interferons. *Seminars in Oncology* 1992; 19:45-48.
24. Nakamura K, Kubo A, Hosokawa S, Nagaike K, Hashimoto S. Effect of alpha-interferon on anti-alpha-fetoprotein-monoclonal-antibody targeting of hepatoma. *Oncology* 1993; 50:35-40.
25. Greiner J, Guadagni F, Noguchi P, Pestka S, Colcher D, Fisher P, Schlom J. Recombinant interferon enhances monoclonal antibody-targeting of carcinoma lesions in vivo. *Science* 1987; 235:895-898.
26. Murray J, Zukiwski A, Mujoo K, Rosenblum M. Recombinant alpha-interferon enhances tumor targeting of an antimelanoma monoclonal antibody in vivo. *Journal of Biological Response Modifiers* 1990; 9:556-563.
27. Yokota S, Hara H, Luo Y, Seon B. Synergistic potentiation of in vivo antitumor activity of anti-human T-leukemia immunotoxins by recombinant alpha-interferon and daunorubicin. *Cancer Research* 1990; 50:32-37.
28. Grillo-López A, Dallaire B, Shen C, Varns C, McClure A, Caralli V. Treatment options for patients with relapsed low-grade or follicular lymphoma: The role of IDEC-C2B8. Antibody Imunoconjugates and *Radiopharmaceuticals* 1995; 8:60.
29. Davis T, Maloney D, White C, Grillo-López A, Williams M, Weiner G, Sklenar T, Levy R. Combination immunotherapy of low grade or follicular (LG/F) non-Hodgkin's lymphoma (NHL) with Rituximab and alpha interferon: Interim analysis. *Proceedings of the American Society of Clinical Oncology* 1998; 17:11a.
30. Smalley R, Andersen J, Hawkins M, Bhide V, O'Connell M, Oken M, Borden E. Interferon alfa combined with cytotoxic chemotherapy for patients with non-Hodgkin's lymphoma. *New England Journal of Medicine* 1992; 327: 1336-1341.
31. Hagenbeek A, Carde P, Meerwaldt J H, Somers R, Thomas J, De Bock R, Raemaekers J M, van Hoof A, De 31. Wolf-Peeters C, van Glabbeke M. Maintenance of remission with human recombinant interferon alfa-2a in patients with stages In and IV low-grade malignant non-Hodgkin's lymphoma. European Organization for Research and Treatment of Cancer Lymphoma Cooperative Group. *Journal of Clinical Oncology* 1998; 16:41-47.
32. Solal-Céligny P, Lepage E, Brousse N, Tendler C, Brice P, Haioun C, Gabarre J, Pignon B, Tertian G, Bouabdallah R, Rossi J-F, Doyen C, Coiffier B. Doxorubicin-containing regimen with or without interferon alfa-2b for advanced follicular lymphomas: Final analysis of survival and toxicity in the groupe d'etude des lymphomes folliculaires 86 trial. *Journal of Clinical Oncology* 1998; 16:2332-2338.
33. van der Kolk L, Grillo-López A, Gerritsen W, Jonkhoff A, Baars J, van Oers M. Chimeric anti-CD20 monoclonal antibody (rituximab) plus G-CSF in relapsed B-cell lymphoma: A phase I/II clinical trial. *Blood* 1998; 92:241b, #4037.
34. Coiffier B, Haioun C, Ketterer N, Engert A, Tilly H, Ma D, Johnson P, Lister A, Feuring-Buske M, Radford J A, Capdeville R, Diehl V, Reyes F. Rituximab (anti-CD20 monoclonal antibody) for the treatment of patients with relapsing or refractory aggressive lymphoma: a multicenter phase H study. *Blood* 1998; 92:1927-1932.
35. Link B, Grossbard M, Fisher R, Czuczman M, Gilman P, Lowe A, Vose J. Phase II pilot study of the safety and efficacy of rituximab in combination with CHOP chemotherapy in patients with previously untreated- or high-grade NHL. *Proceedings of the American Society of Clinical Oncology* 1998; 17:3a.
36. Tsai, D, Moore H, Porter D, Vaughn D, Luger S, Loh R, Schuster S, Stadtmauer E. Progressive intermediate grade non-Hodgkin's lymphoma after high dose therapy and autologous peripheral stem cell transplantation (PSCT) has a high response rate to Rituximab. *Blood* 1998; 92:415a, #1713.
37. Byrd J, Waselenko J, Maneatis T, Murphy T, Weickrum R, Ward F, White C. Rituximab therapy in hematologic malignancy patients with circulating blood tumor cells: Association with increased infusion-related side effects and rapid tumor lysis. *Blood* 1998; 92 (10 Suppl 1): 106a.
38. Jensen M, Winkler U, Manzke O, Diehl V, Engert A. Rapid tumor lysis in a patient with B-cell chronic lymphocytic leukemia and lymphocytosis treated with an anti-CD20 monoclonal antibody (IDEC-C2B8, rituximab). *Annals of Hematology* 1998; 77:89-91.
39. Winkler U, Jensen M, Manzke O, Tesch H, Bohlen H, Diehl V, Engert A. Severe side effects in patients with B-cell chronic lymphocytic leukemia (CLL) and lymphocytosis treated with the monoclonal antibody Rituximab. *Blood* 1998; 92:285b, #4228.
40. Witzig T, White C, Wiseman G, Gordon L, Emmanouilides C, Raubitschek A, Janakiraman N, Gutheil J, Spies S, Silverman D, Parker E, Grillo-López A. Phase I/II trial of IDEC-Y2B8 radioimmunotherapy for treatment of relapsed or refractory CD20 positive B-cell non-Hodgkin's lymphoma. *Journal of Clinical Oncology* 1999; Submitted.
41. Wiseman G, White C, Witzig T, Gordon L, Emmanouilides C, Raubitschek A, Janakiraman N, Spies S, Silverman D, Gutheil J, Schilder R, Parker E, Rosenberg J, Grillo-López A. IDEC-Y2B8 radioimmunotherapy: Baseline bone marrow involvement and platelet count are better predictors of hematologic toxicity than dosimetry. *Blood* 1998; 92:417a.
42. Witzig T, White C, Wiseman G, Gordon L, Emmanouilides C, Raubitschek A, Janakiraman N, Spies S, Silverman D, Gutheil J, Schilder R, Ding E, Shen D, Grillo-López A. IDEC-Y2B8 Radioimmunotherapy: Responses in patients with splenomegaly. *Blood* 1998; 92:417(a).
43. Witherspoon R P, Lum L G, Storb R Immunologic reconstitution after bone marrow grafting. Semin Hematol 21:2, 1984.
44. Anderson, K C et al. Hematological engraftment and immune reconstitution posttransplant with anti-B1 purged autologous bone marrow. *Blood* 69:597, 1987.
45. Lum L G. Kinetics of immune reconstitution after human marrow transplantation. *Blood* 69:369, 1987.
46. Azogui O., Gluckman E., Fradelizi, D., Inhibition of IL-2 production after human allogeneic bone marrow transplantation. J. Immunol 131:1205, 1983
47. Welte, K. et al, Defective Interleukin-2 production in patients after bone marrow transplantation and in vitro restoration of defective T lymphocyte proliferation by highly purified Interleukin. *Blood* 64:380, 1984.
48. Cayeau, S. et al., T-cell ontogeny after bone marrow transplantation: failure to synthesize Interleukin-2 (IL-2) and lack of CD2- and CD3-mediated proliferation by both CDE4+ and CD8+ cells even in the presence of exogenous IL-2. *Blood* 74:2270, 1989.
49. Bosley, A. et al., Interleukin-2 as consolidative immunotherapy against minimal residual disease. Nouv Rev Fr Hematol 32:13, 1990.
50. Caligiuri, M. A. et al, Extended continuous infusion low-dose recombinant Interleukin-2 in advanced cancer. Prolonged immunomodulation without significant toxicity. J Clin Oncol 9:2110, 1991.
51. Caligiuri, M. A. et al, Selective immune modulation of NK cells following prolonged infusions of low dose recombinant IL-2. J Clin Invest 91:123, 1993.
52. Caligiuri, M. A., Low-dose recombinant Interleukin-2 therapy: rationale and potential clinical applications. SEM in Oncol 20:3, 1993.
53. Klarnet, J. P. et al, Antigen-driven T cell clones can proliferate in vivo, eradicate disseminated leukemia and provide specific immunologic memory. J Immunol. 138: 4012, 1987.
54. Soiffer, R. J. et al, Clinical and immunologic effects of prolonged infusion of low-dose recombinant Interleukin-2 after autologous and T cell-depleted allogeneic bone marrow transplantation. *Blood* 79:517, 1992.
55. Soiffer, R. J. et al, Effect of low-dose Interleukin-2 on disease relapse after T-cell depleted allogeneic bone marrow transplantation. *Blood* 84:964, 1994.
56. Lauria, F. et al, Immunologic and clinical modifications following low-dose subcutaneous administration of rIL-2 in non-Hodgkin's lymphoma patients after autologous bone marrow transplantation. BMT 18:79, 1996.
57. Vey, N. et al, A pilot study of autologous bone marrow transplantation followed by recombinant Interleukin-2 in malignant lymphomas. Leukemia & Lymphoma 21:107, 1996.
58. Venugopal, P. et al, Upregulation of CD20 expression in CLL cells by cytokines. Submitted to ASH Meeting, December 1998.

What is claimed is:

1. A method for treating low grade or follicular non-Hodgkin's lymphoma (NHL) comprising administering to a patient a therapeutically effective amount of rituximab during a chemotherapeutic regimen, wherein the chemotherapeutic regimen consists of cyclophosphamide, vincristine, and prednisone (CVP therapy), wherein the method comprises administering 375 mg/m² of rituximab, and wherein the method provides a beneficial synergistic effect in the patient.

2. A method for treating low grade or follicular non-Hodgkin's lymphoma (NHL) comprising administering to a patient 375 mg/m² of C2B8 during a chemotherapeutic regimen consisting of cyclophosphamide, vincristine, and prednisone (CVP therapy).

3. A method for treating low grade or follicular non-Hodgkin's lymphoma (NHL) comprising administering to a patient 375 mg/m² of a chimeric anti-CD20 antibody during a chemotherapeutic regimen consisting of cyclophosphamide, vincristine, and prednisone (CVP therapy), wherein the chimeric anti-CD20 antibody is produced from nucleic acid encoding a light chain variable region comprising the amino acid sequence in SEQ ID NO: 1 and a heavy chain variable region comprising the amino acid sequence in SEQ ID NO: 2, and comprises human gamma 1 heavy-chain and kappa light-chain constant region sequences.

4. A method for treating low grade or follicular non-Hodgkin's lymphoma (NHL) comprising administering to a patient a therapeutically effective amount of rituximab during a chemotherapeutic regimen, wherein the chemotherapeutic regimen consists of cyclophosphamide, vincristine, and prednisone (CVP therapy), wherein the method comprises administering 375 mg/m$^2$ of rituximab once every 3 weeks for 8 doses, and wherein the method provides a beneficial synergistic effect in the patient.

5. A method for treating low grade or follicular non-Hodgkin's lymphoma (NHL) comprising administering to a patient 375 mg/m$^2$ of C2B8 once every 3 weeks for 8 doses during a chemotherapeutic regimen consisting of cyclophosphamide, vincristine, and prednisone (CVP therapy).

6. A method for treating low grade or follicular non-Hodgkin's lymphoma (NHL) comprising administering to a patient 375 mg/m$^2$ of a chimeric anti-CD20 antibody once every 3 weeks for 8 doses during a chemotherapeutic regimen consisting of cyclophosphamide, vincristine, and prednisone (CVP therapy), wherein the chimeric anti-CD20 antibody is produced from nucleic acid encoding a light chain variable region comprising the amino acid sequence in SEQ ID NO: 1 and a heavy chain variable region comprising the amino acid sequence in SEQ ID NO: 2, and comprises human gamma 1 heavy-chain and kappa light-chain constant region sequences.

* * * * *